US012488460B2

(12) United States Patent
Mao et al.

(10) Patent No.: US 12,488,460 B2
(45) Date of Patent: Dec. 2, 2025

(54) SYSTEMS AND METHODS FOR VASCULAR IMAGE PROCESSING

(71) Applicant: SHANGHAI UNITED IMAGING HEALTHCARE CO., LTD., Shanghai (CN)

(72) Inventors: Yufei Mao, Shanghai (CN); Xiong Yang, Shanghai (CN); Saisai Su, Shanghai (CN); Weijian Zou, Shanghai (CN); Ke Wu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 403 days.

(21) Appl. No.: 18/064,229

(22) Filed: Dec. 9, 2022

(65) Prior Publication Data

US 2023/0104945 A1 Apr. 6, 2023

Related U.S. Application Data

(63) Continuation of application No. PCT/CN2021/099197, filed on Jun. 9, 2021.

(30) Foreign Application Priority Data

Jun. 9, 2020 (CN) ......................... 202010517606.8
Jun. 9, 2020 (CN) ......................... 202010518681.6
Dec. 30, 2020 (CN) ......................... 202011631235.2

(51) Int. Cl.
*G06T 7/00* (2017.01)
*A61B 6/50* (2024.01)

(52) U.S. Cl.
CPC ............ *G06T 7/0012* (2013.01); *A61B 6/504* (2013.01); *G06T 2207/30101* (2013.01)

(58) Field of Classification Search
CPC ......... G06T 7/0012; G06T 2207/30101; G06T 2207/10072; G06T 2207/10116;
(Continued)

(56) References Cited

U.S. PATENT DOCUMENTS 9,767,557 B1 9/2017 Gulsun et al.
9,788,729 B2 10/2017 Waku et al.
(Continued)

FOREIGN PATENT DOCUMENTS

CN 101984916 A 3/2011
CN 106157320 A 11/2016
(Continued)

OTHER PUBLICATIONS

Kirisli et al. "Standardized evaluation framework for evaluating coronary artery stenosis detection, stenosis quantification and lumen segmentation algorithms in computed tomography angiography", Jun. 4, 2013, Medical Image Analysis 17 (2013) 859-876. (Year: 2013).*

(Continued)

*Primary Examiner* — Siamak Harandi
(74) *Attorney, Agent, or Firm* — METIS IP LLC

(57) ABSTRACT

Systems and methods for image processing are provided. The systems may include obtaining an initial image relating to a blood vessel. The system may include determining a centerline of the blood vessel based on the initial image. The system may also include determining one or more images to be segmented of the blood vessel based on the centerline and the initial image. The system may also include determining a boundary of the lumen of the blood vessel and a boundary of the wall of the blood vessel in the each image for each of the one or more images. The system may further include
(Continued)

analyzing the blood vessel based on the one or more boundaries of the lumen and the one or more boundaries of the wall.

19 Claims, 24 Drawing Sheets

(58) Field of Classification Search
CPC . G06T 2207/10132; G06T 2207/20084; G06T 2207/30172; G06T 7/12; A61B 6/504
See application file for complete search history.

(56) References Cited

U.S. PATENT DOCUMENTS

| | | | |
|---|---|---|---|
| 10,258,304 B1 | 4/2019 | Kiraly et al. | |
| 11,100,685 B2 | 8/2021 | Liang et al. | |
| 11,116,575 B2 | 9/2021 | Taylor | |
| 11,147,635 B1 | 10/2021 | Sganga et al. | |
| 2002/0086347 A1 | 7/2002 | Johnson et al. | |
| 2007/0265550 A1* | 11/2007 | Choi | A61M 5/427 600/584 |
| 2010/0076296 A1 | 3/2010 | Mittal et al. | |
| 2010/0128963 A1 | 5/2010 | Waku et al. | |
| 2010/0135561 A1 | 6/2010 | Moulik | |
| 2011/0224542 A1 | 9/2011 | Mittal et al. | |
| 2011/0235891 A1 | 9/2011 | Sonnemans et al. | |
| 2014/0094691 A1 | 4/2014 | Steinberg et al. | |
| 2017/0262733 A1 | 9/2017 | Gulsun et al. | |
| 2017/0277977 A1 | 9/2017 | Kitamura | |
| 2017/0372475 A1 | 12/2017 | Gulsun et al. | |
| 2018/0068437 A1 | 3/2018 | Bronkalla et al. | |
| 2018/0165810 A1 | 6/2018 | Jia et al. | |
| 2019/0029625 A1 | 1/2019 | Zhong et al. | |
| 2019/0130578 A1 | 5/2019 | Gulsun et al. | |
| 2019/0180153 A1 | 6/2019 | Buckler et al. | |
| 2019/0318476 A1 | 10/2019 | Isgum et al. | |
| 2019/0325579 A1 | 10/2019 | Wang et al. | |
| 2019/0362855 A1 | 11/2019 | Ma et al. | |
| 2020/0113450 A1 | 4/2020 | Nishioka et al. | |
| 2020/0320688 A1 | 10/2020 | Tu et al. | |
| 2020/0402666 A1 | 12/2020 | Wang et al. | |
| 2021/0241484 A1 | 8/2021 | Wang et al. | |
| 2021/0374950 A1 | 12/2021 | Gao et al. | |
| 2022/0004797 A1 | 1/2022 | Kitamura et al. | |
| 2022/0215956 A1 | 7/2022 | Kong et al. | |
| 2023/0074296 A1 | 3/2023 | Wang et al. | |
| 2023/0394654 A1 | 12/2023 | Hampe et al. | |
| 2024/0023937 A1 | 1/2024 | Wong et al. | |
| 2024/0037952 A1 | 2/2024 | Matsumoto et al. | |
| 2024/0386547 A1 | 11/2024 | Nadakuditi et al. | |

FOREIGN PATENT DOCUMENTS

| | | | |
|---|---|---|---|
| CN | 106548213 | A | 3/2017 |
| CN | 107273657 | A | 10/2017 |
| CN | 107563983 | A | 1/2018 |
| CN | 107644420 | A | 1/2018 |
| CN | 108073914 | A | 5/2018 |
| CN | 108717695 | A | 10/2018 |
| CN | 108765385 | A | 11/2018 |
| CN | 109544543 | A | 3/2019 |
| CN | 110163928 | A | 8/2019 |
| CN | 110189295 | A | 8/2019 |
| CN | 110310323 | A | 10/2019 |
| CN | 110390282 | A | 10/2019 |
| CN | 110517279 | A | 11/2019 |
| CN | 110619610 | A | 12/2019 |
| CN | 110675481 | A | 1/2020 |
| CN | 110889896 | A | 3/2020 |
| CN | 111145173 | A | 5/2020 |
| CN | 111178445 | A | 5/2020 |
| CN | 111461065 | A | 7/2020 |
| CN | 111681224 | A | 9/2020 |
| CN | 111681226 | A | 9/2020 |
| CN | 116912081 | A | 10/2023 |
| WO | 2016159881 | A1 | 10/2016 |
| WO | 2019005722 | A1 | 1/2019 |

OTHER PUBLICATIONS

Cheng, Shiyin et al., Centerline Extraction From MR Carotid Angiography Images, Chinese Journal of Stereology and Image Analysis, 21(4): 415-422, 2016.
He, Jiafa et al., Learning Hybrid Representations for Automatic 3D Vessel Centerline Extraction, MICCAI 2020, 24-34, 2020.
Rahil Shahzad et al., Automatic Segmentation, Detection and Quantification of Coronary Artery Stenoses on CTA, Int J Cardiovasc Imaging, 29(8): 1847-1859, 2013.
Zhou, Shi et al., Comparative Study of Three-Dimensional Reconstructed Images After Rotational DSA and Conventional DSA in The Diagnosis and Treatment of Carotid Stenosis, China J Radiol, 39(1): 92-96, 2005.
Liu, Yang, Association between the Characteristics of Subclinical Atherosclerotic Plaque in Multiple Vascular Beds and White Matter Lesions: High Resolution Magnetic Resonance Vessel Wall Imaging Study, Master's Degree Thesis, Yangzhou University, 2019, 62 pages.
The Extended European Search Report in European Application No. 20932198.3 mailed on Aug. 11, 2023, 8 pages.
International Search Report in PCT/CN2021/099197 mailed on Sep. 8, 2021, 4 pages.
Written Opinion in PCT/CN2021/099197 mailed on Sep. 8, 2021, 6 pages.
International Search Report in PCT/CN2020/137816 mailed on Mar. 18, 2021, 5 pages.
Written Opinion in PCT/CN2020/137816 mailed on Mar. 18, 2021, 5 pages.
Wu, Wei et al., CAR-Net: A Deep Learning-Based Deformation Model for 3D/2D Coronary Artery Registration, IEEE Transactions On Medical Imaging, 41(10): 2715-2727, 2022.

* cited by examiner

SYSTEMS AND METHODS FOR VASCULAR IMAGE PROCESSING

CROSS-REFERENCE TO RELATED APPLICATIONS

This application is a Continuation of International Application No. PCT/CN2021/099197, filed on Jun. 9, 2021, which claims priority of Chinese Patent Application No. 202010517606.8 filed on Jun. 9, 2020, Chinese Patent Application No. 202010518681.6 filed on Jun. 9, 2020, and Chinese Patent Application No. 202011631235.2 filed on Dec. 30, 2020, the contents of each of which are hereby incorporated by reference.

TECHNICAL FIELD

The disclosure generally relates to image processing, and more particularly relates to systems and methods for vascular image processing.

BACKGROUND

In recent years, the incidence and mortality of cerebrovascular diseases are increasing year by year at home and abroad, and cerebrovascular diseases gradually become one of the main causes of death. Although the clinical manifestation of the death is stroke, the root causing the death may be atherosclerosis. Atherosclerosis can lead to abnormal blood supply to functional cells of the brain of a patient. If the patient is not timely diagnosed and/or treated, the patient's physical condition and subsequent quality of life would be seriously affected, and it may even be fatal. Accordingly, it is important to analyze blood vessel(s) of the brain based on the vascular images of the patient. The current issue of concern is how to identify the main blood vessel(s) of the brain, detect the lesion of the blood vessel(s), and/or position the lesion in a vascular image of the patient automatically and quickly. The key to solving the issue may relate to the accuracy of vascular centerline(s) extracted from the vascular image(s) of the patient. Therefore, it is desired to provide systems and methods for image processing, especially for vascular image processing.

SUMMARY

In an aspect of the present disclosure, a system is provided. The system may include at least one storage device and at least one processor. The at least one storage device may store a set of instructions. The at least one processor may be configured to communicate with the at least one storage device. When executing the set of instructions, the at least one processor may be configured to direct the system to perform operations. The operations may include obtaining an initial image relating to a blood vessel. The initial image may include information of at least the lumen and the wall of the blood vessel. The operations may include determining a centerline of the blood vessel based on the initial image. The operations may also include determining one or more images to be segmented of the blood vessel based on the centerline and the initial image. Each of the one or more images may be an axial image of the blood vessel. The operations may include, for each of the one or more images, determining a boundary of the lumen of the blood vessel and a boundary of the wall of the blood vessel in the each image. The operations may further include analyzing the blood vessel based on the one or more boundaries of the lumen and the one or more boundaries of the wall.

In another aspect of the present disclosure, a method implemented on a computing device including at least one processor and at least one storage medium is provided. The method may include obtaining an initial image relating to a blood vessel. The initial image may include information of at least the lumen and the wall of the blood vessel. The method may include determining a centerline of the blood vessel based on the initial image. The method may also include determining one or more images to be segmented of the blood vessel based on the centerline and the initial image. Each of the one or more images may be an axial image of the blood vessel. The method may include, for each of the one or more images, determining a boundary of the lumen of the blood vessel and a boundary of the wall of the blood vessel in the each image. The method may further include analyzing the blood vessel based on the one or more boundaries of the lumen and the one or more boundaries of the wall.

In another aspect of the present disclosure, a system is provided. The system may include an obtaining module and a determination module. The obtaining module may be configured to obtain an initial image relating to a blood vessel. The initial image may include information of at least the lumen and the wall of the blood vessel. The determination module may be configured to a centerline of the blood vessel based on the initial image. The determination module may also be configured to one or more images to be segmented of the blood vessel based on the centerline and the initial image. Each of the one or more images may be an axial image of the blood vessel. The determination module may be configured to, for each of the one or more images, determine a boundary of the lumen of the blood vessel and a boundary of the wall of the blood vessel in the each image. The determination module may further be configured to analyze the blood vessel based on the one or more boundaries of the lumen and the one or more boundaries of the wall.

In another aspect of the present disclosure, a non-transitory computer readable medium is provided. The medium may include executable instructions that, when executed by at least one processor, direct the at least one processor to perform a method. The method may include obtaining an initial image relating to a blood vessel. The initial image may include information of at least the lumen and the wall of the blood vessel. The method may include determining a centerline of the blood vessel based on the initial image. The method may also include determining one or more images to be segmented of the blood vessel based on the centerline and the initial image. Each of the one or more images may be an axial image of the blood vessel. The method may include, for each of the one or more images, determining a boundary of the lumen of the blood vessel and a boundary of the wall of the blood vessel in the each image. The method may further include analyzing the blood vessel based on the one or more boundaries of the lumen and the one or more boundaries of the wall.

In another aspect of the present disclosure, a system is provided. The system may include at least one storage device and at least one processor. The at least one storage device may store a set of instructions. The at least one processor may be configured to communicate with the at least one storage device. When executing the set of instructions, the at least one processor may be configured to direct the system to perform operations. The operations may include obtaining a first image relating to a blood vessel. The operations may include determining a recognition result based on the first image using a first machine learning model. The recognition result may include a first enhanced image corresponding to the first image. The first enhanced image may indicate path information of a centerline of the blood vessel. The operations may further include determining the centerline of the blood vessel based on the first enhanced image.

In another aspect of the present disclosure, a method implemented on a computing device including at least one processor and at least one storage medium is provided. The method may include obtaining a first image relating to a blood vessel. The method may include determining a recognition result based on the first image using a first machine learning model. The recognition result may include a first enhanced image corresponding to the first image. The first enhanced image may indicate path information of a centerline of the blood vessel. The method may further include determining the centerline of the blood vessel based on the first enhanced image.

In another aspect of the present disclosure, a system is provided. The system may include an obtaining module and a determination module. The obtaining module may be configured to obtain a first image relating to a blood vessel. The determination module may be configured to determine a recognition result based on the first image using a first machine learning model. The recognition result may include a first enhanced image corresponding to the first image. The first enhanced image may indicate path information of a centerline of the blood vessel. The determination module may further be configured to determine the centerline of the blood vessel based on the first enhanced image.

In another aspect of the present disclosure, a non-transitory computer readable medium is provided. The medium may include executable instructions that, when executed by at least one processor, direct the at least one processor to perform a method. The method may include obtaining a first image relating to a blood vessel. The method may include determining a recognition result based on the first image using a first machine learning model. The recognition result may include a first enhanced image corresponding to the first image. The first enhanced image may indicate path information of a centerline of the blood vessel. The method may further include determining the centerline of the blood vessel based on the first enhanced image.

In another aspect of the present disclosure, a system is provided. The system may include at least one storage device and at least one processor. The at least one storage device may store a set of instructions. The at least one processor may be configured to communicate with the at least one storage device. When executing the set of instructions, the at least one processor may be configured to direct the system to perform operations. The operations may include obtaining at least two images relating to a blood vessel. The at least two images may be acquired using different imaging sequences. The operations may include determining a centerline of the blood vessel based on the at least two images. The operations may also include, for each of the at least two images, determining a set of curved planar reformation (CPR) images and/or a set of multi planar reformation (MPR) images based on the centerline of the blood vessel. The operations may further include causing at least two sets of CPR images and/or at least two sets of MPR images to be synchronously displayed on an interface.

In another aspect of the present disclosure, a method implemented on a computing device including at least one processor and at least one storage medium is provided. The method may include obtaining at least two images relating to a blood vessel. The at least two images may be acquired using different imaging sequences. The method may also include determining a centerline of the blood vessel based on the at least two images. The method may also include for each of the at least two images, determining a set of curved planar reformation (CPR) images and/or a set of multi planar reformation (MPR) images based on the centerline of the blood vessel. The method may further include causing at least two sets of CPR images and/or at least two sets of MPR images to be synchronously displayed on an interface.

In another aspect of the present disclosure, a system is provided. The system may include an obtaining module, a determination module, and a control module. The obtaining module may be configured to obtain at least two images relating to a blood vessel. The at least two images may be acquired using different imaging sequences. The determination module may be configured to determine a centerline of the blood vessel based on the at least two images. The determination module may also be configured to for each of the at least two images, determine a set of curved planar reformation (CPR) images and/or a set of multi planar reformation (MPR) images based on the centerline of the blood vessel. The control module may be configured to at least two sets of CPR images and/or at least two sets of MPR images to be synchronously displayed on an interface.

In another aspect of the present disclosure, a non-transitory computer readable medium is provided. The medium may include executable instructions that, when executed by at least one processor, direct the at least one processor to perform a method. The method may include obtaining at least two images relating to a blood vessel. The at least two images may be acquired using different imaging sequences. The method may also include determining a centerline of the blood vessel based on the at least two images. The method may also include for each of the at least two images, determining a set of curved planar reformation (CPR) images and/or a set of multi planar reformation (MPR) images based on the centerline of the blood vessel. The method may further include causing at least two sets of CPR images and/or at least two sets of MPR images to be synchronously displayed on an interface.

In another aspect of the present disclosure, a system is provided. The system may include at least one storage device and at least one processor. The at least one storage device may store a set of instructions. The at least one processor may be configured to communicate with the at least one storage device. When executing the set of instructions, the at least one processor may be configured to direct the system to perform operations. The operations may include obtaining an initial image relating to a blood vessel. The initial image may include information of at least the lumen and the wall of the blood vessel. The operations may include determining a centerline of the blood vessel based on the initial image. The operations may also include determining a labeled centerline based on the centerline using a third machine learning model. As used herein, the labeled centerline may include a name of the centerline and one or more labeled segments of the centerline. The operations may include identifying a target tissue from the initial image based on the centerline. The operations may further include determining a position of the target tissue based on the labeled centerline.

In another aspect of the present disclosure, a method implemented on a computing device including at least one processor and at least one storage medium is provided. The method may include obtaining an initial image relating to a blood vessel. The initial image may include information of at least the lumen and the wall of the blood vessel. The method may include determining a centerline of the blood vessel based on the initial image. The method may also include determining a labeled centerline based on the centerline using a third machine learning model. As used herein, the labeled centerline may include a name of the centerline and one or more labeled segments of the centerline. The method may also include identifying a target tissue from the initial image based on the centerline. The method may further include determining a position of the target tissue based on the labeled centerline.

In another aspect of the present disclosure, a system is provided. The system may include an obtaining module, and a determination module. The obtaining module may be configured to obtain an initial image relating to a blood vessel. The initial image may include information of at least the lumen and the wall of the blood vessel. The determination module may be configured to determine a centerline of the blood vessel based on the initial image. The determination module may also be configured to determine a labeled centerline based on the centerline using a third machine learning model. As used herein, the labeled centerline may include a name of the centerline and one or more labeled segments of the centerline. The determination module may also be configured to identify a target tissue from the initial image based on the centerline. The determination module may further be configured to determine a position of the target tissue based on the labeled centerline.

In another aspect of the present disclosure, a non-transitory computer readable medium is provided. The medium may include executable instructions that, when executed by at least one processor, direct the at least one processor to perform a method. The method may include obtaining an initial image relating to a blood vessel. The initial image may include information of at least the lumen and the wall of the blood vessel. The method may include determining a centerline of the blood vessel based on the initial image. The method may also include determining a labeled centerline based on the centerline using a third machine learning model. As used herein, the labeled centerline may include a name of the centerline and one or more labeled segments of the centerline. The method may also include identifying a target tissue from the initial image based on the centerline. The method may further include determining a position of the target tissue based on the labeled centerline.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections, or assembly of different levels in ascending order. However, the terms may be displaced by another expression if they achieve the same purpose.

Figure 2:
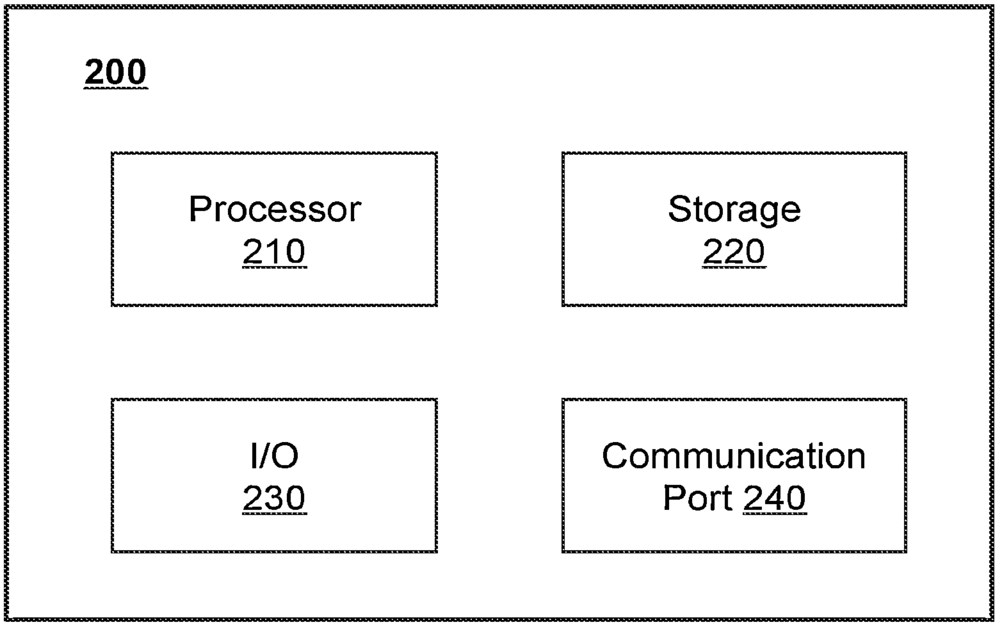
FIG. 2 is a schematic diagram illustrating hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module, or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items. The term "image" in the present disclosure is used to collectively refer to image data (e.g., scan data) and/or images of various forms, including a two-dimensional (2D) image, a three-dimensional (3D) image, a four-dimensional (4D) image, etc. The term "pixel" and "voxel" in the present disclosure are used interchangeably to refer to an element of an image.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of exemplary embodiments of the present disclosure.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and methods for non-invasive biomedical imaging, such as for disease diagnostic or research purposes. In some embodiments, the systems may include a single modality image processing system and/or a multi-modality image processing system. The single modality image processing system may include, for example, a magnetic resonance imaging (MRI) system, a computed tomography (CT) system, a digital subtraction angiography (DSA) system, an intravascular ultrasound (IVUS) device, etc. that can perform vascular imaging. The multi-modality image processing system may include, for example, a positron emission tomography-computed tomography (PET-CT) system, a digital subtraction angiography-computed tomography (DSA-CT) system, a single photon emission computed tomography-computed tomography (SPECT-CT) system, a computed tomography-magnetic resonance imaging (CT-MRI) system, a digital subtraction angiography-positron emission tomography (DSA-PET) system, a digital subtraction angiography-magnetic resonance imaging (DSA-MRI) system, a single photon emission computed tomography-magnetic resonance imaging (SPECT-MRI), a computed tomography guided radiotherapy (CT guided RT) system, etc. It should be noted that the image processing system described below is merely provided for illustration purposes, and not intended to limit the scope of the present disclosure.

The term "imaging modality" or "modality" as used herein broadly refers to an imaging method or technology that gathers, generates, processes, and/or analyzes imaging information of an object. The object may include a biological object and/or a non-biological object. The biological object may be a human being, an animal, a plant, or a portion thereof (e.g., a cell, a tissue, an organ, etc.). In some embodiments, the object may be a man-made composition of organic and/or inorganic matters that are with or without life. The term "object" or "subject" are used interchangeably.

In the present disclosure, a representation of an object (e.g., a patient, a subject, or a portion thereof) in an image may be referred to as an "object" for brevity. For instance, a representation of an organ or tissue (e.g., a heart, a liver, a lung) in an image may be referred to as an organ or tissue for brevity. Further, an image including a representation of an object may be referred to as an image of an object or an image including an object for brevity. Still further, an operation performed on a representation of an object in an image may be referred to as an operation performed on an object for brevity. For instance, a segmentation of a portion of an image including a representation of an organ or tissue from the image may be referred to as a segmentation of an organ or tissue for brevity.

As used herein, a 3D image described elsewhere in the present disclosure may include a plurality of 2D images (or slices). The phase "performing operation on a 3D image" may refer to "performing the operation directly on the 3D image" or "performing the operation on each of the plurality of 2D images (or slices) of the 3D image", which is not limited in the present disclosure.

Traditionally, a centerline of a blood vessel (also referred to as a vascular centerline) is determined (or extracted) manually by a user (e.g., a doctor). For example, the doctor may draw the vascular centerline in an image of the blood vessel (also referred to as a vascular image) (e.g., a cerebrovascular image) of a patient according to experiences of the doctor, which is cumbersome and inefficient. Further, the blood vessel may be identified based on the vascular centerline for subsequent analysis and diagnosis of vascular diseases by analyzing the blood vessel.

In some embodiments, the vascular analysis of the patient (e.g., the head and/or neck of the patient) may include measuring the lumen and the wall of the blood vessel, the accuracy of which depends on the segmentation of the lumen and the wall of the blood vessel from the vascular image. Currently, there are three main vascular segmentation technologies. A first vascular segmentation technology includes performing the segmentation of the lumen and the wall of the blood vessel by a manual or interactive manner, which is cumbersome, inefficient, difficult to repeat, and/or in lack of accuracy. A second vascular segmentation technology includes an automatic or semi-automatic segmentation technology such as an active contour algorithm, a semi-active contour algorithm, a graph-cut-based contour algorithm, a super-pixel-based segmentation algorithm, a Bayes-theory-based segmentation algorithm, etc., which may need the user to provide priori information. The priori information can be adjusted according to different images to be segmented for obtaining good segmentation results of the images. A third segmentation technology includes an automatic segmentation technology using a traditional machine learning model, e.g., by segmenting the image by extracting features of the image. If an actual clinical image mostly includes lesion data, the image may include complex lesion components that make features of the image complex, and it may be difficult to effectively extract features from variable images, which may make the segmentation result lack robustness and accuracy. Accordingly, there is no appropriate technology to measure the blood vessel (e.g., of the head and neck of the patient), especially, measure the vascular parameters of the blood vessel.

In some embodiments, after the segmentation of the lumen and the wall of the blood vessel, target tissue(s) (e.g., lesion(s) of the blood vessel) can be identified based on the segmentation results and positioned. Traditionally, a position of the target tissue (e.g., a blood vessel where the target tissue locates) is determined by the user, which is inefficient and lacks accuracy. In addition, a vascular segment where the target tissue locates may not be accurately determined. Therefore, it is desirable to provide systems and methods for vascular image processing, thereby improving efficiency and accuracy for analyzing the blood vessel of the patient.

An aspect of the present disclosure relates to systems and methods for analyzing a blood vessel. The systems and methods may obtain an initial image relating to the blood vessel including information of at least the lumen and the wall of the blood vessel. The system and methods may determine a centerline of the blood vessel based on the initial image (e.g., using a first machine learning model (i.e., an image recognition model)). The systems and methods may determine one or more images to be segmented of the blood vessel based on the centerline of the blood vessel and the initial image. Each of the one or more images being an axial image of the blood vessel. For each of the one or more images, the systems and methods may determine a boundary of the lumen of the blood vessel and a boundary of the wall of the blood vessel in the each image (e.g., using a second machine learning model (i.e., a boundary determination model)). The systems and methods may further analyze the blood vessel based on the one or more boundaries of the lumen and the one or more boundaries of the wall. According to some embodiments of the present disclosure, one or more images may be segmented automatically by inputting the images into the boundary determination model, which is efficient and accurate. In addition, the segmentation result(s) may be used to analyze the blood vessel (e.g., determine vascular parameters of the blood vessel, identify a target issue, determine a position of the target tissue, etc.).

Another aspect of the present disclosure relates to systems and methods for determining a centerline of a blood vessel using a first machine learning model (also referred to as an image recognition model). The systems and methods may obtain a first image relating to a blood vessel. The systems and methods may determine a recognition result based on the first image using the image recognition model. The recognition result may include a first enhanced image corresponding to the first image. The first enhanced image may indicate path information of a centerline of the blood vessel. The systems and methods may determine the centerline of the blood vessel based on the first enhanced image. According to some embodiments of the present disclosure, an enhanced image relating to a centerline of a blood vessel may be determined by directly inputting a first image relating to the blood vessel (and/or one or more second images relating to the blood vessel) to the image recognition model. In some embodiments, two or more images generated using different imaging sequences may be used to determine the enhanced image, so that more comprehensive information regarding the blood vessel can be used, thereby improving the accuracy of the enhanced image. The enhanced image may be used to determine at least two key points of the centerline accurately, thereby the centerline that is determined based on the at least two key points and the enhanced image may have a relatively high accuracy. In addition, by using the image recognition model, the centerline may be determined automatically and efficiently.

Another aspect of the present disclosure relates to systems and methods for displaying images corresponding to different imaging sequences synchronously. The systems and methods may obtain at least two images relating to a blood vessel which are acquired using different imaging sequences. The systems and methods may determine a centerline of the blood vessel based on the at least two images. For each of the at least two images, the systems and methods may determine a set of curved planar reformation (CPR) images and a set of multi planar reformation (MPR) images based on the centerline of the blood vessel. The systems and methods may cause at least two sets of CPR images and/or at least two sets of MPR images to be synchronously displayed on an interface. According to some embodiments of the present disclosure, different images corresponding to different imaging sequences can be displayed synchronously, the interface can present comprehensive information regarding the blood vessel and/or comparison between different images for users, thereby facilitating the users to view overall information of the blood vessel, and improving the analysis accuracy of the blood vessel.

Another aspect of the present disclosure relates to systems and methods for determining a position of a target tissue using a third machine learning model (also referred to as a labeled centerline determination model). The systems and methods may obtain an initial image relating to a blood vessel including information of at least the lumen and the wall of the blood vessel. The systems and methods may determine a labeled centerline based on a centerline of the blood vessel using the labeled centerline determination model. The labeled centerline may include a name of the centerline and one or more labeled segments of the centerline. The systems and methods may identify the target tissue from the initial image based on the centerline. For example, the systems and methods may determine one or more images of the blood vessel to be segmented by segmenting the initial image based on the centerline. The systems and methods may identify the target tissue by segmenting a boundary of the lumen and a boundary of the wall of the blood vessel in each of the one or more images. The systems and the methods may determine the position of the target tissue based on the labeled centerline. According to some embodiments of the present disclosure, a position of a target tissue of a blood vessel may be determined based on a labeled centerline of the blood vessel that is determined using the labeled centerline determination model, which is efficient and accurate. In addition, the position of the target tissue may be further used for subsequent analysis of the target tissue.

Figure 1:
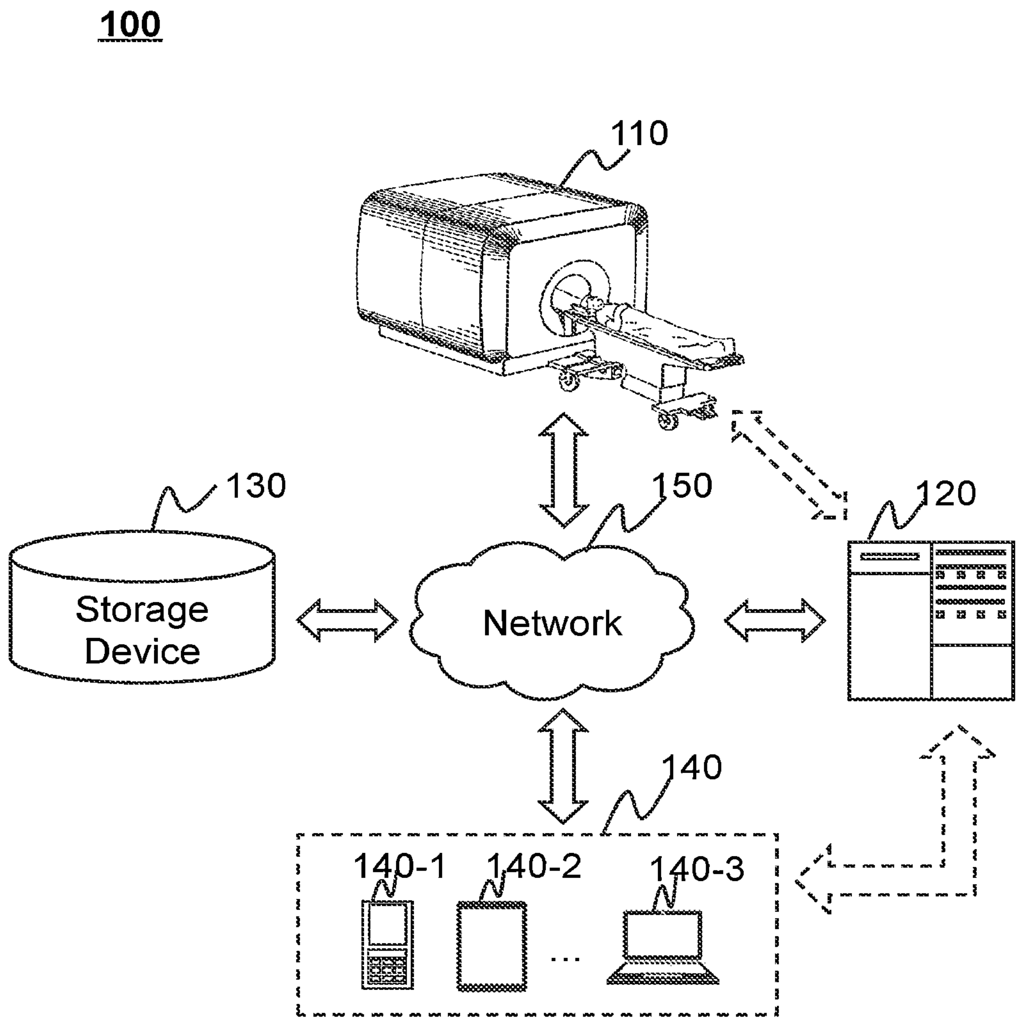
FIG. 1 is a schematic diagram illustrating an exemplary image processing system according to some embodiments of the present disclosure.

FIG. 1 is a schematic diagram illustrating an exemplary image processing system 100 according to some embodiments of the present disclosure. In some embodiments, the image processing system 100 may be associated with a single-modality system (e.g., an MRI system, a CT system, a DSA system, an IVUS system, etc.) or a multi-modality system (e.g., a PET-CT system, a DSA-CT system, an MRI-CT system, a DSA-MRI system, etc.). In some embodiments, the image processing system 100 may include modules and/or components for performing imaging and/or related analysis.

Merely by way of example, as illustrated in FIG. 1, the image processing system 100 may include an imaging device 110, a processing device 120, a storage device 130, one or more terminals 140, and a network 150. The components in the image processing system 100 may be connected in various ways. Merely by way of example, the imaging device 110 may be connected to the processing device 120 through the network 150 or directly as illustrated in FIG. 1. As another example, the terminal(s) 140 may be connected to the processing device 120 via the network 150 or directly as illustrated in FIG. 1.

In some embodiments, the imaging device 110 may be configured to obtain one or more images relating to a subject. The image relating to a subject may include an image, image data (e.g., projection data, scan data, etc.), or a combination thereof. In some embodiments, the image may include a two-dimensional (2D) image, a three-dimensional (3D) image, a four-dimensional (4D) image, or the like, or any combination thereof. The subject may be biological or non-biological. For example, the subject may include a patient, a man-made object, etc. As another example, the subject may include a specific portion, organ, and/or tissue of the patient. For example, the subject may include the head, the neck, the thorax, the heart, the stomach, a blood vessel, soft tissue, a tumor, nodules, or the like, or any combination thereof.

In some embodiments, the imaging device 110 may include a single modality imaging device and/or a multi-modality imaging device. The single modality imaging device may include, for example, an MRI device, a CT device, a DSA device, an IVUS device, or the like. The multi-modality imaging device may include, for example, an MRI-CT device, a PET-MRI device, a SPECT-MRI device, a DSA-MRI device, a PET-CT device, a SPECT-CT device, a DSA-CT device, a DSA-PET device, a CT-guided RT device, etc. For illustration purposes, the following description is described with reference to an MRI device unless specifically stated.

The processing device 120 may process data and/or information obtained from the imaging device 110, the terminal(s) 140, and/or the storage device 130. For example, the processing device 120 may determine an enhanced image relating to a centerline of a blood vessel based on at least one image (e.g., at least one MRI image) relating to the blood vessel using a first machine learning model. The processing device 120 may determine the centerline of the blood vessel based on the enhanced image. As another example, the processing device 120 may determine a centerline of a blood vessel based on at least two images relating to the blood vessel which are acquired using different imaging sequences. For each of the at least two images, the processing device 120 may determine one or more curved planar reformation (CPR) images and a set of multi planar reformation (MPR) images based on the centerline of the blood vessel. The processing device 120 may further cause at least two CPR images and/or at least two MPR images to be displayed on an interface. As a further example, the processing device 120 may determine a boundary of the lumen and the wall of a blood vessel based on an initial image relating to the blood vessel using a second machine learning model for analyzing the blood vessel. As a still further example, the processing device 120 may identify a target tissue (e.g., a lesion) from the initial image and determine a position of the target tissue based on a labeled centerline that is determined based on a centerline of the blood vessel using a third machine learning model.

In some embodiments, the processing device 120 may generate a machine learning model (e.g., the first/second/third machine learning model) by training an initial machine learning model using a plurality of training samples. In some embodiments, the generation and/or updating of the machine learning model may be performed by a processing device, while the application of the machine learning model may be performed by a different processing device. In some embodiments, the generation of the machine learning model may be performed by a processing device of a system different from the image processing system 100 or a server different from a server including the processing device 120 by which the application of the machine learning model is performed. For instance, the generation of the machine learning model may be performed by a first system of a vendor who provides and/or maintains such a machine learning model and/or has access to training samples used to generate the machine learning model, while image determination, boundary determination, or labeled centerline determination based on the provided machine learning model may be performed by a second system of a client of the vendor. In some embodiments, the generation of the machine learning model may be performed online in response to a request for image determination, boundary determination, or labeled centerline determination. In some embodiments, the generation of the machine learning model may be performed offline.

In some embodiments, the machine learning model may be generated and/or updated (or maintained) by, e.g., the manufacturer of the imaging device 110 or a vendor. For instance, the manufacturer or the vendor may load the model into the image processing system 100 or a portion thereof (e.g., the processing device 120) before or during the installation of the imaging device 110 and/or the processing device 120, and maintain or update the model from time to time (periodically or not). The maintenance or update may be achieved by installing a program stored on a storage device (e.g., a compact disc, a USB drive, etc.) or retrieved from an external source (e.g., a server maintained by the manufacturer or vendor) via the network 150. The program may include a new model (e.g., a new machine learning model) or a portion of a model that substitutes or supplements a corresponding portion of the model.

In some embodiments, the processing device 120 may be a computer, a user console, a single server or a server group, etc. The server group may be centralized or distributed. In some embodiments, the processing device 120 may be local or remote. For example, the processing device 120 may access information and/or data stored in the imaging device 110, the terminal(s) 140, and/or the storage device 130 via the network 150. As another example, the processing device 120 may be directly connected to the imaging device 110, the terminal(s) 140, and/or the storage device 130 to access stored information and/or data. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

The storage device 130 may store data, instructions, and/or any other information. In some embodiments, the storage device 130 may store data obtained from the terminal(s) 140 and/or the processing device 120. For example, the storage device 130 may store the images (e.g., MRI images, CT images, etc.) acquired by the imaging device 110. As another example, the storage device 130 may store one or more algorithms for processing the image data, one or more machine learning models for image determination, vascular centerline determination, boundary determination, labeled centerline determination, etc. In some embodiments, the storage device 130 may store data and/or instructions that the processing device 120 may execute or use to perform exemplary methods/systems described in the present disclosure. In some embodiments, the storage device 130 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components in the image processing system 100 (e.g., the processing device 120, the terminal(s) 140, etc.). One or more components in the image processing system 100 may access the data or instructions stored in the storage device 130 via the network 150. In some embodiments, the storage device 130 may be directly connected to or communicate with one or more other components in the image processing system 100 (e.g., the processing device 120, the terminal(s) 140, etc.). In some embodiments, the storage device 130 may be part of the processing device 120.

The terminal(s) 140 may include a mobile device 140-1, a tablet computer 140-2, a laptop computer 140-3, or the like, or any combination thereof. In some embodiments, the mobile device 140-1 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™ an Oculus Rift™, a Hololens™, a Gear VR™, etc. In some embodiments, the terminal(s) 140 may be part of the processing device 120.

The network 150 may include any suitable network that can facilitate the exchange of information and/or data for the image processing system 100. In some embodiments, one or more components of the imaging device 110, the terminal(s) 140, the processing device 120, the storage device 130, etc., may communicate information and/or data with one or more other components of the image processing system 100 via the network 150. For example, the processing device 120 may obtain an image from the imaging device 110 via the network 150. As another example, the processing device 120 may obtain user instructions from the terminal(s) 140 via the network 150. The network 150 may be and/or include a public network (e.g., the Internet), a private network (e.g., a local cell network (LAN), a wide cell network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 150 may include a cable network, a wireline network, a fiber-optic network, a telecommunications network, an intranet, a wireless local cell network (WLAN), a metropolitan cell network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the image processing system 100 may be connected to the network 150 to exchange data and/or information.

It should be noted that the above description of the image processing system 100 is merely provided for the purposes of illustration, and not intended to limit the scope of the present disclosure. For persons having ordinary skills in the art, multiple variations and modifications may be made under the teachings of the present disclosure. For example, the image processing system 100 may include one or more additional components and/or one or more components of the image processing system 100 described above may be omitted. Additionally or alternatively, two or more components of the image processing system 100 may be integrated into a single component. A component of the image processing system 100 may be implemented on two or more sub-components.

FIG. 2 is a schematic diagram illustrating hardware and/or software components of an exemplary computing device 200 according to some embodiments of the present disclosure. The computing device 200 may be used to implement any component of the image processing system as described herein. For example, the processing device 120 and/or a terminal 140 may be implemented on the computing device 200, respectively, via its hardware, software program, firmware, or a combination thereof. Although only one such computing device is shown, for convenience, the computer functions relating to the image processing system 100 as described herein may be implemented in a distributed fashion on a number of similar platforms, to distribute the processing load. As illustrated in FIG. 2, the computing device 200 may include a processor 210, a storage 220, an input/output (I/O) 230, and a communication port 240.

The processor 210 may execute computer instructions (program codes) and perform functions of the processing device 120 in accordance with techniques described herein. The computer instructions may include, for example, routines, programs, objects, components, signals, data structures, procedures, modules, and functions, which perform particular functions described herein. In some embodiments, the processor 210 may perform instructions obtained from the terminal(s) 140. In some embodiments, the processor 210 may include one or more hardware processors, such as a microcontroller, a microprocessor, a reduced instruction set computer (RISC), an application-specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operations A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the imaging device 110, the terminal(s) 140, the storage device 130, or any other component of the image processing system 100. In some embodiments, the storage 220 may include a mass storage device, a removable storage device, a volatile read-and-write memory, a read-only memory (ROM), or the like, or any combination thereof. In some embodiments, the storage 220 may store one or more programs and/or instructions to perform exemplary methods described in the present disclosure. For example, the storage 220 may store a program for the processing device 120 for performing image processing, such as image determination, vascular centerline determination, boundary determination, or labeled centerline determination.

The I/O 230 may input or output signals, data, and/or information. In some embodiments, the I/O 230 may enable user interaction with the processing device 120. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected with a network (e.g., the network 150) to facilitate data communications. The communication port 240 may establish connections between the processing device 120 and the imaging device 110, the terminal(s) 140, or the storage device 130. The connection may be a wired connection, a wireless connection, or a combination of both that enables data transmission and reception. The wired connection may include an electrical cable, an optical cable, a telephone wire, or the like, or any combination thereof. The wireless connection may include a Bluetooth™ network, a Wi-Fi network, a WiMax network, a WLAN, a ZigBee™ network, a mobile network (e.g., 3G, 4G, 5G, etc.), or the like, or any combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
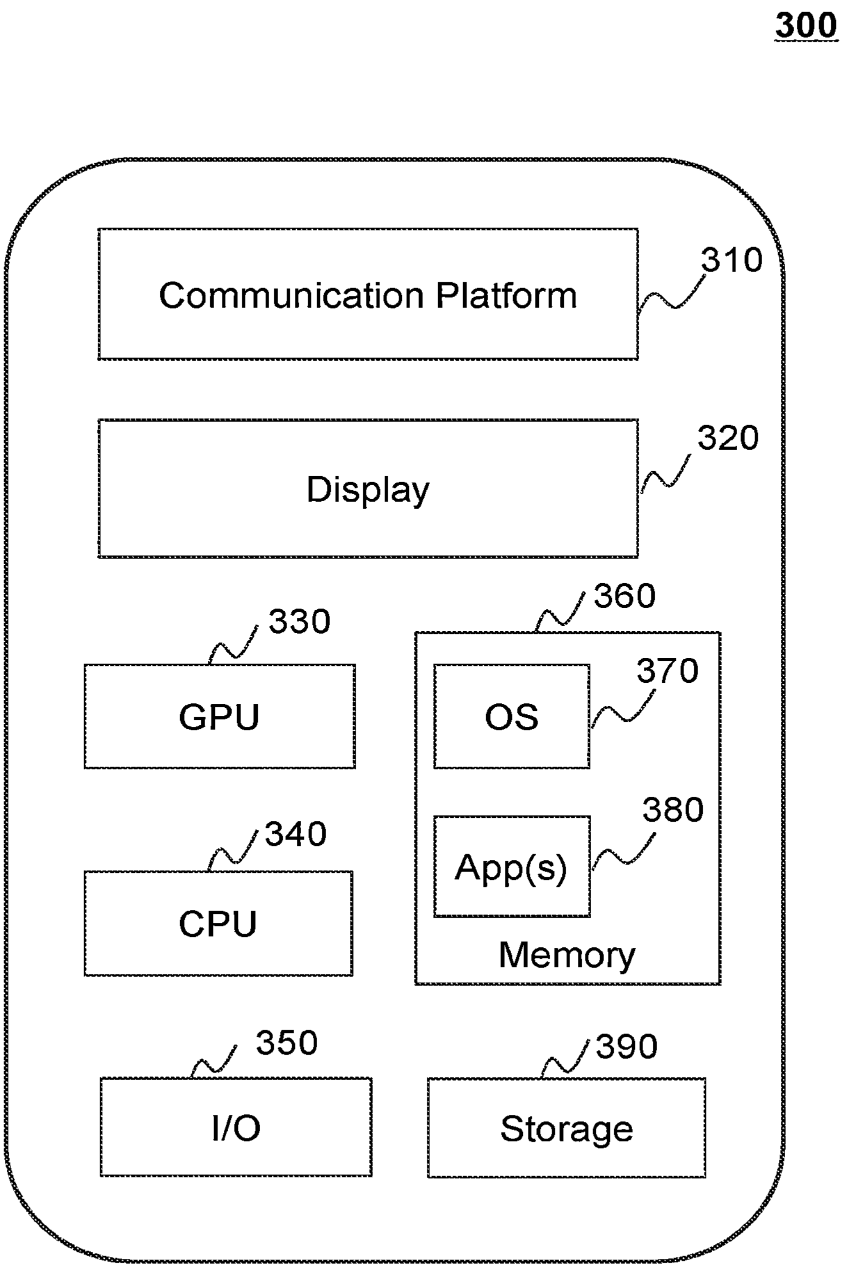
FIG. 3 is a schematic diagram illustrating hardware and/or software components of an exemplary mobile device according to some embodiments of the present disclosure.

FIG. 3 is a schematic diagram illustrating hardware and/or software components of an exemplary mobile device 300 according to some embodiments of the present disclosure. In some embodiments, one or more components (e.g., a terminal 140 and/or the processing device 120) of the image processing system 100 may be implemented on the mobile device 300.

As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 120. User interactions with the information stream may be achieved via the I/O 350 and provided to the processing device 120 and/or other components of the image processing system 100 via the network 150.

To implement various modules, units, and their functionalities described in the present disclosure, computer hardware platforms may be used as the hardware platform(s) for one or more of the elements described herein. The hardware elements, operating systems, and programming languages of such computers are conventional in nature, and it is presumed that those skilled in the art are adequately familiar therewith to adapt those technologies to generate an image as described herein. A computer with user interface elements may be used to implement a personal computer (PC) or another type of work station or terminal device, although a computer may also act as a server if appropriately programmed. It is believed that those skilled in the art are familiar with the structure, programming, and general operation of such computer equipment and as a result, the drawings should be self-explanatory.

Figure 4A:
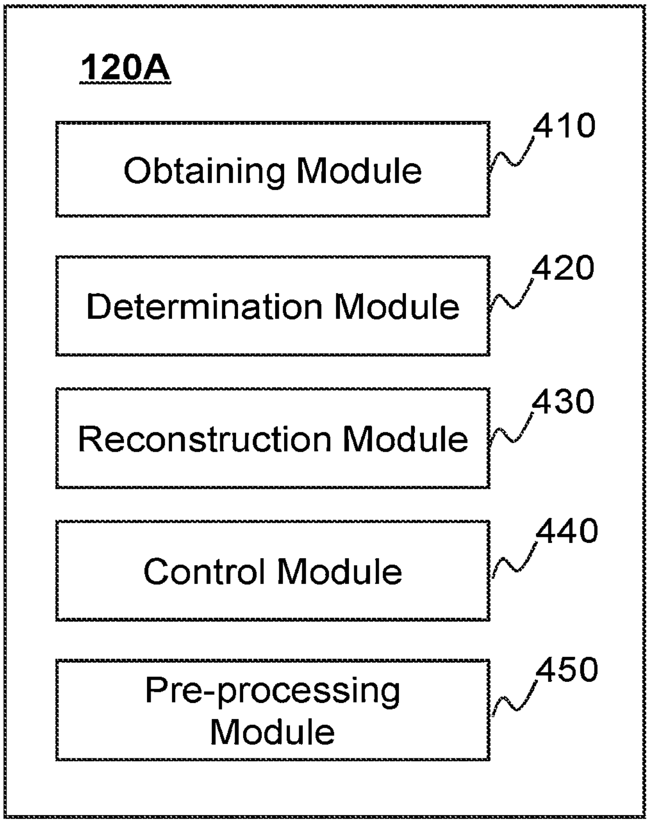
FIGS. 4A and 4B are block diagrams illustrating exemplary processing devices according to some embodiments of the present disclosure.
Figure 4B:
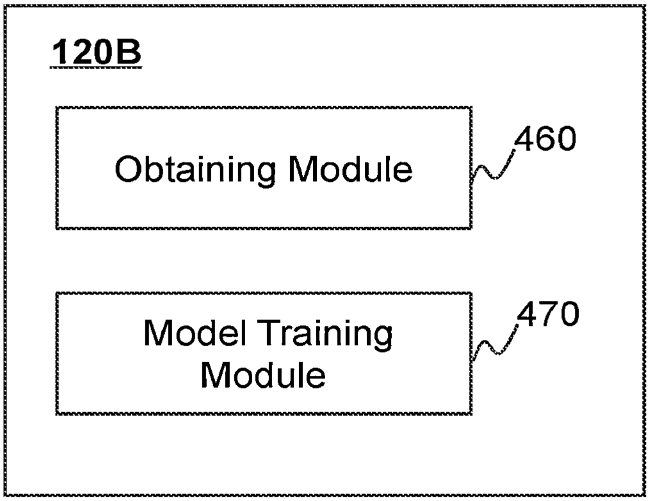

FIG. 4A and FIG. 4B are block diagrams illustrating exemplary processing devices 120A and 120B according to some embodiments of the present disclosure. In some embodiments, the processing devices 120A and 120B may be embodiments of the processing device 120 as described in connection with FIG. 1. In some embodiments, the processing devices 120A and 120B may be respectively implemented on a processing unit (e.g., the processor 210 illustrated in FIG. 2 or the CPU 340 as illustrated in FIG. 3). Merely by way of example, the processing devices 120A may be implemented on a CPU 340 of a terminal device, and the processing device 120B may be implemented on a computing device 200. Alternatively, the processing devices 120A and 120B may be implemented on a same computing device 200 or a same CPU 340. For example, the processing devices 120A and 120B may be implemented on a same computing device 200.

As shown in FIG. 4A, the processing device 120A may include an obtaining module 410, a determination module 420, a reconstruction module 430, a control module 440, and a pre-processing module 450.

The obtaining module 410 may be configured to obtain information/data for image processing described elsewhere in the present disclosure. For example, the obtaining module 410 may obtain one or more images (e.g., first/second image(s), first/second initial image(s)) relating to a blood vessel and/or image data relating to the blood vessel from a storage device (e.g., the storage device 130, the storage 220, the storage 390, or an external database). As another example, the obtaining module 410 may obtain one or more machine learning models (e.g., the image recognition model, the boundary determination model, and/or the labeled centerline determination model) from a storage device (e.g., the storage device 130, the storage 220, the storage 390, or an external database). More descriptions regarding the image(s), the image data, and/or the machine learning model(s) may be found elsewhere in the present disclosure (e.g., FIGS. 5, 6 12, 14, and 17 and relevant descriptions thereof).

The determination module 420 may be configured to determine data/information for analyzing a blood vessel. For example, the determination module 420 may determine a centerline of the blood vessel, e.g., by using a first machine learning model (i.e., the image recognition model), more descriptions of which can be found elsewhere in the present disclosure (e.g., FIGS. 5-7 and relevant descriptions thereof). As another example, the determination module 420 may determine one or more images of the blood vessel to be segmented based on the centerline. The determination module 420 may determine a boundary of the lumen of the blood vessel and/or a boundary of the wall of the blood vessel in each of the image(s), e.g., by using a second machine learning model (i.e., the boundary determination model), more descriptions of which can be found elsewhere in the present disclosure (e.g., FIG. 14 and relevant descriptions thereof). As still another example, the determination module 420 may identify a target tissue of the blood vessel based on the boundaries of the lumen and the boundaries of the wall in the image(s). The determination module 420 may determine a position of the target tissue based on a labeled centerline that is determined using a third machine learning model (i.e., the labeled centerline determination model), more descriptions of which can be found elsewhere in the present disclosure (e.g., FIG. 17 and relevant descriptions thereof).

The reconstruction module 430 may be configured to reconstruct images relating to a blood vessel. For example, the reconstruction module 430 may reconstruct an initial image (e.g., the first/second image, the first/second initial image, etc.) relating to the blood vessel based on image data relating to the blood vessel. As another example, the reconstruction module 430 may determine one or more CPR images and/or MPR images relating to the blood vessel based on a centerline of the blood vessel, more descriptions of which can be found elsewhere in the present disclosure (e.g., FIG. 12 and relevant descriptions thereof).

Figure 12:
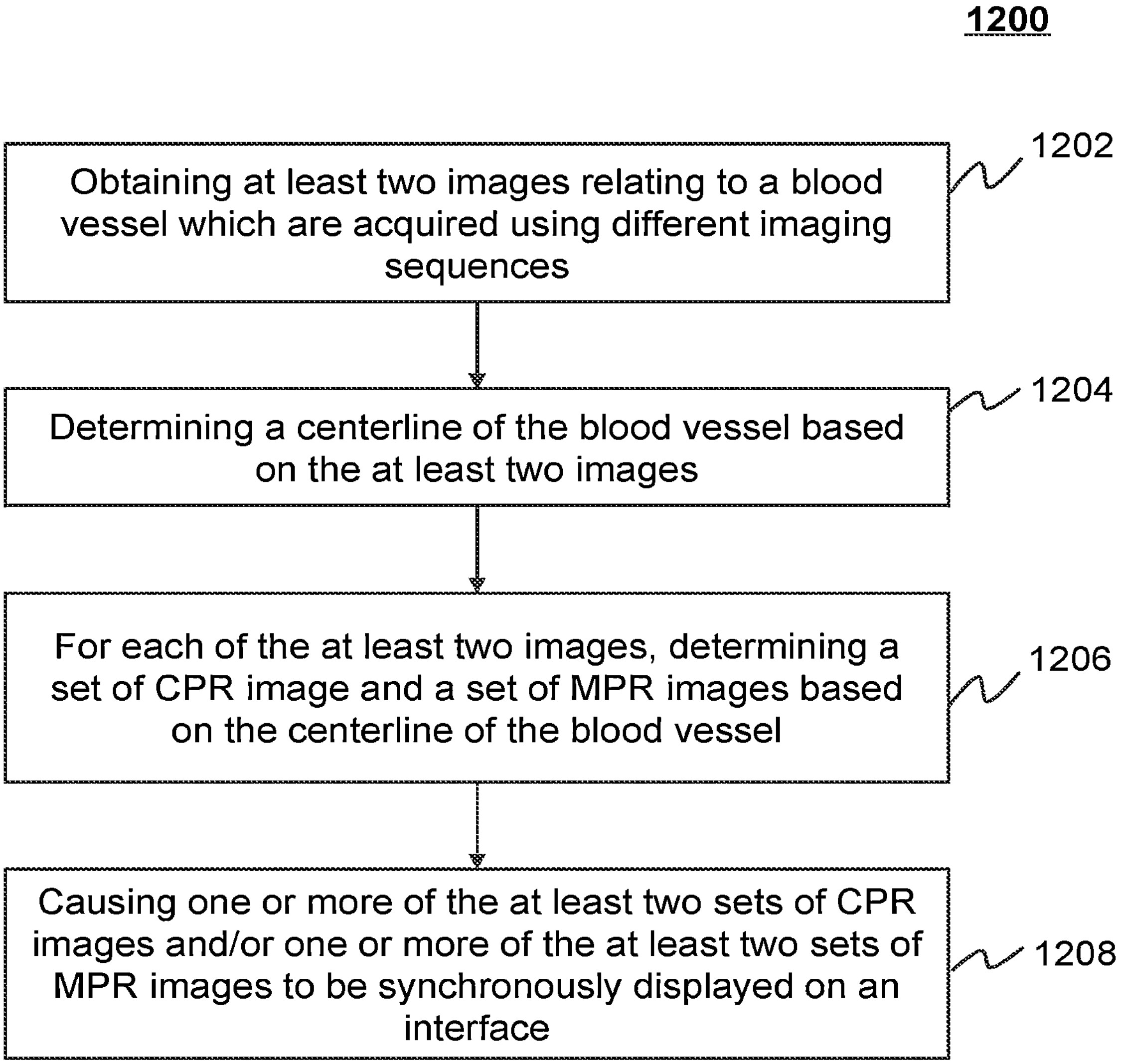
FIG. 12 is a flowchart illustrating an exemplary process for displaying CPR images and MPR images according to some embodiments of the present disclosure.

The control module 440 may be configured to cause one or more images relating to a blood vessel to be displayed. For example, the control module 440 may cause one or more initial images (e.g., one or more images acquired using different imaging sequences) relating to the blood vessel to be synchronously displayed on an interface. As another example, the control module 440 may cause one or more CPR images and/or one or more MPR images relating to the blood vessel to be synchronously displayed on the interface according to a preset layout. As still another example, the control module 440 may cause a centerline of the blood vessel, a boundary of the lumen of the blood vessel and a boundary of the wall of the blood vessel, and/or a target tissue of the blood vessel in one or more CPR images and/or MPR images relating to the blood vessel. More descriptions regarding the display of image(s) may be found elsewhere in the present disclosure (FIG. 12 and relevant descriptions thereof). In some embodiments, the control module 440 may cause the imaging device 110 *o* to perform a scan on a subject including the blood vessel.

The pre-processing module 450 may be configured to perform a pre-processing operation on image(s) relating to a blood vessel. For example, the pre-processing module 450 may register a first image relating to the blood vessel and one or more second images relating to the blood vessel before inputting the first image and the second image(s) into the image recognition model, more descriptions of which can be found elsewhere in the present disclosure (e.g., FIG. 6 and relevant descriptions thereof). As another example, the pre-processing module 450 may perform image resizing, image resampling, and image normalization on an image relating to the blood vessel.

As shown in FIG. 4B, the processing device 120B may include an obtaining module 460 and a model training model 470.

The obtaining module 460 may be configured to obtain data/information for model training. For example, the obtaining module 460 may obtain a plurality of training samples (or sample images) and/or gold standard images corresponding to the training samples. As another example, the obtaining module 460 may obtain an initial machine learning model for training a machine learning model (e.g., the image recognition model, the boundary determination model, and/or the labeled centerline determination model). More descriptions regarding the obtaining of the training samples, the gold standard images, and/or the initial machine learning model can be found elsewhere in the present disclosure (e.g., FIGS. 9, 15, and 18 and relevant description thereof).

The model training module 470 may be configured to determine a machine learning model (e.g., the image recognition model, the boundary determination model, and/or the labeled centerline determination model). For example, the model training module 470 may determine the machine learning model by training the initial machine learning model using the training samples and corresponding gold standard images. More descriptions regarding the training process may be found elsewhere in the present disclosure (e.g., FIGS. 9, 15, and 18 and relevant description thereof).

It should be noted that the above description is merely provided for the purposes of illustration, and not intended to limit the scope of the present disclosure. Apparently, for persons having ordinary skills in the art, multiple variations and modifications may be conducted under the teachings of the present disclosure. However, those variations and modifications do not depart from the scope of the present disclosure. Each of the modules described above may be a hardware circuit that is designed to perform certain actions, e.g., according to a set of instructions stored in one or more storage media, and/or any combination of the hardware circuit and the one or more storage media.

In some embodiments, the processing device 120A and/or the processing device 120B may share two or more of the modules, and any one of the modules may be divided into two or more units. For instance, the processing devices 120A and 120B may share a same obtaining module, that is, the obtaining module 410 and the obtaining module 460 are a same module. As another example, the determination module 420 may be divided into multiple units such as a first determination unit, a second determination unit, and a third determination unit. The first determination unit may be configured to determine the centerline of the blood vessel. The second determination unit may be configured to determine the boundary of the lumen and the boundary of the wall of the blood vessel in each image to be segmented. The third determination unit may be configured to determine the position of the target tissue of the blood vessel. As still another example, the model training module 470 may be divided into multiple units for determining the image recognition model, the boundary determination model, and the labeled centerline determination model separately. In some embodiments, the processing device 120A and/or the processing device 120B may include one or more additional modules, such as a storage module (not shown) for storing data. In some embodiments, the processing device 120A and the processing device 120B may be integrated into one processing device 120. In some embodiments, one or more modules of the processing device 120A and/or 120B may be omitted. For example, the pre-processing module 450 may be omitted.

Figure 5:
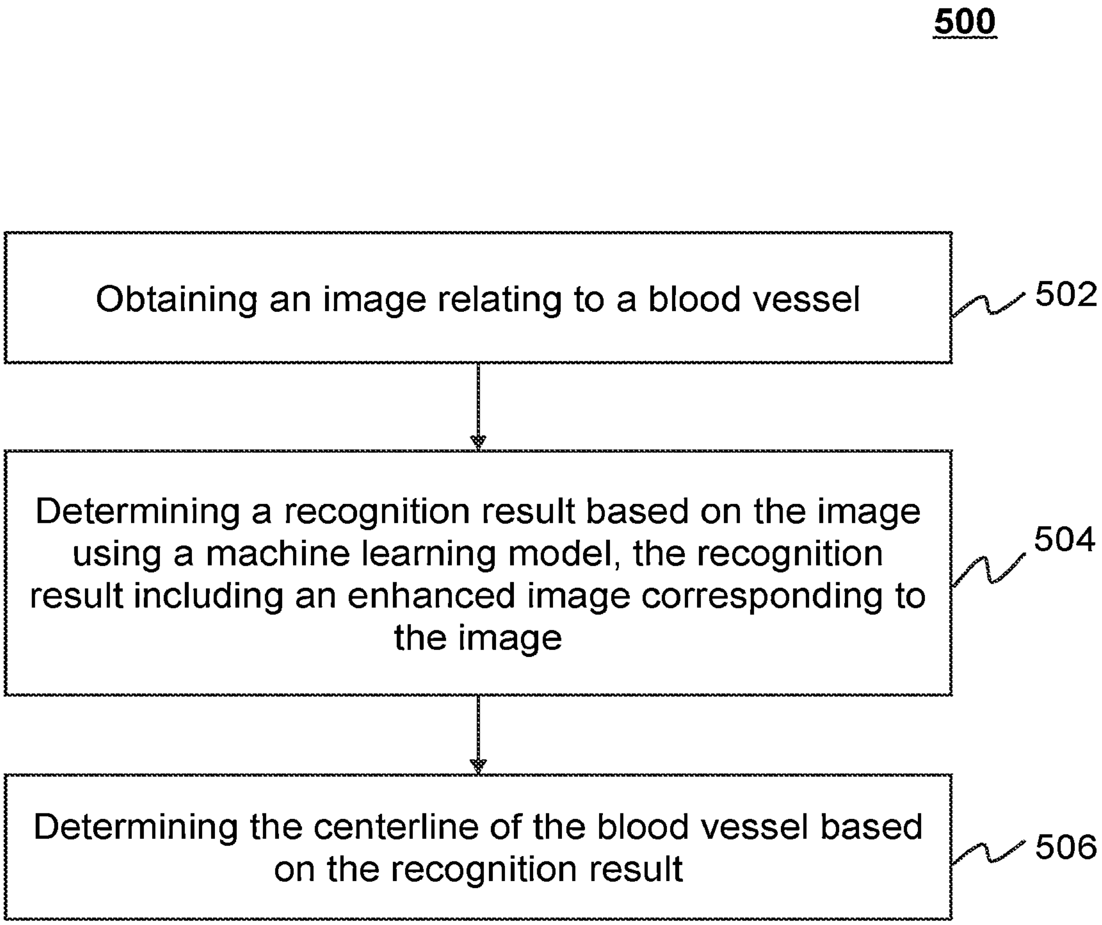
FIG. 5 is a flowchart illustrating an exemplary process for determining a centerline of a blood vessel according to some embodiments of the present disclosure.

FIG. 5 is a flowchart illustrating an exemplary process 500 for determining a centerline of a blood vessel according to some embodiments of the present disclosure. In some embodiments, process 500 may be implemented as a set of instructions (e.g., an application) stored in a storage device (e.g., the storage device 130, the storage 220, and/or the storage 390). The processing device 120A (e.g., the processor 210, the CPU 340, and/or one or more modules illustrated in FIG. 4A) may execute the set of instructions, and when executing the instructions, the processing device 120A may be configured to perform the process 500. The operations of the illustrated process presented below are intended to be illustrative. In some embodiments, the process 500 may be accomplished with one or more additional operations not described and/or without one or more of the operations discussed. Additionally, the order of the operations of process 500 illustrated in FIG. 5 and described below is not intended to be limiting.

In 502, the processing device 120A (e.g., the obtaining module 410) may obtain an image relating to a blood vessel.

The blood vessel refers to a blood vessel of a subject. The subject may be biological or non-biological. For example, the subject may include a patient, an animal, etc. As another example, the subject may include a specific portion, organ, and/or tissue of the patient. For instance, the subject may include the brain, the neck, the heart, a lung, or the like, or any combination thereof the patient. Accordingly, the blood vessel may include a blood vessel of the brain, a blood vessel of the neck, a blood vessel of a lung, etc. In some embodiments, the blood vessel may be of various types. For example, the blood vessel may include an arterial blood vessel, a venous blood vessel, and/or a capillary. In some embodiments, the blood vessel may include a lesion, such as a plaque, an ulceration, a thrombosis, an inflammation, an obstruction, a tumor, etc. The image(s) of the blood vessel may be used to determine a condition of the blood vessel (e.g., whether the blood vessel has a lesion).

The image relating to the blood vessel (also referred to as a first image) may include a three-dimensional (3D) image (e.g., including a plurality of 2D images (or slices)) including information of the blood vessel. The first image may be acquired by an imaging device (e.g., the imaging device 110). For example, the first image may be acquired by an MRI device, a CT device, a DSA device, an IVUS device, or the like, or any combination thereof. Taking the first image acquired by an MRI device as an example, the first image may include an MR image acquired according to an imaging sequence (also referred to as a first imaging sequence) (e.g., a Magnetic Resonance Angiography (MRA) imaging sequence). Exemplary imaging sequences may include a dark blood imaging sequence, a bright blood imaging sequence, etc. The dark blood imaging sequence may include a T1 enhanced sequence, a T1 sequence, a T2 sequence, a proton density sequence, etc. The bright blood imaging sequence may include a time of flight (Tof) sequence, a contrast-enhanced magnetic resonance angiography (CEMRA) sequence, etc.

In some embodiments, the first image may be previously generated and stored in a storage device (e.g., the storage device 130, the storage 220, the storage 390, etc.) or an external storage device (e.g., a medical image database). The processing device 120A may retrieve the first image from the storage device. In some embodiments, the processing device 120A may obtain the first image by causing the imaging device to perform a scan on the subject including the blood vessel. For example, the processing device 120A may cause an MRI device to perform a scan on the blood vessel using the first imaging sequence (e.g., a dark blood imaging sequence or a bright blood imaging sequence). After the MRI device scans the blood vessel according to the first imaging sequence, the processing device 120A may obtain scanning images (i.e., the first image) from the MRI device. Alternatively, the processing device 120A may obtain scan data acquired during the scan of the blood vessel. The processing device 120A may generate the first image based on the scan data using an MR reconstruction algorithm. Exemplary MR image reconstruction algorithms may include a Fourier transform algorithm, a back projection algorithm (e.g., a convolution back projection algorithm, or a filtered back projection algorithm), an iteration reconstruction algorithm, etc.

In 504, the processing device 120A (e.g., the determination module 420) may determine a recognition result based on the image using a machine learning model (also referred to as an image recognition model, or a first machine learning model).

The recognition result may include an enhanced image (also referred to as a first enhanced image) corresponding to the first image. The first enhanced image may be denoted in a form of a heatmap. The first enhanced image may indicate path information of a centerline of the blood vessel, and may also be referred to as an enhanced image relating to the centerline. In some embodiments, the path information may be indicated by values of pixels, coordinates of the pixels, etc., in the first enhanced image. The values of the pixels may refer to grayscale values of the pixels. For example, the closer a pixel in the first enhanced image is to the centerline of the blood vessel, the larger the grayscale value of the pixel in the first enhanced image may be. In some embodiments, the recognition result may further include a second enhanced image. The second enhanced image may include information of at least two initial key points, and may also be referred to as an enhanced image relating to key points. Alternatively, the recognition result may include more than one second enhanced image. Each of the second enhanced image(s) may include one or more initial key points. For example, the first image may be input to the image recognition model, and the image recognition model may output the first enhanced image and the more than one second enhanced image each of which including only one initial key point. The at least two initial key points may be determined based on the more than one second enhanced image. Further, the at least two initial key points may be used to determine at least two key points of the centerline of the blood vessel for subsequent determination of the centerline of the blood vessel. More descriptions regarding the key point(s) may be found elsewhere in the present disclosure. See, e.g., FIG. 8 and relevant descriptions thereof.

The image recognition model may refer to a process or an algorithm for determining a recognition result based on the first image. The image recognition model may include a trained convolutional neural network (CNN) model, a trained generative adversarial network (GAN) model, or any other suitable type of model. Exemplary trained CNN models may include a trained Fully Convolutional Network, such as a trained V-NET model, a trained U-NET model, etc. Exemplary trained GAN models may include a trained pix2pix model, a trained Wasserstein GAN (WGAN) model, a trained circle GAN model, etc.

In some embodiments, the processing device 120A may determine the enhanced image by inputting the first image into the image recognition model. For example, the processing device 120A may input the first image into the image recognition model, and the image recognition model may output the recognition result corresponding to the first image. In some embodiments, the processing device 120A may obtain one or more second images relating to the blood vessel. Each of the one or more second images may include a 3D image including information of the blood vessel. Each of the one or more second images may be acquired using a second imaging sequence different from the first imaging sequence. The processing device 120A may determine the recognition result based on the first image and the one or more second images using the image recognition model, more descriptions of which may be found elsewhere in the present disclosure (e.g., FIG. 6 and relevant descriptions thereof).

In some embodiments, according to a count of input(s) and/or output(s) of the image recognition model, the image recognition model may include different types including a single-input-output type, a single-input and multi-output type, a multi-input and single-output type, a multi-input-output type, etc. For the single-input-output type, the processing device 120A may input the first image into the image recognition model, and the image recognition model may output the first enhanced image corresponding to the first image. For the single-input and multi-output type, the processing device 120A may input the first image into the image recognition model, and the image recognition model may output the first enhanced image corresponding to the first image and at least one second enhanced image including initial key points. For the multi-input and single-output model, the processing device 120A may input the first image and the one or more second images into the image recognition model, and the image recognition model may output the first enhanced image corresponding to the first image in consideration information in the first image and the one or more second images. For the multi-input-output type, the processing device 120A may input the first image and the one or more second images into the image recognition model, and the image recognition model may output the first enhanced image corresponding to the first image and at least one second enhanced image including initial key points. Alternatively, the processing device 120A may input the first image and the one or more second images together into the image recognition model, and the image recognition model may output the recognition result including the first enhanced image corresponding to the first image and one or more third enhanced image each of which corresponds to one of the one or more second images. More descriptions regarding the input and the output of the image recognition model may be found elsewhere in the present disclosure. See, e.g., FIG. 6 and relevant descriptions thereof.

In some embodiments, the processing device 120A (e.g., the obtaining module 410) may obtain the image recognition model from one or more components of the image processing system 100 (e.g., the storage device 130, the terminals(s) 140) or an external source via a network (e.g., the network 150). For example, the image recognition model may be previously generated by a computing device (e.g., the processing device 120B), and stored in a storage device (e.g., the storage device 130, the storage 220, and/or the storage 390) of the image processing system 100. Alternatively, the image recognition model may be provided by a vendor that provides and/or updates the image recognition model and/or stored in a third-party database. The processing device 120A may access the storage device and/or the third-party database to retrieve the image recognition model. In some embodiments, the image recognition model may be generated according to a machine learning algorithm. The machine learning algorithm may include but not be limited to an artificial neural network algorithm, a deep learning algorithm, a decision tree algorithm, an association rule algorithm, an inductive logic programming algorithm, a support vector machine algorithm, a clustering algorithm, a Bayesian network algorithm, a reinforcement learning algorithm, a representation learning algorithm, a similarity and metric learning algorithm, a sparse dictionary learning algorithm, a genetic algorithm, a rule-based machine learning algorithm, or the like, or any combination thereof. The machine learning algorithm used to generate the image recognition model may be a supervised learning algorithm, a semi-supervised learning algorithm, an unsupervised learning algorithm, etc. In some embodiments, the image recognition model may be generated by a computing device (e.g., the processing device 120B) by performing a training process (e.g., process 900) for generating the image recognition model disclosed herein. More descriptions regarding the generation of the image recognition model may be found elsewhere in the present disclosure. See, e.g., FIG. 9 and relevant descriptions thereof.

In 506, the processing device 120A (e.g., the determination module 420) may determine the centerline of the blood vessel based on the recognition result (e.g., the first enhanced image).

In some embodiments, the processing device 120A may determine at least two key points of the centerline based on the first enhanced image. The key point(s) may include an endpoint of the centerline (e.g., a starting point of the centerline, or an ending point of the centerline), an intersection point between the centerline and another centerline of another blood vessel, an inflection point of the centerline, or the like, or any combination thereof. More descriptions regarding the determination of the at least two key points may be found elsewhere in the present disclosure. See, e.g., FIG. 8 and relevant descriptions thereof. The processing device 120A may further determine the centerline of the blood vessel based on the at least two key points and the enhanced image. For example, the processing device 120A may combine the enhanced image and the first image. The processing device 120A may further determine the centerline of the blood vessel based on the combined image and the at least two key points. More descriptions regarding the determination of the centerline may be found elsewhere in the present disclosure. See, e.g., FIGS. 6 and 7 and relevant descriptions thereof.

In some embodiments, the processing device 120A may transmit the centerline of the blood vessel to a terminal (e.g., the terminal 140) for display. Alternatively, the processing device 120A may transmit the centerline of the blood vessel to a storage device (e.g., the storage device 130) for storage. The processing device 120A may access the centerline of the blood vessel from the storage device for performing subsequent operations, such as determining CPR images and/or MPR images, determining one or more images (e.g., cross-section images) of the blood vessel to be segmented, determining a labeled centerline, etc., for analyzing the blood vessel. For example, the processing device 120A may determine first curved planar reformation (CPR) image(s) and first multi planar reformation (MPR) image(s) of the blood vessel based on the centerline of the blood vessel and the first image. The processing device 120A may cause the first CPR image(s) and/or the first MPR image(s) to be synchronously displayed on an interface (e.g., an interface of the terminal 140). As another example, the centerline of the blood vessel may be determined based on the first image and the one or more second images, the processing device 120A may determine second CPR image(s) and second MPR image(s) corresponding to each of the one or more second images based on the centerline of the blood vessel and the each second image. The processing device 120A may cause the first CPR image(s), the first MPR image(s), the second CPR image(s), and the second MPR image(s) to be synchronously displayed on the interface. More descriptions regarding the display of the images may be found elsewhere in the present disclosure. See, e.g., FIG. 12 and relevant descriptions thereof.

As another example, the processing device 120A may determine the one or more images of the blood vessel to be segmented based on the centerline. The processing device 120A may determine a boundary of the lumen and a boundary of the wall of the blood vessel in each of the one or more images to be segmented (e.g., using a second machine learning model as described in FIG. 14 and relevant descriptions thereof). The processing device 120A may analyze the blood vessel (e.g., identifying a target tissue of the blood vessel) based on the boundaries of the lumen and the boundaries of the wall of the blood vessel. More descriptions regarding the analysis of the blood vessel may be found elsewhere in the present disclosure (e.g., FIG. 14 and relevant descriptions thereof). As another example, the processing device 120A may determine a labeled centerline based on the centerline of the blood vessel (e.g., using a third machine learning model as described in FIG. 17 and relevant descriptions thereof). The processing device 120A may further determine a position of a target tissue of the blood vessel based on the labeled centerline. More descriptions regarding the determination of the position of the target tissue may be found elsewhere in the present disclosure (e.g., FIG. 17 and relevant descriptions thereof).

It should be noted that the above description regarding the process 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations of the process 500 may be omitted, and/or one or more additional operations may be added. For example, a storing operation may be added elsewhere in the process 500. In the storing operation, the processing device 120A may store information and/or data (e.g., the image related to the blood vessel, the enhanced image, the image recognition model, etc.) associated with the image processing system 100 in a storage device (e.g., the storage device 130) disclosed elsewhere in the present disclosure. As another example, the process 500 may include a display operation after the operation 506 for further displaying the centerline of the blood vessel. As still another example, an operation for obtaining one or more second images relating to the blood vessel may be added between the operation 502 and the operation 504. In some embodiments, a first image recognition model may be configured for outputting an enhanced image relating to the centerline, and a second image recognition model may be configured for determining an enhanced image relating to the at least two key points of the centerline.

Figure 6:
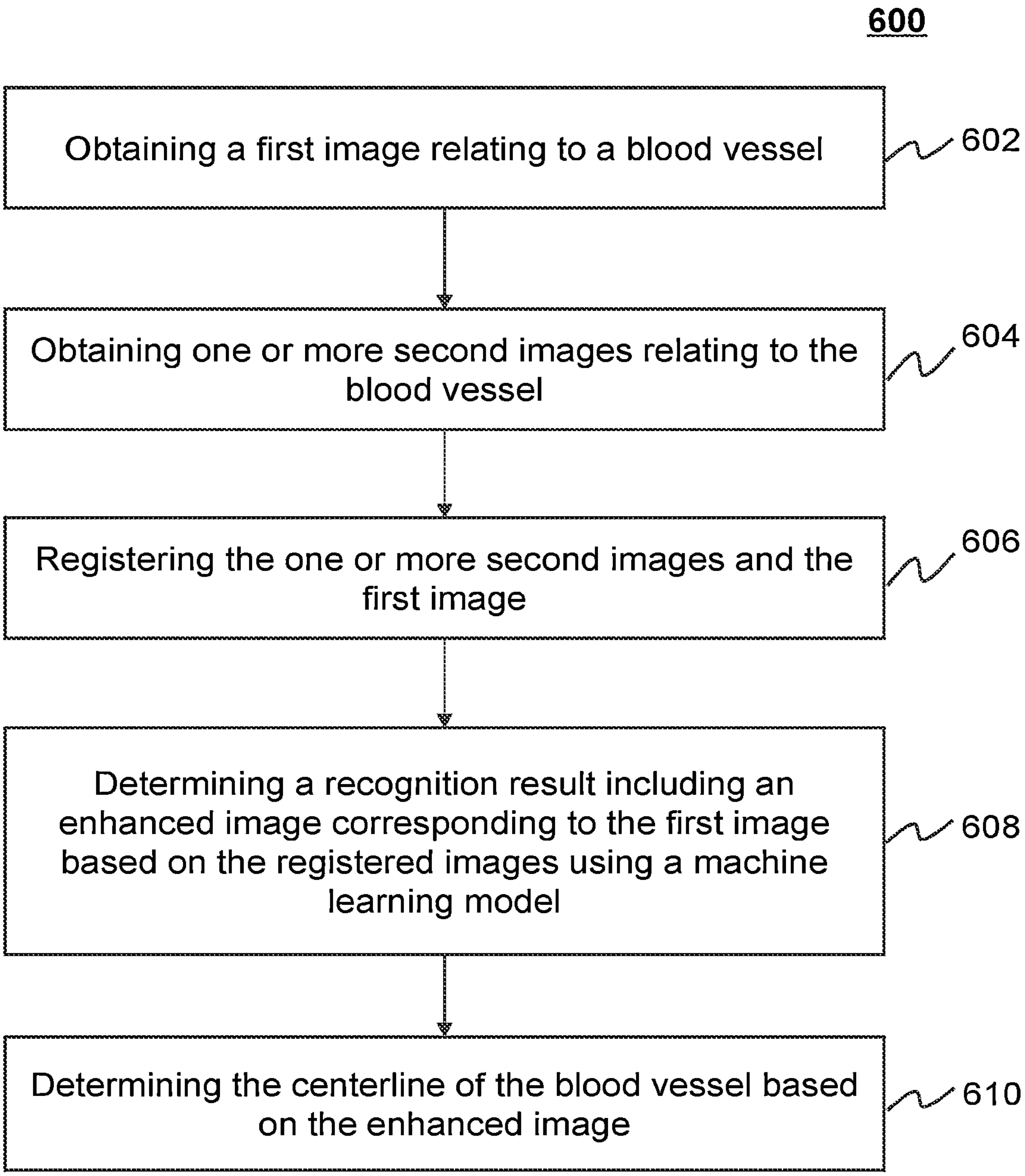
FIG. 6 is a flowchart illustrating an exemplary process for determining a centerline of a blood vessel according to some embodiments of the present disclosure.

FIG. 6 is a flowchart illustrating an exemplary process 600 for determining a centerline of a blood vessel according to some embodiments of the present disclosure. In some embodiments, process 600 may be implemented as a set of instructions (e.g., an application) stored in a storage device (e.g., the storage device 130, the storage 220, and/or the storage 390). The processing device 120A (e.g., the processor 210, the CPU 340, and/or one or more modules illustrated in FIG. 4A) may execute the set of instructions, and when executing the instructions, the processing device 120A may be configured to perform the process 600. The operations of the illustrated process presented below are intended to be illustrative. In some embodiments, the process 600 may be accomplished with one or more additional operations not described and/or without one or more of the operations discussed. Additionally, the order of the operations of process 600 illustrated in FIG. 6 and described below is not intended to be limiting.

In 602, the processing device 120A (e.g., the obtaining module 410) may obtain a first image relating to a blood vessel.

The first image relating to the blood vessel may be the same as or similar to that as described in operation 502 in FIG. 5 of the present disclosure. For example, the first image may be a 3D image acquired using a first imaging sequence (e.g., a dark blood imaging sequence, or a bright blood imaging sequence).

In 604, the processing device 120A (e.g., the obtaining module 410) may obtain one or more second images relating to the blood vessel.

The one or more second images relating to the blood vessel may be the same as or similar to that as described in operation 504 in FIG. 5. Each of the one or more second images may be a 3D image acquired using a second imaging sequence different from the first imaging sequence. For example, if the first imaging sequence is a dark blood imaging sequence, the second imaging sequence may be a bright blood imaging sequence or another dark blood imaging sequence. As another example, if the first imaging sequence is a bright blood imaging sequence, the second imaging sequence may be a dark blood imaging sequence or another bright blood imaging sequence. In some embodiments, different second images may be acquired using different second imaging sequences. For example, one second imaging sequence may be a first bright blood imaging sequence, and another second imaging sequence may be a second bright blood imaging sequence or a dark blood imaging sequence. As another example, one second imaging sequence may be a first dark blood imaging sequence, and another second imaging sequence may be a bright blood imaging sequence or a second dark blood imaging sequence. In some embodiments, each of the second image(s) may be acquired by a second imaging device. The second imaging device may be same as or different from a first imaging device that is used to acquire the first image relating to the blood vessel. For example, the first image may be acquired by an MRI device, and the one or more second images may be acquired by the MRI device or another MRI device. As another example, the first may be acquired by an MRI device, and the one or more second images may be acquired by a CT device. Alternatively, the one or more second images may be acquired by different second imaging devices (e.g., with different imaging modalities). In some embodiments, the acquisition of the one or more second images may be the same as or similar to the acquisition of the first image, which is not repeated herein.

In 606, the processing device 120A (e.g., the pre-processing module 450) may register the one or more second images and the first image.

In some embodiments, the first image and the one or more second images may be acquired at different time periods during which the subject may undergo different motions. Accordingly, the one or more second images and the first image may need to be registered with the first image. In some embodiments, the first image and the second image(s) may be 3D images, and the processing device 120A may directly register the 3D images. Alternatively, each of the 3D images may include a plurality of 2D images (or slices), and for each 2D image in the first image, the processing device 120A may register corresponding 2D image in the second image(s) and the each 2D image in the first image. In some embodiments, the processing device 120A may register the one or more second images and the first image using an image registration algorithm (e.g., a rigid registration algorithm or a non-rigid registration algorithm). Exemplary image registration algorithms may include a pixel-based registration algorithm, a feature based registration algorithm, a contour-based registration algorithm, a mutual information-based registration algorithm, or the like, or any combination thereof. In some embodiments, the first image may be designated as a reference image. The processing device 120A may register the one or more second images with the first image. Alternatively, the processing device 120A may designate an image acquired using a dark blood imaging sequence (e.g., a specific dark blood imaging sequence) in the first image and the one or more second images as a reference image, and register the remaining images with the reference image. As another example, the processing device 120A may designate an image acquired using a bright blood imaging sequence (e.g., a specific bright blood imaging sequence) in the first image and the one or more second images as a reference image, and register the remaining images with the reference image. The registration of multiple images may improve the efficiency and accuracy of the determination of the centerline.

In 608, the processing device 120A (e.g., the determination module 420) may determine a recognition result including a first enhanced image corresponding to the first image based on the registered images (e.g., the first image and the one or more registered second images, or a second image and the registered first image and one or more registered second images) using a machine learning model (i.e., the image recognition model, or the first machine learning model).

The image recognition model may refer to a process or an algorithm for determining a recognition result including at least an enhanced image corresponding to the image. More descriptions regarding the image recognition model may be found elsewhere in the present disclosure (e.g., operation 504 and the descriptions thereof).

In some embodiments, after registering each of the one or more second images and the first image, the processing device 120A may determine the first enhanced image by inputting the registered images (e.g., the first image and the one or more registered second images) into the image recognition model together. That is, the registered images (e.g., the first image and one or more registered second images) may be input into the image recognition model, and the image recognition model may output a recognition result including the first enhanced image corresponding to the first image. For example, if the first image is acquired using a dark blood imaging sequence, the processing device 120A may input the registered images (e.g., the first image and the one or more registered second images) in the image recognition model. The image recognition model may output a recognition result including a first enhanced image corresponding to the dark blood imaging sequence. As another example, if the first image is acquired using a bright blood imaging sequence, the processing device 120A may input the registered images (e.g., the first image and the one or more registered second images) into the image recognition model. The image recognition model may output a recognition result including a first enhanced image corresponding to the bright blood imaging sequence.

In some embodiments, after registering each of the one or more second images and the first image, the processing device 120A may determine a first candidate enhanced image by inputting the first image into the image recognition model. That is, the first image may be input into the image recognition model, and the image recognition model may output the first candidate enhanced image corresponding to the first image. The processing device 120A may further determine one or more second candidate enhanced images by inputting the one or more registered second images into the image recognition model, respectively. That is, each of the one or more registered second images may be input into the image recognition model respectively, and the image recognition model may output one second candidate enhanced image corresponding to the each of the one or more registered second images. In some embodiments, the processing device 120A may determine the first enhanced image by fusing the first candidate enhanced image and the one or more second candidate enhanced images. In some embodiments, the processing device 120A may fuse the first candidate enhanced image and the one or more second candidate enhanced images using an image fusion algorithm. Exemplary image fusion algorithms may include a fusion algorithm based on a weighted average, a fusion algorithm based on maximization (or minimization) of absolute values, a fusion algorithm based on principal component analysis (PCA), a fusion algorithm based on intensity, hue, and saturation (IHS), a pulse coupled neural network (PCNN) algorithm, a fusion algorithm based on pyramid transform, a fusion algorithm based on wavelet transform, a fusion algorithm based on multi-scale transform, a fusion algorithm based on contour wave transform, a fusion algorithm based on non-subsampled contourlet transform (NSCT), a fusion algorithm based on scale invariant feature transform (SIFT), a fusion algorithm based on shift invariant shearlet transform (SIST), or the like, or any combination thereof.

In 610, the processing device 120A (e.g., the determination module 420) may determine a centerline of the blood vessel based on the first enhanced image.

In some embodiments, the processing device 120A may determine at least two key points of the centerline based on the enhanced image. More descriptions regarding the determination of the at least two key points may be found elsewhere in the present disclosure. See, e.g., FIG. 8 and relevant descriptions thereof. The processing device 120A may further determine the centerline of the blood vessel based on the at least two key points and the first enhanced image. More descriptions regarding determining the centerline may be found elsewhere in the present disclosure. See, e.g., FIG. 7 and relevant descriptions thereof.

It should be noted that the above description regarding the process 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations of the process 600 may be omitted, and/or one or more additional operations may be added. For example, operation 606 may be omitted. That is, the processing device 120A may directly determine the enhanced image by inputting the first image and the one or more second images into the image recognition model without registration.

Figure 7:
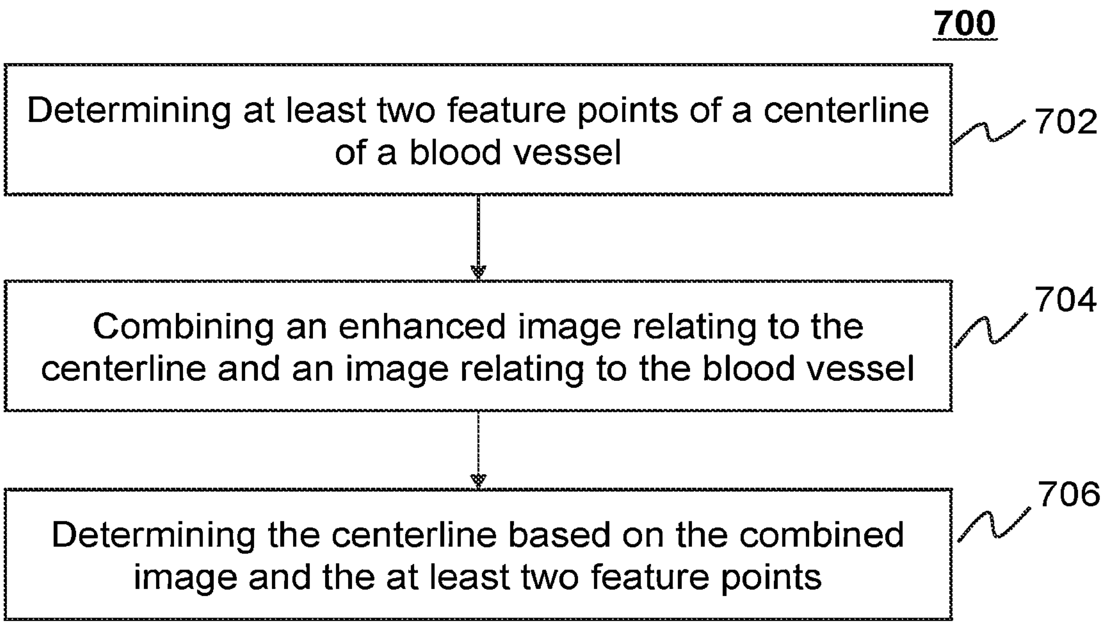
FIG. 7 is a flowchart illustrating an exemplary process for determining a centerline of a blood vessel according to some embodiments of the present disclosure.

FIG. 7 is a flowchart illustrating an exemplary process 700 for determining a centerline of a blood vessel according to some embodiments of the present disclosure. In some embodiments, process 700 may be implemented as a set of instructions (e.g., an application) stored in a storage device (e.g., the storage device 130, the storage 220, and/or the storage 390). The processing device 120A (e.g., the processor 210, the CPU 340, and/or one or more modules illustrated in FIG. 4A) may execute the set of instructions, and when executing the instructions, the processing device 120A may be configured to perform the process 700. The operations of the illustrated process presented below are intended to be illustrative. In some embodiments, the process 700 may be accomplished with one or more additional operations not described and/or without one or more of the operations discussed. Additionally, the order of the operations of process 700 illustrated in FIG. 7 and described below is not intended to be limiting. In some embodiments, one or more operations of the process 700 may be performed to achieve at least part of operation 506 in FIG. 5 or 610 in FIG. 6.

In 702, the processing device 120A (e.g., the determination module 420) may determine at least two key points of a centerline of a blood vessel.

As used herein, the key point(s) may include an endpoint of the centerline line (e.g., a starting point of the centerline, or an ending point of the centerline), an intersection point between the centerline and a centerline of another blood vessel, an inflection point of the centerline, or the like, or any combination thereof that can be used to determine the centerline of the blood vessel.

In some embodiments, the processing device 120A may determine at least two first initial key points, e.g., based on the experience of a user (e.g., a doctor, a technician, an operator, etc. of the image processing system 100). Each of the at least two first initial key points may correspond to one of the at least two key points. The experience of the user refers to the accumulated experience of the user to determine key points (e.g., a starting point, an ending point, an intersection point, an inflection point, etc.) on a centerline of a blood vessel. In some embodiments, the processing device 120A may directly designate the at least two first initial key points as the at least two key points. For example, the user may draw or identify at least two first initial key points in the image(s) (e.g., an enhanced image, the (registered) first image, the one or more (registered) second images), and the processing device 120A may obtain information of the at least two first initial key points and directly designate the at least two first initial key points as the at least two key points. In some embodiments, the processing device 120A may determine the at least two key points based on the at least two first initial key points and the first enhanced image, e.g., by performing a correction operation more details of which can be found elsewhere in the present disclosure (e.g., FIG. 8 and relevant descriptions thereof).

In some embodiments, alternatively or additionally, the processing device 120A may determine at least two second initial key points, e.g., using an image recognition model (e.g., the first image recognition model). Each of the at least two second initial key points may correspond to one of the at least two key points. The processing device 120A may further determine the at least two key points based on the at least two second initial key points and the first enhanced image, e.g., by performing a correction operation more details of which can be found elsewhere in the present disclosure (e.g., FIG. 8 and relevant descriptions thereof).

In some embodiments, the processing device 120A may not determine the first/second initial key points, and/or may not determine the key points based on the first/second initial key points. Since an enhanced image indicates path information of the centerline of the blood vessel, and the path information includes values of pixels, the at least two key points may include points (or pixels) with specific values. The processing device 120A may determine at least two regions in the first enhanced image. Each of the at least two regions may include at least one of the at least two key points. The at least two regions may include a starting region (e.g., a region including the starting point of the centerline), an ending region (e.g., a region including the ending point of the centerline), an intersection region (e.g., a region including the intersection point), etc. As described in connection with operation 504, each point of the centerline of the blood vessel in the first enhanced image may have a relatively large value (e.g., a grayscale value), and each pixel away from the centerline of the blood vessel may have a relatively small grayscale value. For each of the at least two regions, the processing device 120A may designate a pixel with the maximum grayscale value in the each region as one of the at least two key points.

In 704, the processing device 120A (e.g., the determination module 420) may combine an enhanced image relating to the centerline (e.g., the first enhanced image) and an image relating to the blood vessel (e.g., the first image).

The enhanced image relating to the centerline may be determined based on the first image as described elsewhere in the present disclosure. In some embodiments, the processing device 120A may combine the enhanced image relating to the centerline and the first image through a computing operation. The computing operation may include a multiply operation, a weighted multiply operation, an adding operation, a weighted adding operation, or the like, or any combination thereof. In some embodiments, the processing device 120A may further normalize the computed result to obtain the combined image. The combined image may include a 3D image.

Figure 11A:
FIGS. 11A and 11B are schematic diagrams illustrating different views of an exemplary combined image according to some embodiments of the present disclosure.
Figure 11B:
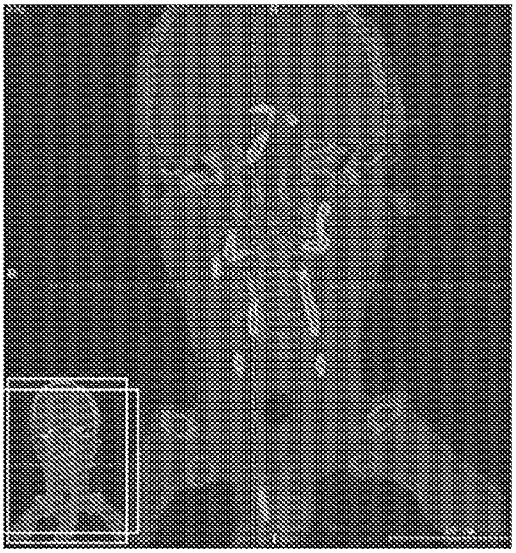

In some embodiments, the first enhanced image may indicate path information of at least a portion of the centerline of the blood vessel, e.g., one or more segments of the centerline of the blood vessel. That is, the information provided by the first enhanced image may be discontinuous and/or incomplete. Accordingly, the processing device 120A may combine the first enhanced image and the first image such that complete path information of the centerline can be provided, thereby improving the accuracy and efficiency of determining the centerline. For example, FIGS. 11A and 11B are schematic diagrams illustrating different views of an exemplary combined image according to some embodiments of the present disclosure. The combined image was generated by combining a CT image relating to a head and neck blood vessel of a patient and an enhanced image relating to a centerline of the head and neck blood vessel. FIG. 11A is a side view of the combined image. FIG. 11B is a front view of the combined image. According to the combined image, complete path information of the centerline of the head and neck blood vessel of the patient may be provided.

In 706, the processing device 120A (e.g., the determination module 420) may determine the centerline based on the combined image and the at least two key points.

In some embodiments, the processing device 120A may determine the centerline based on the combined image and the at least two key points using an algorithm. Exemplary algorithms may include a path planning algorithm, a minimum descent algorithm, a minimum spanning tree algorithm, or the like, or any combination thereof. For example, the at least two key points may include the starting point of the centerline and the ending point of the centerline. The processing device 120A may determine the centerline based on the starting point, the ending point, and the path information of the centerline using the path planning algorithm. Because the combined image provides complete path information of the centerline, the centerline determined based on the combined image may be complete and accurate. Therefore, an automatic determination of the centerline may be realized. In addition, in the determination of the centerline based on images acquired using different imaging sequences, various information of the blood vessel may be used. For instance, in an image acquired using a bright blood imaging sequence, a blood vessel can be presented without an interference of other tissues, but a plaque (if any) of the blood vessel cannot be displayed or distinguished. In an image acquired using a dark blood imaging sequence, the plaque of the blood vessel can be displayed noticeably, but the blood vessel cannot be distinguished from other tissues (e.g., an encephalocoele). The determination of the centerline using the image recognition model may take advantages of the images acquired using different sequences, thereby realizing an automatic and accurate determination of the centerline.

It should be noted that the above description regarding the process 700 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations of the process 700 may be omitted, and/or one or more additional operations may be added. For example, a storing operation may be added elsewhere in the process 700. In the storing operation, the processing device 120A may store information and/or data (e.g., the first initial key points, the second initial key points, the key points, the combined image, etc.) associated with the image processing system 100 in a storage device (e.g., the storage device 130) disclosed elsewhere in the present disclosure.

Figure 8:
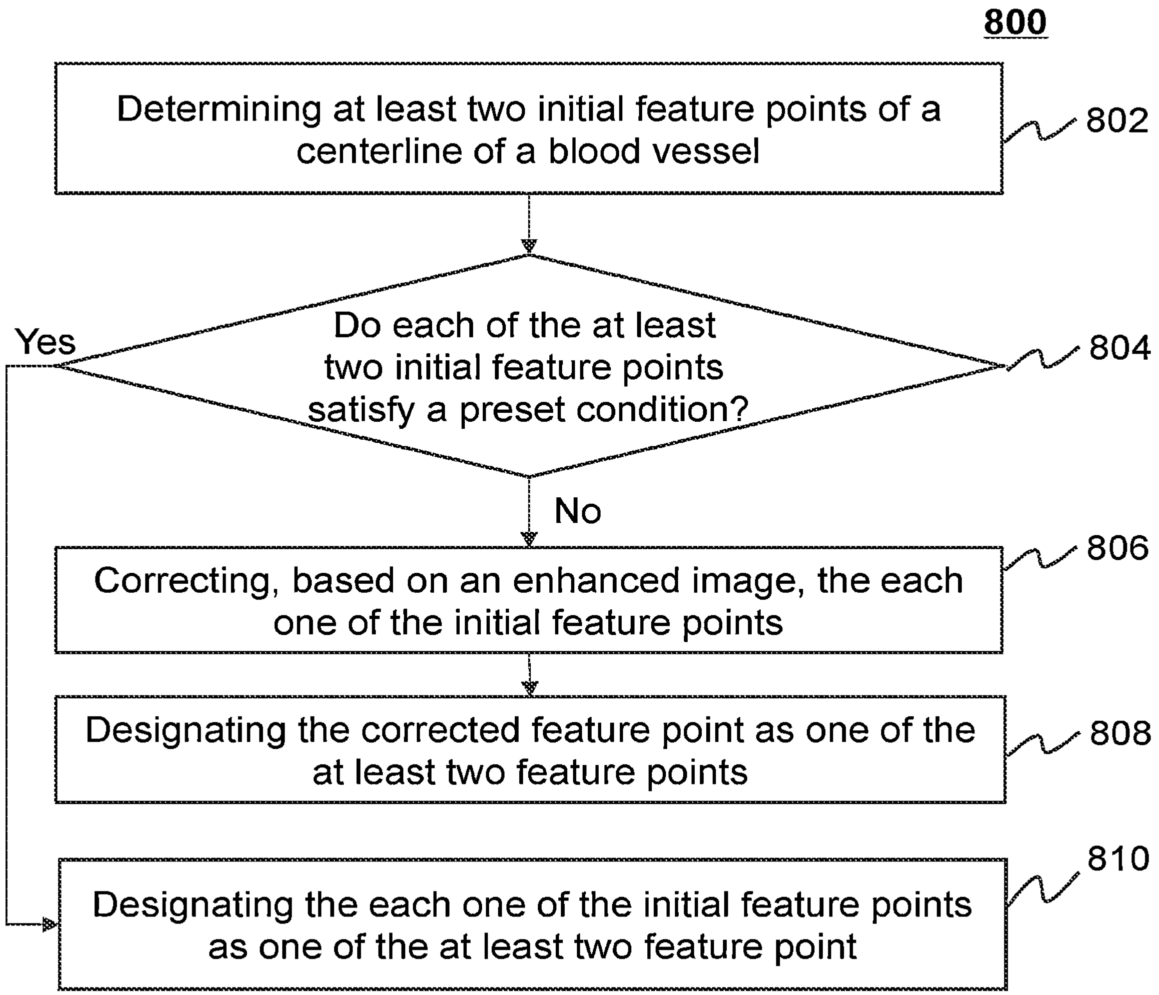
FIG. 8 is a flowchart illustrating an exemplary process for determining key points according to some embodiments of the present disclosure.

FIG. 8 is a flowchart illustrating an exemplary process 800 for determining key points according to some embodiments of the present disclosure. In some embodiments, process 800 may be implemented as a set of instructions (e.g., an application) stored in a storage device (e.g., the storage device 130, the storage 220, and/or the storage 390). The processing device 120A (e.g., the processor 210, the CPU 340, and/or one or more modules illustrated in FIG. 4A) may execute the set of instructions, and when executing the instructions, the processing device 120A may be configured to perform the process 800. The operations of the illustrated process presented below are intended to be illustrative. In some embodiments, the process 800 may be accomplished with one or more additional operations not described and/or without one or more of the operations discussed. Additionally, the order of the operations of process 800 illustrated in FIG. 8 and described below is not intended to be limiting. In some embodiments, one or more operations of the process 800 may be performed to achieve at least part of operation 702 as described in connection with FIG. 7.

In 802, the processing device 120A (e.g., the determination module 420) may determine at least two initial key points of a centerline of a blood vessel.

As described in connection with operation 702, the at least two initial key points may include at least two first initial key points, and/or at least two second initial key points, etc. The at least two first key points may be determined based on the experience of the user. For example, the user may determine the at least two first initial key points of the centerline, and send an instruction including information of the at least two initial key points to the processing device 120A. The instruction may include coordinates of the at least two first initial key points in the first enhanced image. The processing device 120A may determine the at least two first initial key points of the centerline based on the instruction. As another example, the user may determine the at least two first initial key points of the centerline through an interaction device such as a mouse, a keyboard, a touch pad, a display, etc. The processing device 120A may determine the at least two first initial key points via the interaction device.

In some embodiments, the at least two initial key points may be determined using a machine learning model (e.g., the image recognition model). For example, the processing device 120A may input the first image (and/or the one or more second images) into the image recognition model, and the image recognition model may output at least one enhanced image relating to the key points. In some embodiments, the processing device 120A may determine at least two first initial key points based on the first enhanced image. In some embodiments, the processing device 120A may determine the at least two second initial key points based on the at least one enhanced image relating to the key points (e.g., the second enhanced image(s)).

In 804, the processing device 120A (e.g., the determination module 420) may determine, based on an enhanced image (i.e., the first enhanced image), whether each of the at least two initial key points satisfies a preset condition. In response to determining that the each of the at least two initial key points does not satisfy the preset condition, the processing device 120A may proceed to operation 806 (i.e., correct the each of the at least two initial key points). Alternatively, in response to determining that the each of the at least two initial key points satisfies the preset condition, the processing device 120A may proceed to operation 810 (i.e., designate the each of the at least two initial key points as one of the at least two key points).

As used herein, the preset condition may indicate that a point is in a region where the centerline of the blood vessel is located. The preset condition may be related to a pixel value of a point, a coordinate of a point, etc. For example, the preset condition may include that each key point is in a preset region, each key point is in a centerline region, a pixel value of each key point satisfies a pixel value requirement, or the like, or any combination thereof. As used herein, the preset region refers to a region around a key point. The centerline region may include the centerline and a region around the centerline.

In some embodiments, the processing device 120A may determine the preset region in the first enhanced image (e.g., according to the experience of the user), which is similar to the determination of the at least two regions as described in operation 702. For example, the preset region may be determined based on an order of different tissues of a body structure, a location relation between different points of a blood vessel structure, etc. The preset region may include possible pixels belonging to the key points in the first enhanced image. Further, the processing device 120A may determine whether each of the at least two initial key points is in a preset region based on a coordinate of the each initial key point. In response to determining that the each initial key point is not in the preset region, the process 800 may proceed to operation 806. In response to determining that the each initial key point is in the preset region, the processing device 120A may determine whether each of the at least two initial key points is in a centerline region based on the coordinate of the each initial key point. In response to determining that the each initial key point is not in the centerline region, the process 800 may proceed to operation 806. In response to determining that the each initial key point is in the centerline region, the process may proceed to operation 810.

In some embodiments, the processing device 120A may identify the centerline region based on the first enhanced image. The centerline region may include the centerline and be larger than the centerline. For example, the processing device 120A may determine the centerline region based on pixels of the first enhanced image whose pixel values are greater than a first preset pixel value. In some embodiments, the processing device 120A may directly determine whether the each initial key point is in the centerline region without determining whether the each initial key point is in the preset region.

In some embodiments, in response to determining that the each initial key point is in the centerline region, the processing device 120A may further compare a pixel value of the each initial key point with pixel values in the centerline region instead of directly proceeding the process 800 to operation 810. For example, the processing device 120A may determine whether a first difference between the pixel value of the each initial key point and a maximum pixel value in the centerline region is less than a first threshold. In response to determining that the first difference is less than the first threshold, the process 800 may proceed to operation 810. In response to determining that the first difference is larger than the first threshold, the process 800 may proceed to operation 806.

In some embodiments, the processing device 120A may directly determine a pixel value threshold based on the first enhanced image. The processing device 120A may determine whether the preset condition is satisfied based on the pixel value threshold and the pixel value of the each initial key point. For example, the processing device 120A may determine a maximum pixel value in the first enhanced image as the pixel value threshold. The processing device 120A may determine whether a third difference between the pixel value of the each initial key point and the pixel value threshold is less than a third threshold. In response to determining that the third difference is less than the third threshold, the process 800 may proceed to operation 810. In response to determining that the third difference is larger than the third threshold, the process 800 may proceed to operation 806.

In 806, in response to determining that the each one of the initial key points does not satisfy the preset condition, the processing device 120A (e.g., the determination module 420) may correct, based on the enhanced image (e.g., the first enhanced image), the each one of the initial key points.

In some embodiments, the processing device 120A may correct the each one of the initial key points based on experience(s) of the user. For example, the user may modify the at least two initial key points of the centerline of the blood vessel. In some embodiments, the processing device 120A may correct the each one of the initial key points based on a correction algorithm. Exemplary correction algorithms may include a spatial transformation algorithm, a sharding correction algorithm, a Gopfert algorithm, a gray interpolation algorithm, or the like, or any combination thereof. It should be noted that the above correction algorithms are merely provided for the purposes of illustration, and not intended to limit the scope of the present disclosure. In some embodiments, the processing device 120A may terminate the correction of the each one of the initial key points until the preset condition is satisfied.

In 808, the processing device 120A (e.g., the determination module 420) may designate the corrected key point as one of the at least two key points.

The corrected key point may satisfy the preset condition. Accordingly, the processing device 120A may designate the corrected key point as one of the at least two key points.

In 810, in response to determining that the each one of the initial key points satisfies the preset condition, the processing device 120A (e.g., the determination module 420) may designate the each one of the initial key points as one of the at least two key points.

The processing device 120A may further determine the centerline of the blood vessel based on the first enhanced image and the at least two key points.

It should be noted that the above description regarding the process 800 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations of the process 800 may be omitted, and/or one or more additional operations may be added. For example, operations 806 and 808 may be omitted. That is, in response to determining that each of the at least two initial key points does not satisfy the preset condition, the processing device 120 may proceed to operation 802 (i.e., determine other initial key point(s)).

Figure 9:
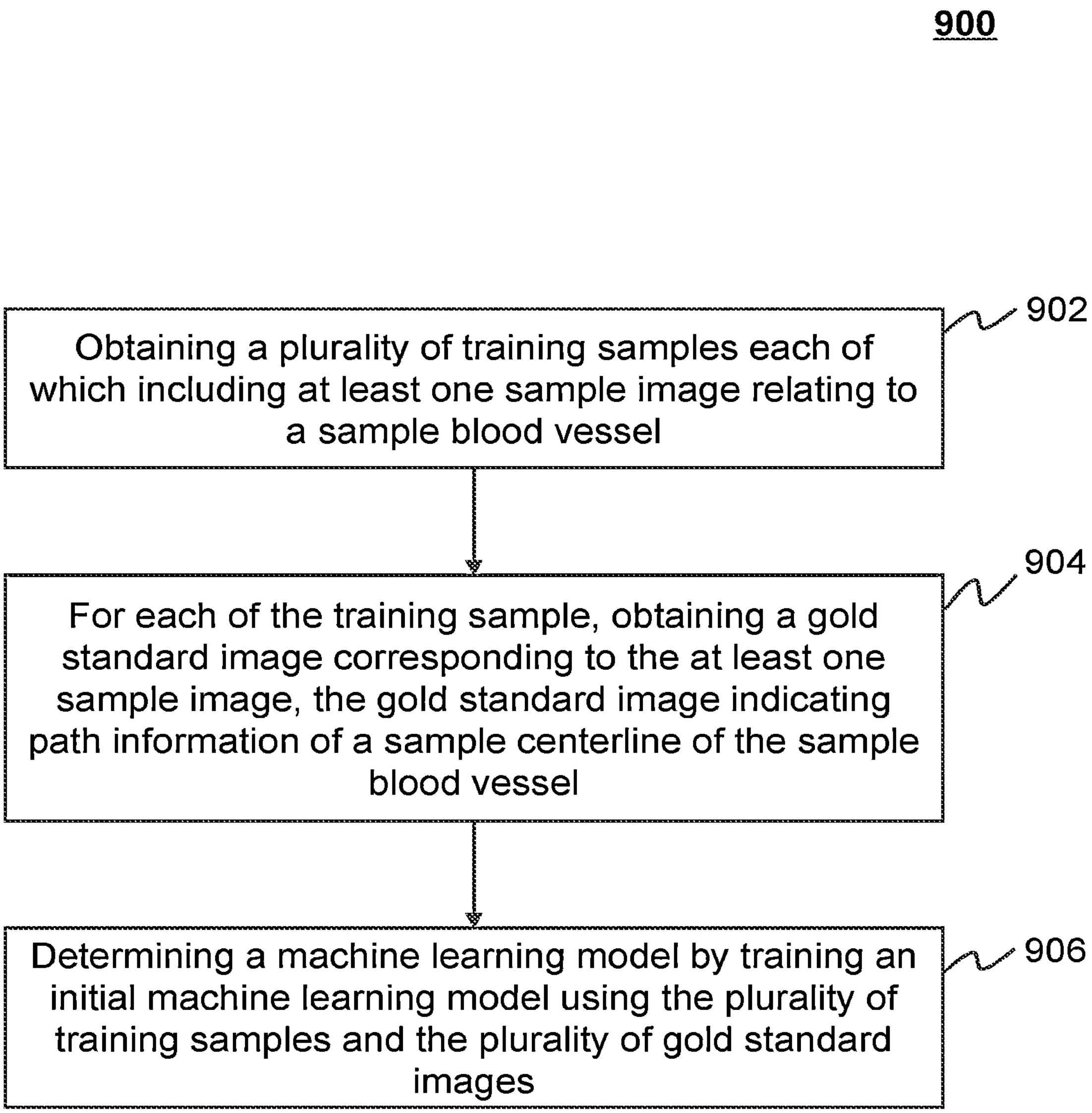
FIG. 9 is a flowchart illustrating an exemplary process for generating an image recognition model according to some embodiments of the present disclosure.

FIG. 9 is a flowchart illustrating an exemplary process 900 for generating an image recognition model according to some embodiments of the present disclosure. In some embodiments, the process 900 may be implemented as a set of instructions (e.g., an application) stored in a storage device (e.g., the storage device 130, storage 220, and/or storage 390). The processing device 120B (e.g., the processor 210, the CPU 340, and/or one or more modules illustrated in FIG. 4B) may execute the set of instructions, and when executing the instructions, the processing device 120B may be configured to perform the process 900. The operations of the illustrated process presented below are intended to be illustrative. In some embodiments, the process 900 may be accomplished with one or more additional operations not described and/or without one or more of the operations discussed. Additionally, the order of the operations of process 900 illustrated in FIG. 9 and described below is not intended to be limiting. In some embodiments, the image recognition model described in FIGS. 5-8 may be obtained according to the process 900. In some embodiments, the process 900 may be performed by another device or system other than the image processing system 100, e.g., a device or system of a vendor or a manufacturer. For illustration purposes, the implementation of the process 900 by the processing device 120B is described as an example.

In 902, the processing device 120B (e.g., the obtaining module 460) may obtain a plurality of training samples. Each of the plurality of training samples may include at least one sample image relating to a sample blood vessel.

A type of the sample blood vessel may be the same as or different from a type of the blood vessel as described in connection with FIG. 5. For example, if the image recognition model is used to perform enhanced image determination on an image relating to a blood vessel, the sample blood vessel may be of a type that is the same as or different from the type of the blood vessel. The sample image relating to the sample blood vessel refers to an image including the sample blood vessel. In some embodiments, a type of the sample image may be the same as a type of the first image. That is, the sample image and the first image may be acquired by a same type of imaging device (e.g., a CT device, an MRI device, etc.) and/or using a same imaging sequence. For example, if the first image is acquired using a black imaging sequence, the sample image may be acquired using the black imaging sequence. As another example, if the first image is acquired using a bright imaging sequence, the sample image may be acquired using the bright blood imaging sequence. In some embodiments, if the image recognition model to be trained includes multiple inputs (e.g., the first image and the one or more second images), the at least one sample image may include multiple sample images, e.g., acquired using different imaging sequences. It should be noted that the above imaging sequences are merely provided for the purposes of illustration, and not intended to limit the scope of the present disclosure. In some embodiments, the obtaining of the at least one sample image may be the same as or similar to the obtaining of the first image as described in 502 and/or 602, which is not repeated herein.

In some embodiments, the training samples (or a portion thereof) may need to be preprocessed before being used in training the image recognition model. For example, for a training sample, the processing device 120B may perform image resizing, image resampling, and image normalization on the sample image relating to the sample blood vessel.

In 904, for each of the plurality of training samples, the processing device 120B (e.g., the obtaining module 460) may obtain a gold standard image corresponding to the at least one sample image. The gold standard image may indicate path information of a sample centerline of the sample blood vessel. The gold standard image corresponding the at least one sample image may also be referred to as a first gold standard image relating to a sample centerline of the sample blood vessel.

In some embodiments, for each training sample, the first gold standard image may be obtained based on at least one labeled sample image relating to the sample blood vessel. For example, a user (e.g., a doctor, a technician, an operator) may manually label a sample centerline in each of the at least one sample image. The processing device 120B may determine a first gold standard image relating to the sample centerline based on the at least one labeled sample image. As another example, the processing device 120B may obtain at least two sample key points of the sample centerline (e.g., according to a user instruction). The processing device 120B may determine the sample centerline based on the at least two sample key points and the sample image. The processing device 120B may determine the first gold standard image based on the determined sample centerline.

Figure 11C:
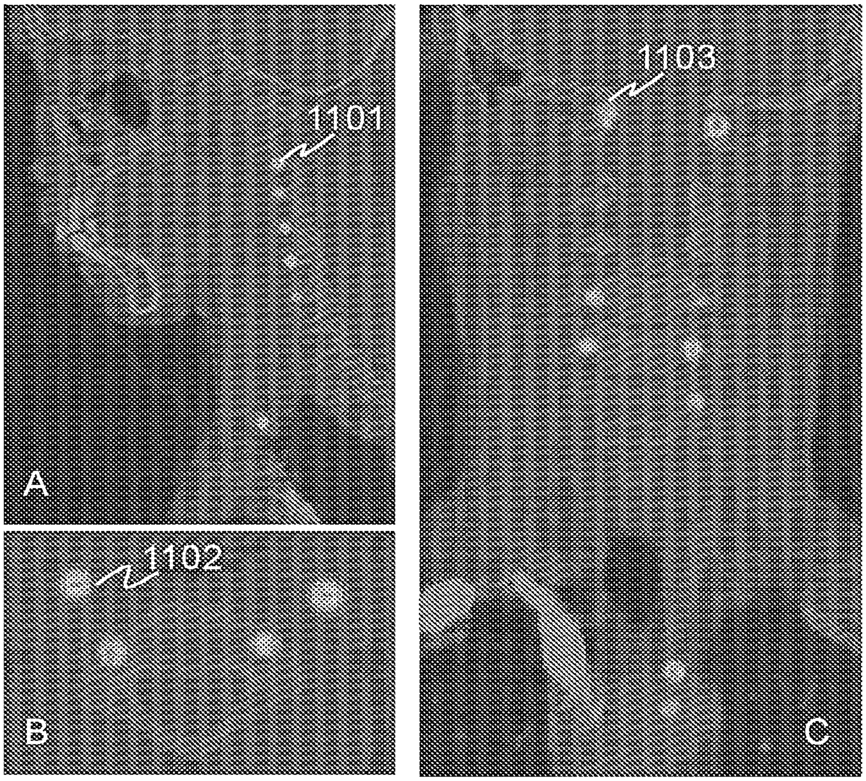
FIG. 11C is a schematic diagram illustrating exemplary Gaussian kernels according to some embodiments of the present disclosure.

In some embodiments, the processing device 120B may determine the first gold standard image by superimposing a plurality of Gaussian kernels corresponding to a plurality of points of the sample centerline. For each point of the sample centerline, the processing device 120B may determine a Gaussian kernel centered at the point. The further a point in the Gaussian kernel away from the center point of the Gaussian kernel, the greater a difference between a value of the point and a value of the center point of the Gaussian kernel. For example, the value of the center point may be maximum among points in the Gaussian kernel. In some embodiments, a size of the Gaussian kernel may be determined based on a size of the sample blood vessel. The larger the size of the sample blood vessel is, the larger the size of the Gaussian kernel may be. For example, for a point of a sample blood vessel of the head, the processing device 120B may determine a size of a Gaussian kernel corresponding to the point as 5. Referring to FIG. 11C, FIG. 11C is a schematic diagram illustrating exemplary Gaussian kernels according to some embodiments of the present disclosure. As shown in FIG. 11C, an image A is a side view of a CT image of a sample blood vessel of the sample head and neck and includes a plurality of Gaussian kernels 1101, an image B is a front view of a lower portion of the CT image and includes a plurality of Gaussian kernels 1102, and an image C is a front view of the CT image includes a plurality of Gaussian kernels 1103.

In some embodiments, during the superimposing of the plurality of Gaussian kernels, a portion of the plurality of Gaussian kernels may be overlapped. For a point that corresponds to one or more overlapped Gaussian kernels, the processing device 120B may determine one of values of the point in the one or more overlapped Gaussian kernels as a value of the point in the first gold standard image. For example, for the point corresponds to one or more overlapped Gaussian kernels, the processing device 120B may determine a maximum value of the values of the point in the one or more overlapped Gaussian kernels as the value of the point in the first gold standard image. Therefore, each point of the sample centerline may have a maximum value in the first gold standard image. The further a point away from the points of the sampled centerline, the less a value of the point may be. By superimposing the plurality of Gaussian kernels corresponding to the plurality of points of the sample centerline to determine the first gold standard image, the trained image recognition model may output an enhanced image quickly and accurately. In addition, the enhanced image may include enough path information to determine a centerline of a blood vessel.

In some embodiments, the processing device 120B may label a type of training samples among the plurality of the training samples. For example, the processing device 120B may label training samples including sample images acquired using a specific dark blood imaging sequence. Other training samples including sample images acquired using a bright blood imaging sequence or other dark blood imaging sequence(s) may be registered to the labeled training samples including the images acquired using the specific dark blood imaging sequence.

In some embodiments, if the image recognition model to be trained includes multiple outputs (e.g., the first enhanced image relating to the centerline and the second enhanced image relating to the at least two key points), the processing device 120B may determine multiple gold standard images, e.g., including the first gold standard image and a second gold standard image relating to at least two sample key points. For example, for each of the plurality of training samples, the processing device 120B may obtain a second gold standard image corresponding to the at least one sample image. The second gold standard image may indicate information of at least two sample key points of the sample centerline of the sample blood vessel. In some embodiments, the second gold standard image may be obtained by labeling the sample image relating to the sample blood vessel. For example, the user (e.g., a doctor, a technician, an operator) may manually label a sample image relating to the sample blood vessel to obtain the second gold standard image. As another example. the processing device 120B may automatically determine sample key point(s) of the sample centerline of the sample blood vessel in a sample image relating to the sample blood vessel and/or label the sample image based on the sample key point(s) to obtain the second gold standard image.

In 906, the processing device 120B (e.g., the model training module 470) may determine the machine learning model (i.e., the image recognition model) by training an initial machine learning model using the plurality of training samples and the plurality of first gold standard images (and/or the plurality of second gold standard images).

In some embodiments, the initial machine learning model may be an initial model (e.g., a machine learning model) before being trained. Exemplary initial machine learning models may include a convolutional neural network (CNN) model, a generative adversarial network (GAN) model, or any other suitable type of model. Exemplary CNN models may include a Fully Convolutional Network, such as a V-NET model, a U-NET model, etc. Exemplary GAN models may include a pix2pix model, a Wasserstein GAN (WGAN) model, a circle GAN model, etc.

In some embodiments, the initial machine learning model may include a multi-layer structure. For example, the initial machine learning model may include an input layer, an output layer, and one or more hidden layers between the input layer and the output layer. In some embodiments, the hidden layers may include one or more convolution layers, one or more rectified-linear unit layers (ReLU layers), one or more pooling layers, one or more fully connected layers, or the like, or any combination thereof. As used herein, a layer of a model refers to an algorithm or a function for processing input data of the layer. Different layers may perform different kinds of processing on their respective input. A successive layer may use output data from a previous layer of the successive layer as input data. In some embodiments, the convolutional layer may include a plurality of kernels, which may be used to extract a feature. In some embodiments, each kernel of the plurality of kernels may filter a portion (i.e., a region). The pooling layer may take an output of the convolutional layer as an input. The pooling layer may include a plurality of pooling nodes, which may be used to sample the output of the convolutional layer, so as to reduce the computational load of data processing and accelerate the speed of data processing speed. In some embodiments, the size of the matrix representing the inputted data may be reduced in the pooling layer. The fully connected layer may include a plurality of neurons. The neurons may be connected to the pooling nodes in the pooling layer. In the fully connected layer, a plurality of vectors corresponding to the plurality of pooling nodes may be determined based on a training sample, and a plurality of weighting coefficients may be assigned to the plurality of vectors. The output layer may determine an output based on the vectors and the weighting coefficients obtained from the fully connected layer.

In some embodiments, each of the layers may include one or more nodes. In some embodiments, each node may be connected to one or more nodes in a previous layer. The number (or count) of nodes in each layer may be the same or different. In some embodiments, each node may correspond to an activation function. As used herein, an activation function of a node may define an output of the node given input or a set of inputs. In some embodiments, each connection between two of the plurality of nodes in the initial machine learning model may transmit a signal from one node to another node. In some embodiments, each connection may correspond to a weight coefficient. A weight coefficient corresponding to a connection may be used to increase or decrease the strength or impact of the signal at the connection.

The initial machine learning model may include one or more model parameters, such as architecture parameters, learning parameters, etc. In some embodiments, the initial machine learning model may only include a single model. For example, the initial machine learning model may be a CNN model and exemplary model parameters of the preliminary model may include the number (or count) of layers, the number (or count) of kernels, a kernel size, a stride, a padding of each convolutional layer, a loss function, or the like, or any combination thereof. Before training, the model parameter(s) of the initial machine learning model may have their respective initial values. For example, the processing device 120B may initialize parameter value(s) of the model parameter(s) of the initial machine learning model.

In some embodiments, the initial machine learning model may be trained according to a machine learning algorithm as described elsewhere in this disclosure (e.g., FIG. 5 and the relevant descriptions). For example, the processing device 120B may generate the image recognition model according to a supervised machine learning algorithm by performing one or more iterations to iteratively update the model parameter(s) of the initial machine learning model.

In some embodiments, for the image recognition model to be trained including a single output, for each of the plurality of training samples, the processing device 120B may generate an estimated first gold standard image by applying an updated machine learning model determined in a previous iteration. During the application of the updated machine learning model on a training sample, the updated machine learning model may be configured to receive a sample image related to a sample blood vessel. The estimated first gold standard image may be an output of the updated machine learning model.

In some embodiments, the processing device 120B (e.g., the model training module 470) may determine, based on the estimated first gold standard image and a corresponding first gold standard image of the each training sample, a first assessment result of the updated machine learning model.

The first assessment result may indicate an accuracy and/or efficiency of the updated image recognition model. In some embodiments, the processing device 120B may determine the first assessment result by assessing a loss function that relates to the updated image recognition model. For example, a value of a loss function may be determined to measure a difference between the estimated first gold standard image and the first gold standard image of the each training sample. The processing device 120B may determine the first assessment result based on the value of the loss function. As another example, the processing device 120B may determine an overall value of the loss function according to a function (e.g., a sum, a weighted sum, etc.) of the values of the loss functions of the training samples. The processing device 120B may determine the first assessment result based on the overall value. Additionally or alternatively, the first assessment result may be associated with the amount of time it takes for the updated image recognition model to generate the estimated first gold standard image of each training sample. For example, the shorter the amount of time is, the more efficient the updated image recognition model may be. In some embodiments, the processing device 120B may determine the first assessment result based on the value relating to the loss function(s) aforementioned and/or the efficiency.

In some embodiments, the first assessment result may include a determination as to whether a first termination condition is satisfied in the current iteration. In some embodiments, the first termination condition may relate to the value of the overall loss function. For example, the first termination condition may be deemed satisfied if the value of the overall loss function is minimal or smaller than a threshold (e.g., a constant). As another example, the first termination condition may be deemed satisfied if the value of the overall loss function converges. In some embodiments, convergence may be deemed to have occurred if, for example, the variation of the values of the overall loss function in two or more consecutive iterations is equal to or smaller than a threshold (e.g., a constant), a certain count of iterations has been performed, or the like. Additionally or alternatively, the first termination condition may include that the amount of time it takes for the updated image recognition model to generate the estimated first gold standard image of each training sample is smaller than a threshold.

In some embodiments, for the image recognition model to be trained including multiple outputs (e.g., the first enhanced image relating to the centerline and the second enhanced image relating to the at least two key points of the centerline), the processing device 120B may determine the image recognition model by training the initial machine learning model using the plurality of training samples, the plurality of first gold standard images, and the plurality of second gold standard images. For each of the plurality of training samples, the processing device 120B may generate an estimated first gold standard image and an estimated second gold standard image by applying an updated machine learning model determined in a previous iteration. During the application of the updated machine learning model on a training sample, the updated machine learning model may be configured to receive the at least one sample image related to a sample blood vessel. The estimated first gold standard image and the estimated second gold standard image may be outputs of the updated machine learning model.

In some embodiments, the processing device 120B may determine, based on the estimated first gold standard image, a first gold standard image, the estimated second gold standard image, and a second gold standard image of each training sample, a second assessment result of the updated machine learning model.

The second assessment result may relate to a second loss function. The second loss function may include a loss function of mean square error. The mean square error refers to an error between the estimated first gold standard image and a first gold standard image of each training sample and/or an error between the estimated second gold standard image and the second gold standard image of each training sample. The second loss function may be associated with a first weight relating to the plurality of sample centerlines and a second weight relating to the plurality of sample key points. The second weight may be greater than the first weight (e.g., a ratio of the second weight to the first weight may be 20:1). The first weight and/or the second weight may be determined according to a count (or number) of the plurality of sample key points. In some embodiments, the processing device 120B may determine a first difference between the first estimated gold standard image and the first gold standard image. The processing device 120B may determine a second difference between the estimated second gold standard image and the second gold standard image. The processing device 120B may determine the second loss function based on the first difference and the second difference, e.g., by determining a weighted sum of the first difference and the second difference. A weight of the first difference may be the first weight, and a weight of the second difference may be the second weight. In some embodiments, the second assessment result may include a determination as to whether a second termination condition is satisfied in the current iteration. For example, if the second loss function is less than a threshold, the second termination condition may be satisfied in the current iteration. Alternatively, the second termination condition may be similar to the first termination condition, which is not repeated herein.

In some embodiments, in response to a determination that the termination condition is satisfied, the processing device 120B may designate the updated machine learning model as the image recognition model. Accordingly, the image recognition model may be generated. In response to a determination that the termination condition is not satisfied, the processing device 120B may continue to perform operation 906, in which the processing device 120B or an optimizer may update parameter values (or a portion thereof) of the updated machine learning model to be used in a next iteration based on the assessment result (e.g., the first assessment result and/or the second assessment result).

It should be noted that the above description regarding process 900 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be added or omitted. For example, the image recognition model may be stored in a storage device (e.g., the storage device 130) disclosed elsewhere in the present disclosure for further use. As another example, after the image recognition model is generated, the processing device 120B may further test the image recognition model using a set of testing images. Additionally or alternatively, the processing device 120B may update the image recognition model periodically or irregularly based on one or more newly-generated training images (e.g., new sample images, new first gold standard images, and/or new second gold standard images).

FIGS. 10A-10H are schematic diagrams illustrating exemplary structures of image recognition models according to some embodiments of the present disclosure.

Figure 10A:
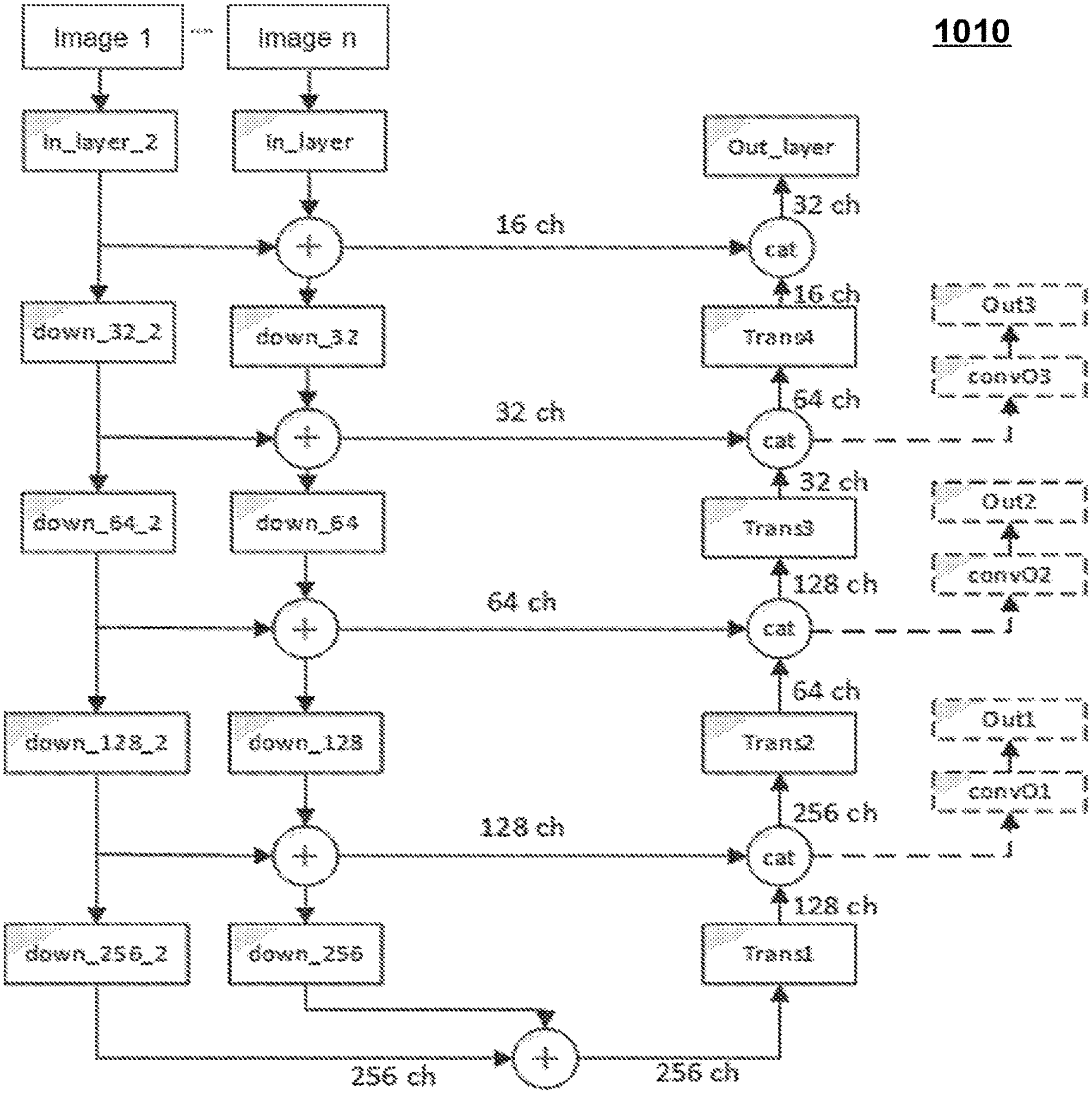
FIGS. 10A-10H are schematic diagrams illustrating exemplary structures of image recognition models according to some embodiments of the present disclosure.
Figure 10B:
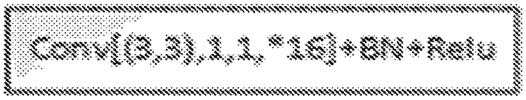
Figure 10C:
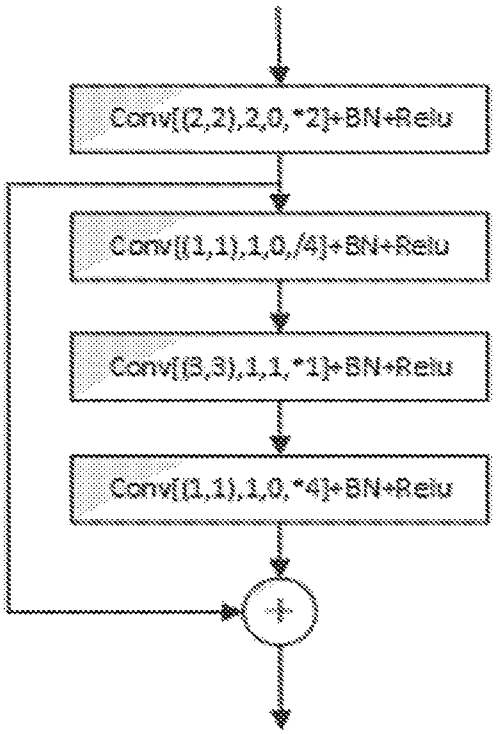
Figure 10D:
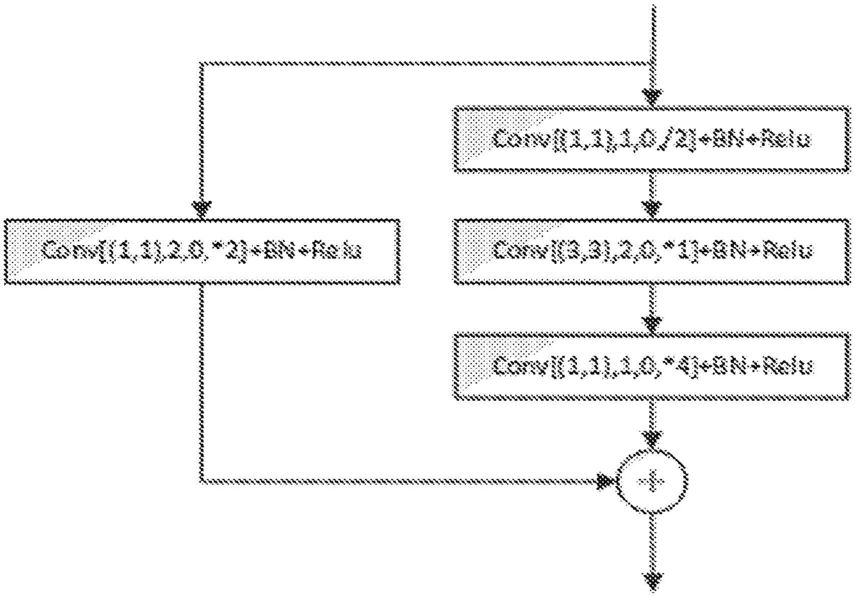
Figure 10E:
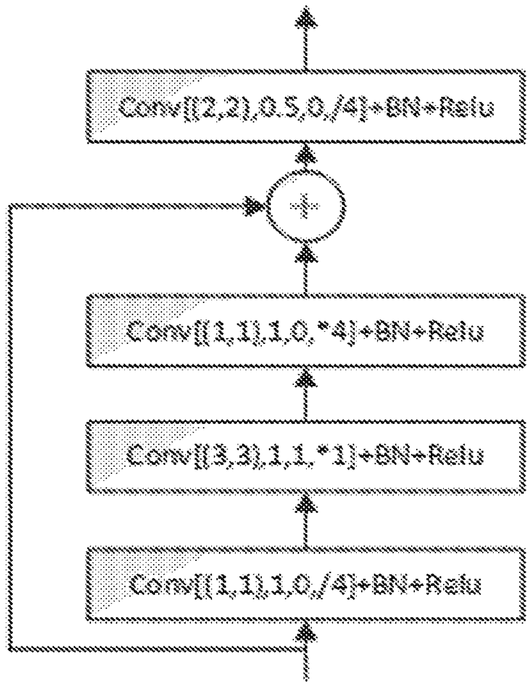
Figure 10F:
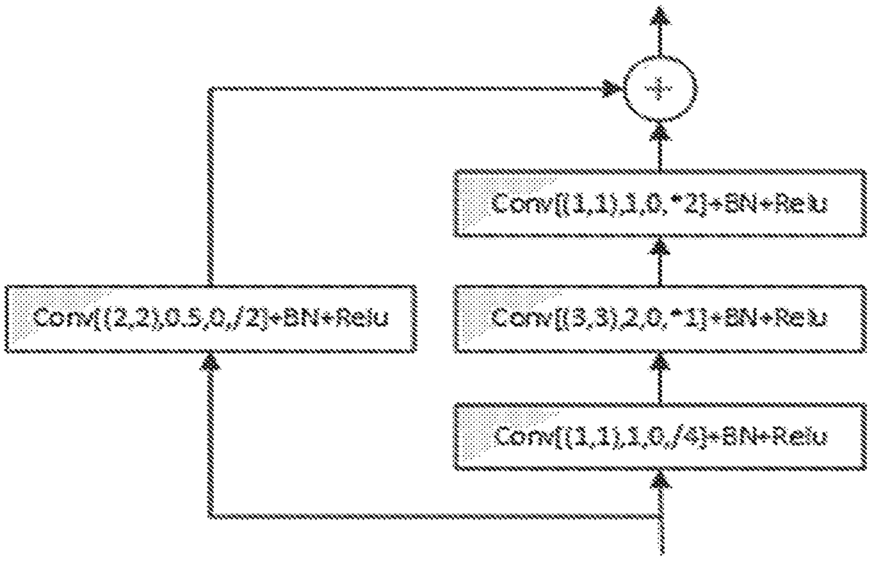
Figure 10G:
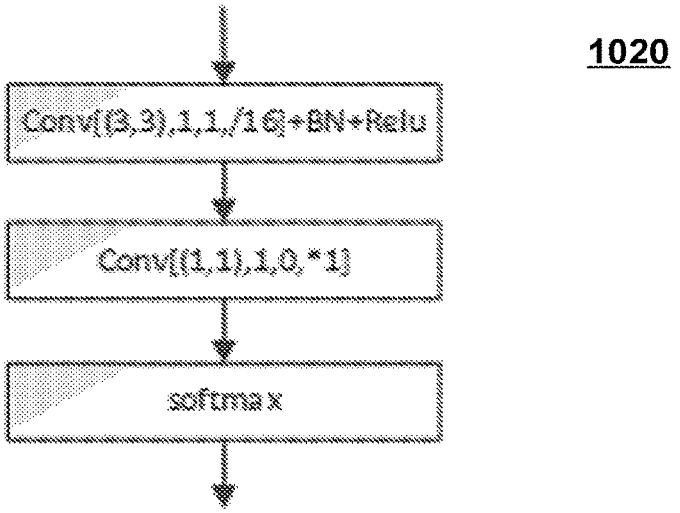

As shown in FIG. 10A, an image recognition model 1010 is a VNET convolutional neural network. The image recognition model 1010 includes a down-sampling network and an up-sampling network. The down-sampling network includes one or more input layers and multiple down-sampling layers. The up-sampling network includes multiple up-sampling layers, multiple splicing layers, and an output layer. An exemplary structure of the input layer (i.e., "in_layer") is shown in FIG. 10B. An exemplary structure of the down-sampling layer (i.e., "down_layer") is shown in FIG. 10C or FIG. 10D. An exemplary structure of the up-sampling layer (i.e., "Trans (also referred to as up_layer)") is shown in FIG. 10E or FIG. 10F. An exemplary structure of the output layer (i.e., "out_layer") is shown in FIG. 10G. A process for determining a recognition result from image 1 to image n using the image recognition model 1010 includes the following operations. The registered images 1 to n are input into the "in_layer" of the down-sampling network of each branch, respectively. Each "in_layer" outputs an intermediate image of its corresponding image. Then, the intermediate image is input into a "down_layer" connected by each "in_layer" for a down-sampling processing. The image after the down-sampling processing is input into a splicing layer (a cat layer) and a "Trans" connected by each "in_layer" for an up-sampling processing. Finally, recognition results of the blood vessel based on the images 1 to n are output by the "out_layer". That is, the enhanced image relating to the centerline of the blood vessel and/or the (initial) key points of the centerline of the blood vessel is output. The dotted line in FIG. 10A are relay supervision layers. The image recognition model 1010 may or may not include the relay supervision layers.

Figure 10H:
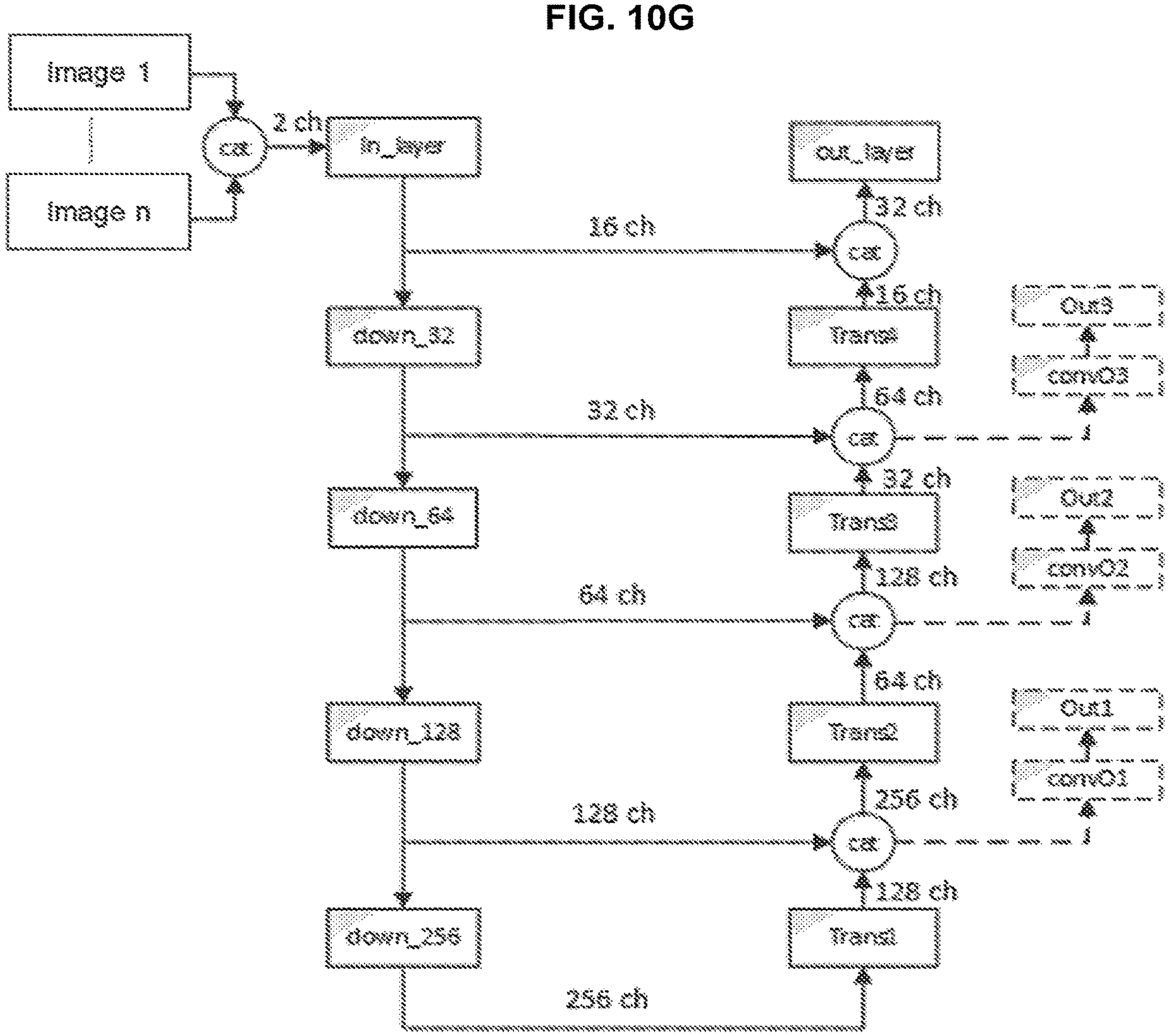

As shown in FIG. 10H, an image recognition model 1020 is also a VNET convolutional neural network. The image recognition model 1020 includes a down-sampling network and an up-sampling network. The down-sampling network includes one or more input layers and multiple down-sampling layers. The up-sampling network includes multiple up-sampling layers, multiple splicing layers, and an output layer. As used herein, structures of the input layer, the down-sampling layer, the up-sampling layer, and the output layer are the same as or similar to the structures of the input layer, the down-sampling layer, the up-sampling layer, and the output layer in the image recognition model 1010, which may not be repeated herein. A process for determining a recognition result from image 1 to image n using the image recognition model 1020 includes the following operations. The registered images 1 to n are input into the "in_layer" of the down-sampling network of each branch, respectively. Each "in_layer" outputs an intermediate image of its corresponding image. Then, the intermediate image is input into a "down_layer" connected by each "in_layer" for a down-sampling processing. The image after the down-sampling processing is input into a splicing layer (a cat layer) and a "Trans" connected by each "in_layer" for an up-sampling processing. Finally, recognition results of the blood vessel based on the images 1 to n are output by the "out_layer". That is, the enhanced image relating to the centerline of the blood vessel and/or the (initial) key points of the centerline of the blood vessel is output. The dotted line in FIG. 10H indicates a relay supervision. The image recognition model may or may not include the relay supervision. Optionally, the "out_layer" can output only the enhanced image relating to the centerline of the blood vessel, and a convolution layer may be added later to output the (initial) key points of the centerline of the blood vessel.

FIG. 12 is a flowchart illustrating an exemplary process 1200 for displaying CPR images and MPR images according to some embodiments of the present disclosure. In some embodiments, process 1200 may be implemented as a set of instructions (e.g., an application) stored in a storage device (e.g., the storage device 130, the storage 220, and/or the storage 390). The processing device 120A (e.g., the processor 210, the CPU 340, and/or one or more modules illustrated in FIG. 4A) may execute the set of instructions, and when executing the instructions, the processing device 120A may be configured to perform the process 1200. The operations of the illustrated process presented below are intended to be illustrative. In some embodiments, the process 1200 may be accomplished with one or more additional operations not described and/or without one or more of the operations discussed. Additionally, the order of the operations of process 1200 illustrated in FIG. 2 and described below is not intended to be limiting.

In 1202, the processing device 120A (e.g., the obtaining module 410) may obtain at least two images relating to a blood vessel which are acquired using different imaging sequences.

Each of the at least two images relating to the blood vessel may include a 3D image. The at least two images may include information of a same blood vessel. In some embodiments, each of the different imaging sequences may include an imaging sequence. Exemplary imaging sequences may include a dark blood imaging sequence, a bright blood imaging sequence, etc., more descriptions of which may be found elsewhere in the present disclosure (e.g., operation 502 and the description thereof). Each of the at least two images may include an MR image of a subject including the blood vessel, which is acquired using an imaging sequence. For example, the at least two images may include a first image acquired using a first imaging sequence and one or more second images acquired using one or more second imaging sequences respectively different from the first imaging sequence. For instance, the first imaging sequence may include a first dark blood imaging sequence, and each of the one or more second imaging sequences may include a second dark blood imaging sequence or one of different bright blood imaging sequences.

In some embodiments, the processing device 120A may obtain the at least two images from a storage device (e.g., the storage device 130, the storage 220, the storage 390) of the image processing system 100 or an external storage device (e.g., a medical image database). In some embodiments, the processing device 120A may cause the imaging device 110 to perform at least two scans on a subject including the blood vessel using at least two imaging sequences. For each of the at least two imaging sequences, the processing device 120A may obtain scan data acquired using the imaging sequence and generate an image of the at least two images based on the obtained scan data using an MR reconstruction algorithm, which is similar to that as described in operation 502.

In 1204, the processing device 120A (e.g., the determination module 420) may determine a centerline of the blood vessel based on the at least two images.

In some embodiments, the processing device 120A may determine the centerline of the blood vessel based on the at least two images automatically, semi-automatically, and/or manually. For example, the processing device 120A may register the at least two images. The processing device 120A may determine an enhanced image relating to the centerline of the blood vessel by inputting the at least two images into a machine learning model (e.g., the image recognition model in operation 504). The processing device 120A may determine the centerline of the blood vessel based on the enhanced image. Details regarding the determination of the centerline using the machine learning model may be found elsewhere in the present disclosure (e.g., FIGS. 5 and 6 and relevant descriptions thereof). As another example, the processing device 120A may obtain a reference image relating to the blood vessel whose centerline is determined or is to be determined. The processing device 120A may determine the centerline of the blood vessel by registering the at least two images and the reference image. As still another example, the processing device 120A may determine at least two key points of the centerline of the blood vessel (e g, manually or automatically). The processing device 120A may determine the centerline of the blood vessel based on the at least two key points. As further another example, the processing device 120A may determine the centerline of the blood vessel using an automatic detection algorithm. More descriptions regarding the determination of the centerline of the blood vessel may be found elsewhere in the present disclosure (e.g., FIGS. 5 and 6 and relevant descriptions thereof).

In 1206, for each of the at least two images, the processing device 120A (e.g., the reconstruction module 430) may determine a set of curved planar reformation (CPR) images and a set of multi planar reformation (MPR) images based on the centerline of the blood vessel.

As used herein, a CPR image refers to a 2D image of the blood vessel that indicates anatomical information of the blood vessel (e.g., structure information (e.g., an inner structure, a shape) of the blood vessel) by straightening the blood vessel along the centerline. An angle (e.g., 0°-180°) may be formed between the CPR image and a sagittal plane or a coronal plane of the blood vessel. An MPR image refers to a 2D image (i.e., a cross-section image (also referred to as an axial image) of the blood vessel corresponding to a point of the centerline of the blood vessel. The axial vascular image at the point may be perpendicular to a tangential direction of the centerline of the blood vessel at the point.

In some embodiments, for each of the at least two images, the processing device 120A may determine/reconstruct, based on image data of the image and the centerline of the blood vessel, the set of CPR images (e.g., one or more CPR images corresponding to different angles) using a CPR reconstruction algorithm, a structure reconstruction algorithm, etc. For example, the processing device 120A may obtain first target image data from the image data of the image based on the centerline of the blood vessel. As used herein, the first target image data refers to a portion of the image data that relates to a region of interest (ROI) of the subject. For example, the first target image data may include vascular image data relating to a portion of the blood vessel that is within the ROI. The processing device 120A may generate a CPR image relating to the portion of the blood vessel based on the first target image data.

In some embodiments, for each of the at least two images, the processing device 120A may determine/reconstruct, based on the image data of the image and the centerline of the blood vessel, the set of MPR images (e.g., one or more MPR images corresponding to different points of the centerline) using an MPR reconstruction algorithm. For example, the processing device 120A may obtain a set of second target image data from the image data of the image based on a set of points of the centerline of the blood vessel respectively. As used herein, second target image data corresponding to one point of the set of points refers to vascular image data that is on a plane perpendicular to the tangential direction of the centerline at the point. For the second target image data corresponding to the point, the processing device 120A may generate an MPR image at the point based on the second target image data.

In some embodiments, if the at least two images are acquired using at least two different dark blood imaging sequences, the processing device 120A may determine at least two sets of CPR images corresponding to the at least two different dark blood imaging sequences and at least two sets of MPR images corresponding to the at least two different dark blood imaging sequences. Alternatively, if the at least two images are acquired using at least two different bright blood imaging sequences, the processing device 120A may determine at least two sets of CPR images corresponding to the at least two different bright blood imaging sequences and at least two sets of MPR images corresponding to the at least two different bright blood imaging sequences. Alternatively, if the at least two images include a first image acquired using a dark blood imaging sequence and a second image acquired using a bright blood imaging sequence, the processing device 120A may determine a set of CPR images and a set of MPR images corresponding to the dark blood imaging sequence, and a set of CPR images and a set of MPR images corresponding to the bright blood imaging sequence.

In 1208, the processing device 120A (e.g., the control module 440) may cause one or more of the at least two sets of CPR images and/or one or more of the at least two sets of MPR images to be synchronously displayed on an interface.

In some embodiments, the interface may include a plurality of cells (or areas) each of which is configured with a function such as a display function, a processing function, and/or a control function. Each of the CPR images(s) and the MPR image(s) may be displayed on one of a plurality of cells of the interface according to a preset layout of the interface (e.g., layouts illustrated in FIGS. 13A and 13B). The preset layout of the interface may be a default setting of the image processing system 100 or be adjustable according to different situations (e.g., different display requirements). Alternatively, the processing device 120A may cause a portion of the at least two sets of CPR images and the at least two sets of MPR images to be displayed on the interface. Merely by way of example, the processing device 120A may cause the at least two sets of CPR images to be displayed on the interface and cause the at least two sets of MPR images not to be displayed on the interface. In some embodiments, the processing device 120 may cause the at least two images or a portion thereof to be synchronously displayed on the interface with the at least two sets of CPR images (or a portion thereof) and/or the at least two sets of MPR images (or a portion thereof). In some embodiments, the interface may be configured with different functions, e.g., according to the different layouts. Exemplary functions may include a layout adaptive function, a real-time image comparison function, an image switching function, a multi-contrast display function, a multi-blood-vessel display function, a layout switching function, etc. For illustration purposes, the different functions may be described in detail with reference to an interface 1310 with a first layout shown in FIG. 13A and an interface 1320 with a second layout shown in FIG. 13B.

Figure 13A:
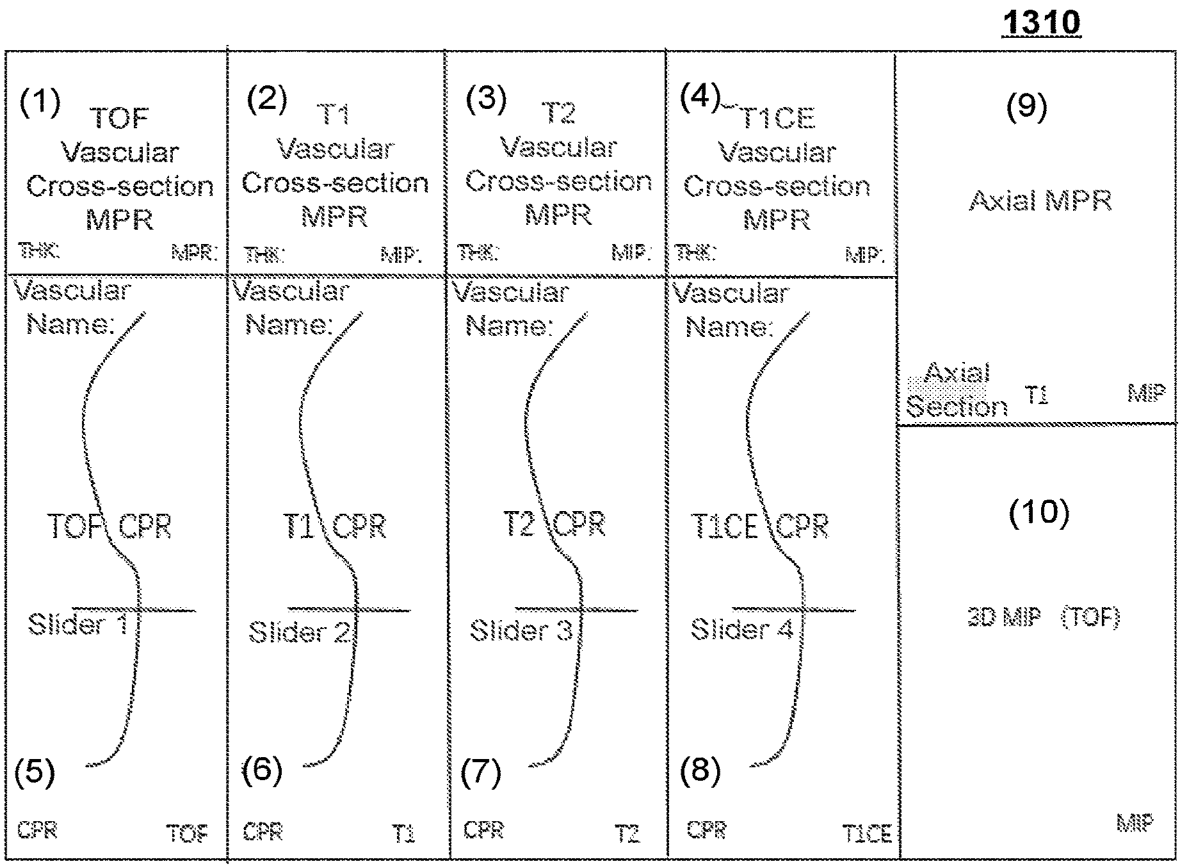
FIGS. 13A and 13B are schematic diagrams illustrating different layouts for displaying images on an exemplary interface according to some embodiments of the present disclosure.

As shown in FIG. 13A, the interface 1310 includes ten cells (1)-(10). Cell (1) is used to display a vascular cross-section image (also referred to as an MPR image) of a blood vessel corresponding to a TOF imaging sequence, cell (2) is used to display an MPR image of the blood vessel corresponding to a T1 imaging sequence, cell (3) is used to display an MPR image of the blood vessel corresponding to a T2 imaging sequence, cell (4) is used to display an MPR image of the blood vessel corresponding to a T1CE imaging sequence, cell (5) is used to display a CPR image of the blood vessel corresponding to the TOF imaging sequence, cell (6) is used to display a CPR image of the blood vessel corresponding to the T1 imaging sequence, cell (7) is used to display a CPR image of the blood vessel corresponding to the T2 imaging sequence, cell (8) is used to display a CPR image of the blood vessel corresponding to the T1CE imaging sequence, cell (9) is used to display a maximum intensity projection (MIP) image of the blood vessel at the axial section (also referred to as an axial MPR image) corresponding to the T1 imaging sequence (e.g., a position of the axial MPR image in cell (9) being the same as a position of the MPR image in cell (2)), and cell (10) is used to display a 3D MIP image of the blood vessel corresponding to the TOF imaging sequence. Accordingly, the interface 1310 displays MPR images corresponding to different imaging sequences in cells (1), (2), (3), and (4). Each of cells (1), (2), (3), and (4) may also be referred to as an MPR cell. The interface 1310 displays CPR images corresponding to different imaging sequences in cells (5), (6), (7), and (8). Each of cells (5), (6), (7), and (8) may also be referred to as a CPR cell. The interface 1310 also displays an original MPR image of the blood vessel corresponding to a specific imaging sequence in cell (9). Cell (9) may also be referred to as an original MPR cell. The interface 1310 further displays a MIP image of the blood vessel corresponding to a default imaging sequence (e.g., a TOF imaging sequence) in cell (10). Cell (10) may also be referred to as a 3D cell.

The interface 1310 may include a layout adaptive function. That is, the interface 1310 can support synchronous display of CPR and/or MPR images of a blood vessel corresponding to different imaging sequences (e.g., 4 imaging sequences). If a count (or number) of the imaging sequences is less than 4, the interface 1310 may be caused to adaptively update to display CPR and/or MPR images corresponding to the imaging sequences. For example, a portion of the cells of the interface 1310 may be caused to display CPR/MPR images of the blood vessel, and the remaining cells of the interface 1310 may be caused to update to display CPR/MPR images of another blood vessel. For instance, if there are two blood vessels each of which corresponding to two imaging sequences, cells (1) and (2) may be MPR cells for displaying MPR images of a first blood vessel corresponding to the two imaging sequences, and cells (5) and (6) be CPR cells for displaying CPR images of the first blood vessel corresponding to the two imaging sequences. Cells (3) and (4) may be MPR cells updated for displaying MPR images of a second blood vessel corresponding to different imaging sequences, and cells (7) and (8) may be CPR images updated for displaying CPR images of the second blood vessel corresponding to different imaging sequences.

The interface 1310 may include a real-time image comparison function. That is, an MPR image of a blood vessel corresponding to a specific imaging sequence may be updated with a CPR image of the blood vessel corresponding to the specific imaging sequence. For example, a slider may be displayed and movable (or adjustable) on a CPR image. When the slider is moved to a position at which the slider intersects with the centerline of the blood vessel on a specific point, the CPR image may be updated to correspond to the specific point. For instance, when slider 1 in cell (5) moves, an MPR image in cell (1) may be updated to correspond to the position of slider 1. That is, the MPR image in cell (1) may be an axial image (perpendicular to a tangent direction of the centerline) at an intersection point of slider 1 and the centerline. In some embodiments, sliders in cells corresponding to different imaging sequences may move synchronously, and MPR images corresponding to different imaging sequences may be updated synchronously. For example, when slider 1 in cell (5) moves, slider 2 in cell (6), slider 3 in cell (7), and/or slider 4 in cell (8) may move with slider 1 a same distance (e.g., to a same position relative to corresponding CPR image), and MPR images in cells (1), (2), (3), and (4) may be updated to correspond to updated positions of sliders 1, 2, 3, and 4. In some embodiments, the CPR images corresponding to different imaging sequences may rotate synchronously on the interface 1310. That is, the CPR images on the interface 1310 can rotate, and when one of the CPR images rotates, and the remaining CPR images may rotate synchronously, such that the CPR images corresponding to different imaging sequences can be compared in a same view angle. For example, when the CPR image in cell (5) rotates, the CPR images in cells (6), (7), and (8) may rotate synchronously with the CPR image in cell (5).

The interface 1310 may include an image switching function. That is, a CPR/MPR image corresponding to an imaging sequence in a cell may be switched to another CPR/MPR image corresponding to another imaging sequence. In some embodiments, a name of a blood vessel (also referred to as a vascular name) may be displayed in a cell that displays a CPR/MPR image of the blood vessel corresponding to an imaging sequence. The vascular name in the cell may be switched to a name of another blood vessel when the CPR/MPR image of the blood vessel is switched to another CPR/MPR image of the another blood vessel corresponding to the imaging sequence. In some embodiments, the interface 1310 may include a straighten function for CPR images displayed on the interface 1310, such that a user can select one or more types of CPR images (e.g., CPR images corresponding to different angles) according to analysis requirement. In some embodiments, the interface 1310 may support a function of switching a thickness of the cross-section of a blood vessel for displaying MPR images of the blood vessel corresponding to different thicknesses. As used herein, a thickness of the cross-section of the blood vessel refers to a distance between two adjacent MPR images (e.g., a distance between two points of the centerline corresponding to the two adjacent MPR images).

The interface 1310 may include a multi-contrast display function. That is, a default setting of the interface 1310 may be displaying images of a same blood vessel corresponding to different imaging sequences for comparison. For example, the interface 1310 may be caused to display CPR images and/or MPR images of a same blood vessel corresponding to different imaging sequences, which can provide information (e.g., the shape, the wall of the cross-section, a plaque, etc.) of the blood vessel in different contrasts.

The interface 1310 may include a multi-blood-vessel display function. That is, the interface 1310 may display CPR/MPR images of different blood vessels in different cells of the interface 1310. For example, the interface 1310 may display CPR/MPR images of four blood vessels of clinical concern for overall evaluation. As another example, the interface 1310 may display CPR/MPR images of contralateral (or opposite) blood vessels. For instance, the interface 1310 may be caused to display in comparison between two CPR images of a first blood vessel corresponding to a left common carotid artery in cells (5) and (6), and display in comparison between two CPR images of a second blood vessel corresponding to a right common carotid artery in cells (7) and (8) for comparatively evaluating the first blood vessel and the second blood vessel.

Figure 13B:
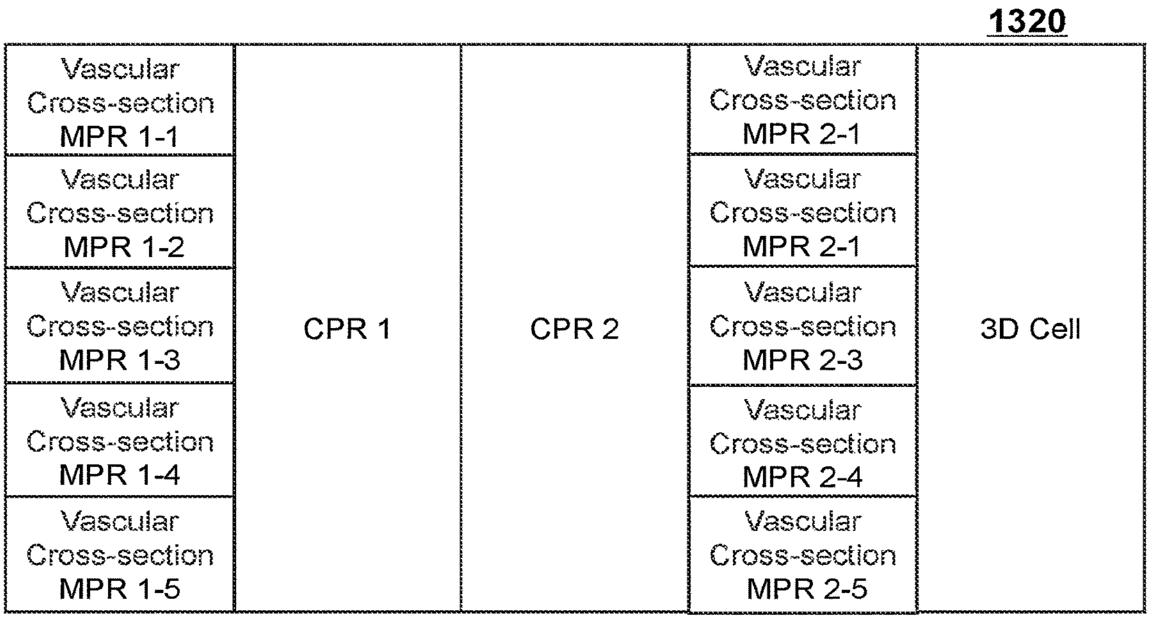

The interface 1310 may include a layout switching function. That is, the interface 1310 with the layout illustrated in FIG. 13A may be switched to an interface 1320 with a layout illustrated in FIG. 13B. As shown in FIG. 13B, the interface 1320 may include a double-CPR-image display function. That is, the interface 1320 may include cells to display CPR images (e.g., a CPR 1 image and a CPR 2 image) of a same blood vessel for comparative analysis of the blood vessel. The interface 1320 may include cells to display multiple MPR images of the blood vessel corresponding to each of the CPR images. For example, the CPR 1 image may correspond to MPR images 1-1, 1-2, 1-3, 1-4, and 1-5. The CPR 2 image may correspond to MPR images 2-1, 2-2, 2-3, 2-4, and 2-5. The interface 1320 may also include a 3D cell, e.g., for displaying a MIP image of the blood vessel.

In some embodiments, the interface (e.g., the interface 1310) may have a function for displaying images (e.g., initial reconstructed images) acquired using different imaging sequences of a same blood vessel or different blood vessels. For example, the interface may include cells to display the at least two images relating to the blood vessel described in operation 1202. The processing device 120A may cause the at least two images to be synchronously displayed on the cells of the interface for comparative analysis of the blood vessel. As another example, the processing device 120A may cause images of different blood vessels (e.g., an image of a first blood vessel and an image of a second blood vessel) to be synchronously displayed on different cells of the interface.

Figure 13C:
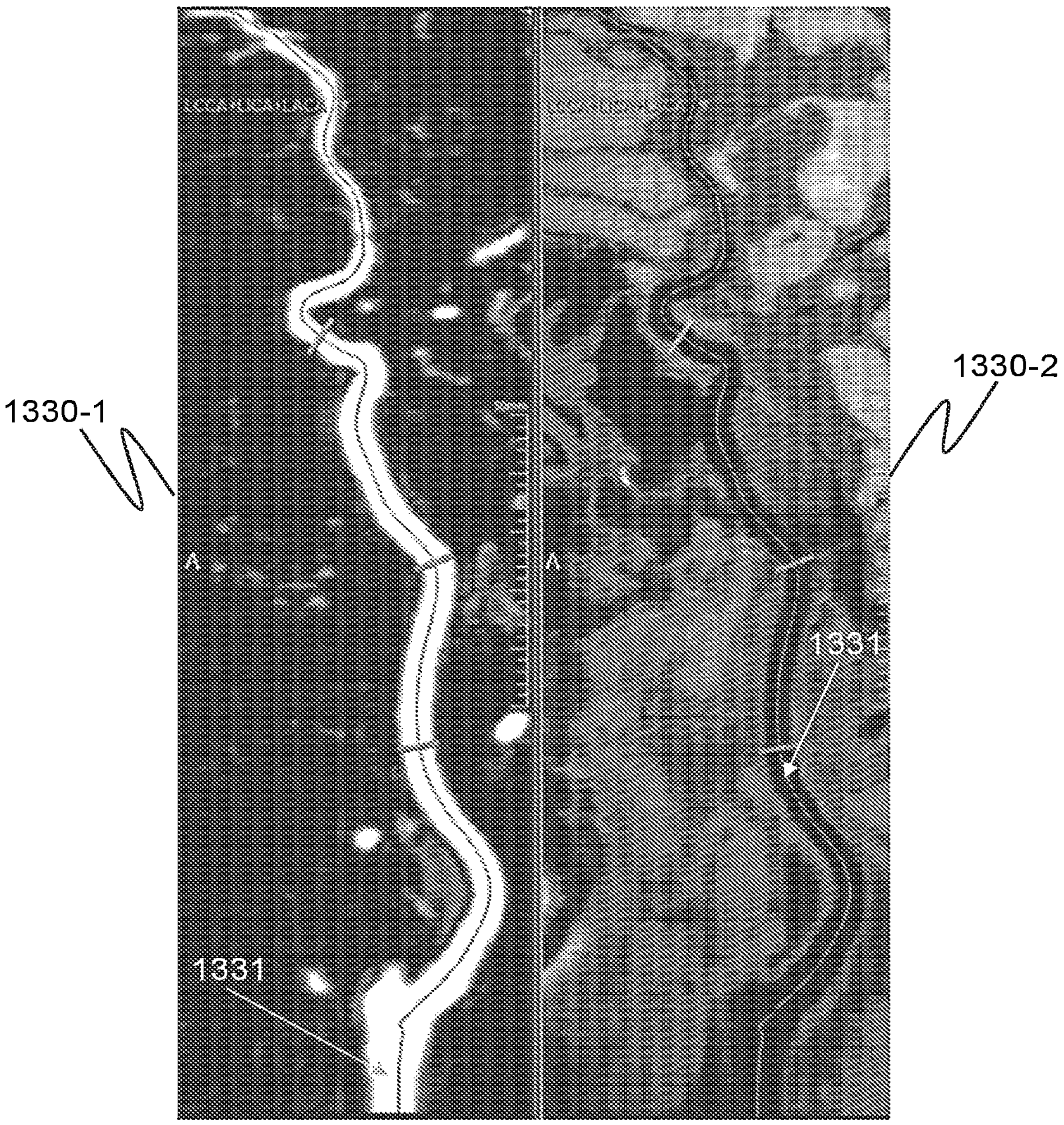
FIGS. 13C-13E are schematic diagrams illustrating different images displayed on an exemplary interface according to some embodiments of the present disclosure.

In some embodiments, the interface may have a function for displaying a centerline, a boundary of the lumen of a blood vessel and/or a boundary of the wall of the blood vessel, a target tissue of the blood vessel, or the like, or any combination thereof, on images (e.g., initial images, CPR images, MPR images, etc.) acquired using different imaging sequences for comparative analysis. For example, the processing device 120A may cause a centerline of a blood vessel (e.g., the centerline determined in operation 1204) to be synchronously displayed on one or more of the at least two sets of CPR images and/or one or more of the at least two sets of MPR images corresponding to the at least two images on the interface. As shown in FIG. 13C, a centerline 1331 of a blood vessel was caused to be synchronously displayed on two images (e.g., a CPR image 1330-1 and a CPR image 1330-2) of the blood vessel corresponding to two different imaging sequences in two cells of the interface. The CPR image 1330-1 was reconstructed based on image data of the blood vessel acquired using a bright blood imaging sequence, and the CPR image 1330-2 was reconstructed based on image data of the blood vessel acquired using a dark blood imaging sequence. The centerline 1331 of the blood vessel was determined based on images acquired using the bright blood imaging sequence and the dark imaging sequences (e.g., according to processes described in FIGS. 5-7).

Figure 13D:
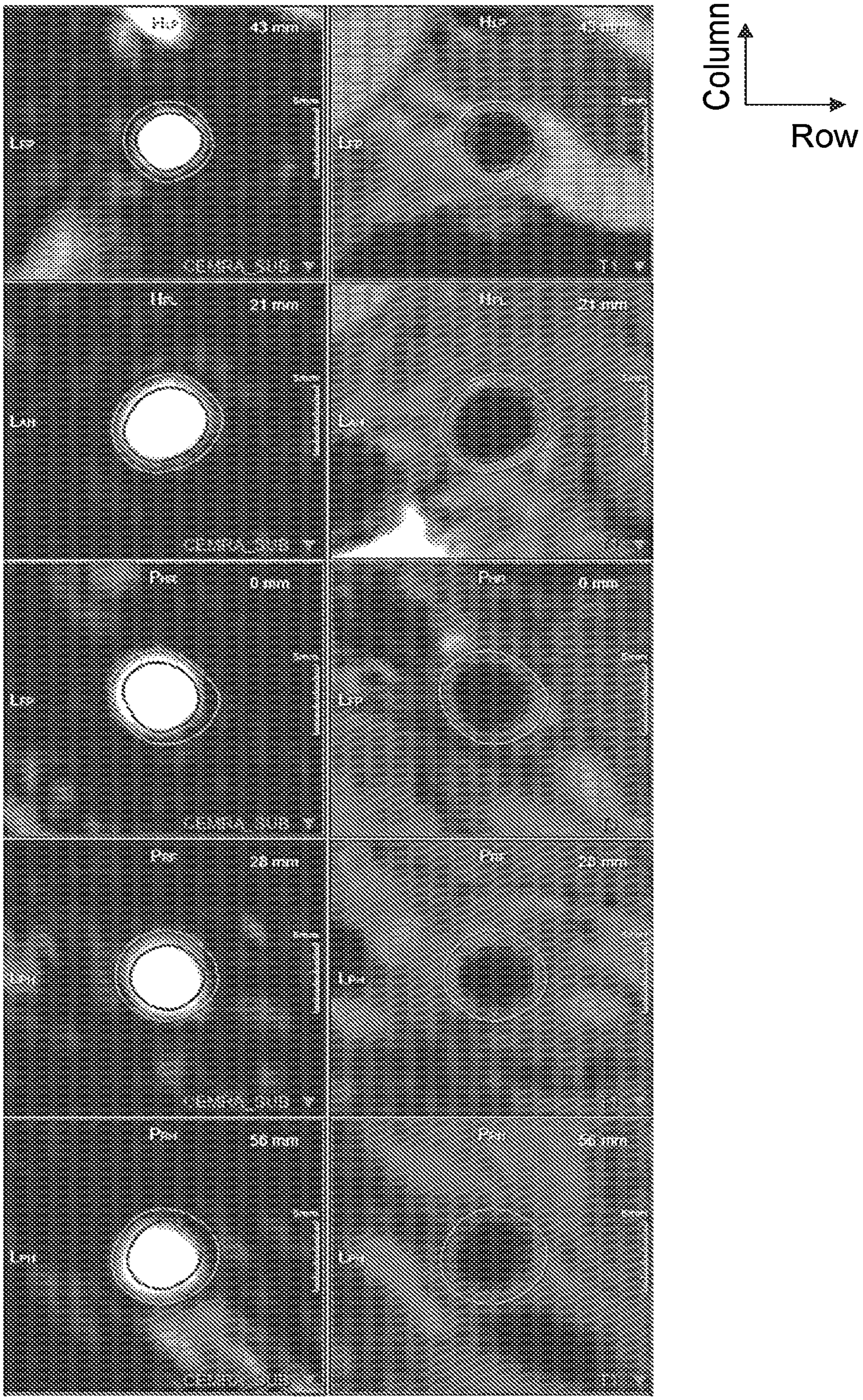

As another example, the processing device 120A may cause a boundary of the lumen of a blood vessel and a boundary of the wall of the blood vessel to be synchronously displayed on one or more of the at least two sets of MPR images on the interface. For example, as shown in FIG. 13D, two columns of images (or five rows of images) (e.g., MPR images) of a blood vessel were displayed on different cells of the interface. A left column of the two columns includes MPR images of the blood vessel corresponding to a bright blood imaging sequence. A right column of the two columns includes MPR images of the blood vessel corresponding to a dark blood imaging sequence. Each row of the five rows includes two MPR images of the blood vessel corresponding to a same point of a centerline of the blood vessel. Each of the MPR images was segmented to determine the boundary of the lumen and the boundary of the wall of the blood vessel in the each MPR image (e.g., according to a process described in FIG. 14). Then, the segmentation results of the MPR images of the blood vessel were displayed on the interface, e.g., the boundary of the lumen and the boundary of the wall of the blood vessel in the each MPR image were displayed in its corresponding MPR image on the interface.

Figure 13E:
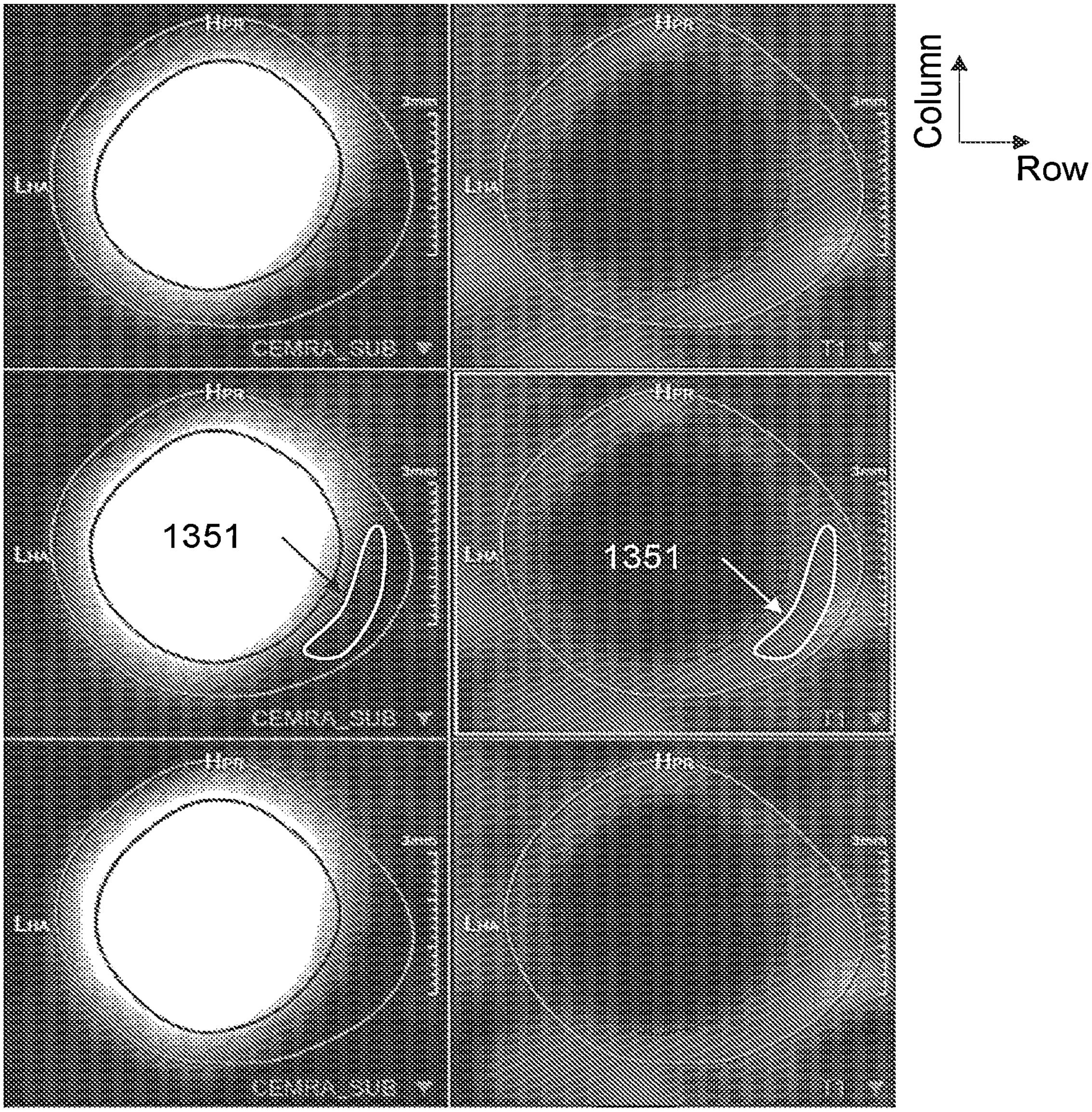

As still another example, the processing device 120A may cause a target tissue of the blood vessel to be synchronously displayed on one or more of the at least two sets of MPR images on the interface. The target tissue of the blood vessel may include a lesion, such as a plaque, an ulceration, a thrombosis, an inflammation, an obstruction, a tumor, etc. For example, as shown in FIG. 13E, two columns of images (or three rows of images) (e.g., MPR images) of a blood vessel were displayed on different cells of the interface. A left column of the two columns includes MPR images of the blood vessel corresponding to a bright blood imaging sequence. A right column of the two columns includes MPR images of the blood vessel corresponding to a dark blood imaging sequence. Each row of the three rows includes two MPR images of the blood vessel corresponding to a same point of a centerline of the blood vessel. Each of the MPR images was segmented to determine the boundary of the lumen and the boundary of the wall of the blood vessel in the each MPR image (e.g., according to a process described in FIG. 14). Then, a target tissue (e.g., a plaque) 1351 of the blood vessel was identified and/or positioned based on the segmentation results of the blood vessel (e.g., according to process 1700 in FIG. 17 and relevant descriptions thereof). The target tissue 1351 was displayed on MPR images of the middle row of the three rows where the target tissue 1351 is located.

In some embodiments, by using the interface including the various functions, the blood vessel may be visualized on the interface, which can help to analyze the blood vessel more efficiently, more conveniently, and more flexibly. For example, by using the slider on the CPR image cell, the blood vessel is visual on the interface and it is convenient to identify which part of the blood vessel is normal and/or which part of the blood vessel is abnormal (e.g., includes stenosis) by moving the slider. In some embodiments, the user may store the images (e.g., the MPR images, and the CPR images) displayed in the interface. Accordingly, the user may select images for printing and/or print an examination report of a patient more efficiently.

It should be noted that the above description regarding the process 1200 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations of the process 1200 may be omitted and/or one or more additional operations may be added. For example, a storing operation may be added elsewhere in the process 1200. In the storing operation, the processing device 120A may store information and/or data (e.g., the centerline, the CPR images, the MPR images, etc.) associated with the image processing system 100 in a storage device (e.g., the storage device 130) disclosed elsewhere in the present disclosure. In some embodiments, the interface may include one or more other layouts except that are shown in FIG. 13A and/or FIG. 13B. For example, one or more additional cells may be added in the interface. As another example, the interface may include one or more additional cells.

Figure 14:
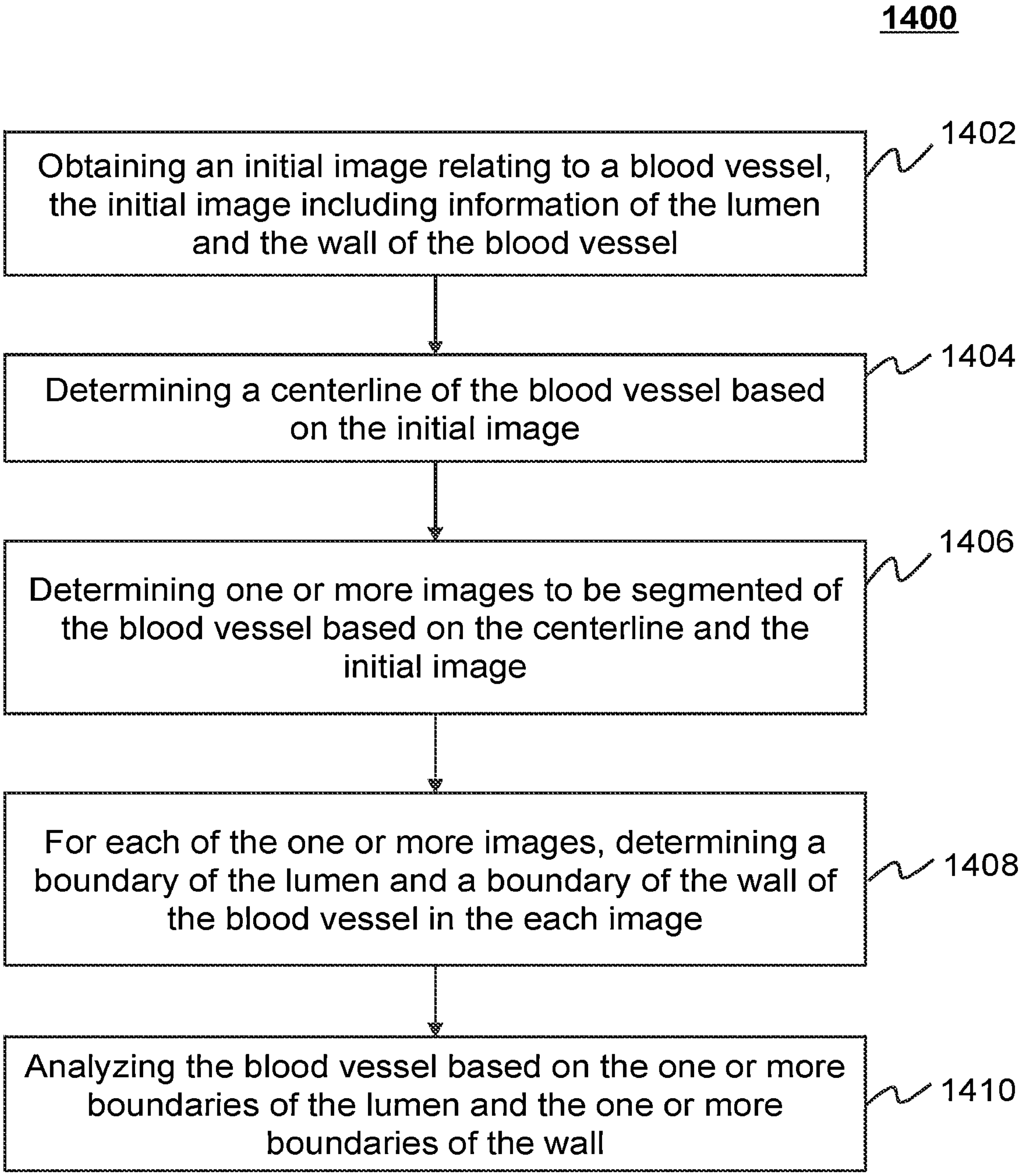
FIG. 14 is a flowchart illustrating an exemplary process for determining a boundary of a lumen of a blood vessel and a boundary of a wall of the blood vessel according to some embodiments of the present disclosure.

FIG. 14 is a flowchart illustrating an exemplary process 1400 for determining a boundary of a lumen and a wall of a blood vessel according to some embodiments of the present disclosure. In some embodiments, process 1400 may be implemented as a set of instructions (e.g., an application) stored in a storage device (e.g., the storage device 130, the storage 220, and/or the storage 390). The processing device 120A (e.g., the processor 210, the CPU 340, and/or one or more modules illustrated in FIG. 4A) may execute the set of instructions, and when executing the instructions, the processing device 120A may be configured to perform the process 1400. The operations of the illustrated process presented below are intended to be illustrative. In some embodiments, the process 1400 may be accomplished with one or more additional operations not described and/or without one or more of the operations discussed. Additionally, the order of the operations of process 1400 illustrated in FIG. 14 and described below is not intended to be limiting.

In 1402, the processing device 120A (e.g., the obtaining module 410) may obtain an initial image relating to a blood vessel.

In some embodiments, the blood vessel may include a blood vessel of the brain, a blood vessel of the neck, a blood vessel of a lung, a blood vessel of the heart, etc., more descriptions of which may be found elsewhere in the present disclosure (e.g., operation 502 and the descriptions thereof). In some embodiments, the initial image (also referred to as a first initial image) may include information of at least the lumen and the wall of the blood vessel. The lumen of the blood vessel refers to a hollow passageway through which blood flows. The wall of the blood vessel may include an inner wall (which is the innermost layer of the blood vessel), an outer wall (which is the outermost layer of the blood vessel), etc. The inner wall of the blood vessel may be a boundary between the wall of the blood vessel and the lumen of the blood vessel. The outer wall of the blood vessel may be a boundary of the blood vessel and the outside of the blood vessel. The wall of the blood vessel may include a tunica externa, an external elastic membrane, a tunica media, an internal elastic membrane, a tunica intima, an endothelium, etc.

Figure 16A:
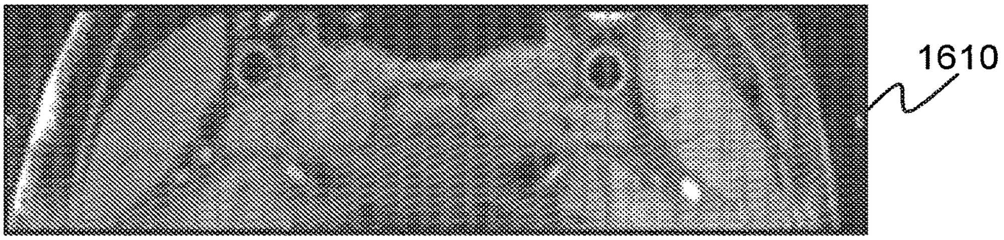
FIG. 16A is a schematic diagram illustrating an exemplary initial image relating to a blood vessel according to some embodiments of the present disclosure.

In some embodiments, the initial image may be a three-dimensional image acquired by an imaging device (e.g., the imaging device 110). For example, the initial image may be acquired by an MRI device, a CT device, a DSA device, an IVUS device, or the like, or any combination thereof. Taking the MRI device as an example, the initial image may be acquired using an imaging sequence, e.g., a dark blood imaging sequence, a bright blood imaging sequence. Exemplary images acquired according to the dark blood imaging sequence may include a T1 enhanced image, a T1 image, a T2 image, a proton density image, or the like, or any combination thereof. As shown in FIG. 16A, an image 1610 is an initial image relating to a blood vessel acquired using a dark blood imaging sequence. In some embodiments, the processing device 120A may obtain the initial image from a storage device as described elsewhere in the present disclosure and/or by causing the imaging device to perform a scan on the blood vessel, which is similar to or the same as the obtaining of the first image as described in operation 502 in FIG. 5.

In 1404, the processing device 120A (e.g., the determination module 420) may determine a centerline of the blood vessel based on the initial image.

Figure 16B:
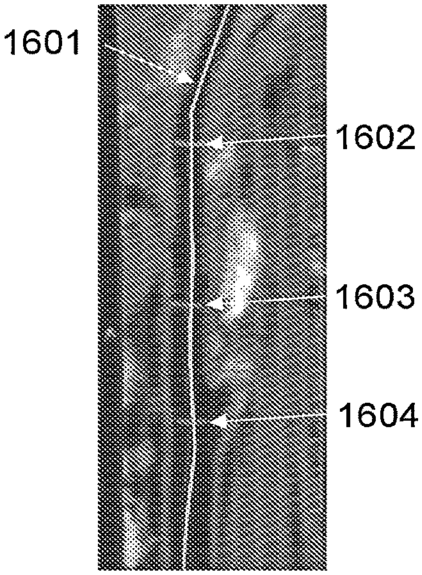
FIG. 16B is a schematic diagram illustrating an exemplary centerline of a blood vessel according to some embodiments of the present disclosure.

The centerline of the blood vessel may refer to a line located in and along the blood vessel. In some embodiments, the centerline of the blood vessel may refer to a collection of pixels located in or close to a central area of the blood vessel. In some embodiments, the centerline of the blood vessel may refer to a line connecting pixels with an equal distance or substantially equal distance to the boundary of the lumen of the blood vessel. As shown in FIG. 16B, line 1601 indicates an exemplary centerline of the blood vessel that is determined based on the initial image 1610.

In some embodiments, the processing device 120A may determine the centerline of the blood vessel according to an image registration operation (e.g., a template matching operation). For example, the processing device 120A may obtain a second image relating to the blood vessel or a second blood vessel (e.g., with the same type as the blood vessel in the initial image) whose centerline is determined. The processing device 120A may register the initial image and the second image to obtain a registration relation between the initial image and the second image. The processing device 120A may determine the centerline of the initial image based on the registration relation and the centerline in the second image. In some embodiments, the second image may be acquired using an imaging sequence the same as or different from the imaging sequence corresponding to the initial image. For instance, the initial image may be acquired using a dark blood imaging sequence, and the second image may be acquired using a bright blood imaging sequence.

In some embodiments, the processing device 120A may determine the centerline of the blood vessel according to an interactive detection operation. That is, the processing device 120A may determine at least two key points of the blood vessel based on the initial image manually or semi-automatically. For example, the processing device 120A may obtain a user instruction including information (e.g., coordinates) of the at least two key points of the blood vessel on the initial image. The processing device 120A may determine the at least two key points of the blood vessel based on the user instruction. Further, the processing device 120A may determine the centerline of the blood vessel based on the at least two key points and the initial image using a path planning algorithm, a minimum descent algorithm, a minimum spanning tree algorithm, etc. For example, the processing device 120A may determine an optimal path between the at least two key points and determine the centerline of the blood vessel based on the optimal path. For instance, a pixel value (e.g., a grayscale) of each point (or pixel) on the initial image may correspond to a function f(x). The processing device 120A may determine a weight function g(x) based on the function f(x). For example, for the initial image acquired using a bright blood imaging sequence, the processing device 120A may determine the weight function g(x) by performing an inverse operation on the function f(x). For a specific point of the initial image acquired using the bright blood imaging sequence, the greater a pixel value of the specific point is, the smaller a weight of the specific point may be. That is, for a specific point x of the initial image acquired using the bright blood imaging sequence, the greater a value of the function f(x) is, the smaller a value of the function g(x) may be. For the initial image acquired using a bright blood imaging sequence, the nearer a pixel from the centerline of the blood vessel, the greater a value of the function f(x) and the smaller a value of the function g(x). As another example, for the initial image acquired using a dark blood imaging sequence, the nearer a pixel from the centerline of the blood vessel, the smaller a value of the function f(x) and the smaller a value of the function g(x). For a specific point of the initial image acquired using the dark blood imaging sequence, the smaller a pixel value of the specific point is, the smaller a weight of the specific point may be. A distance between the at least two key points of the blood vessel may be represented by Equation (1) as follows:

$$h(x)=\Sigma_{i=1}^{n} g(x_i), \tag{1}$$

where n refers to steps from one point of the at least two key points to another point of the at least two key points. When a value of h(x) reaches a minimum value, a path corresponding to the minimum value may be the optimal path between the at least two key points. The processing device 120A may further designate the optimal path as the centerline of the blood vessel.

In some embodiments, the processing device 120A may determine the centerline of the blood vessel according to an automatic detection operation. That is, the processing device 120A may determine the at least two key points of the blood vessel based on the initial image automatically. For example, the processing device 120A may determine the at least two key points based on a machine learning model. More descriptions regarding the determination of the at least two key points may be found elsewhere in the present disclosure. See, e.g., FIG. 8 and relevant descriptions thereof. Further, the processing device 120A may determine the optimal path between the at least two key points, e.g., using a path planning algorithm, a minimum descent algorithm, a minimum spanning tree algorithm, etc. The processing device 120A may further designate the optimal path as the centerline of the blood vessel.

In some embodiments, the processing device 120A may obtain one or more second initial images relating to the blood vessel. Each of the one or more second initial images may be generated using an imaging sequence different from that corresponding to the first initial image. The processing device 120A may register the one or more second initial images and the first initial image. The processing device 120A may determine an enhanced image relating to the centerline of the blood vessel based on the registered images (e.g., the first initial image and the one or more registered second initial images) using a machine learning model (e.g., the image recognition model as described in FIG. 5 or 6). The processing device 120A may determine the centerline of the blood vessel based on the enhanced image. More descriptions regarding the determination of the centerline of the blood vessel using a machine learning model may be found elsewhere in the present disclosure. See, e.g., FIGS. 5-7 and relevant descriptions thereof. It should be noted that the determination of the centerline of the blood vessel is merely provided for the purposes of illustration, and not intended to limit the scope of the present disclosure.

In 1406, the processing device 120A (e.g., the determination module 420) may determine one or more images to be segmented of the blood vessel based on the centerline and the initial image.

Figure 16C:
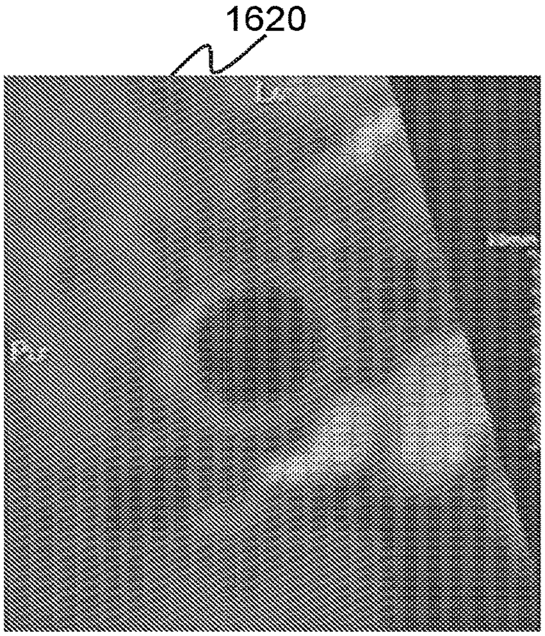
FIG. 16C is a schematic diagram illustrating an exemplary axial image of a blood vessel according to some embodiments of the present disclosure.

Each of the one or more images may be an axial image (e.g., an MPR image) of the blood vessel. That is, each image to be segmented may be a 2D image corresponding to a point of the centerline of the blood vessel. As shown in FIG. 16B, lines 1602, 1603, and 1604 indicate three axial images of the blood vessel, respectively. As shown in FIG. 16C, an image 1620 is an exemplary axial image corresponding to one of the lines 1602, 1603, and 1604.

In some embodiments, the processing device 120A may determine one or more intermediate images by segmenting the initial image along a direction perpendicular to the centerline. The one or more intermediate images may be equal-spaced or not. For example, a distance between any two adjacent intermediate images of the one or more intermediate images may be the same. As another example, a distance between a first pair of adjacent intermediate images may be different from a distance between a second pair of adjacent intermediate images. The distance between two adjacent intermediate images may be a default setting of the image processing system 100 or be preset according to the blood vessel (e.g., a position, a type, a size, etc., of the blood vessel). In some embodiments, each of the one or more intermediate images may correspond to a point of the centerline of the blood vessel, and perpendicular to a tangential direction of the centerline at the point. The processing device 120A may determine one or more points of the centerline each of which corresponds to the one or more intermediate images. The processing device 120A may determine the one or more intermediate images by segmenting the initial image based on the one or more points. Further, for each of the one or more intermediate images, the processing device 120A may determine the each intermediate image as one of the one or more images to be segmented of the blood vessel. Alternatively, for each of the one or more intermediate images, the processing device 120A may determine a portion of the each intermediate image as one of the one or more images. Accordingly, each of the one or more images may have a smaller size than its corresponding intermediate image as long as including the blood vessel included in the corresponding intermediate image. For example, a distance between a margin of each image and the outer wall of the blood vessel in the each image may be greater than a distance threshold. As another example, the margin of the each image may be tangent to the outer wall of the blood vessel.

In 1408, for each of the one or more images, the processing device 120A (e.g., the determination module 420) may determine a boundary of the lumen of the blood vessel and a boundary of the wall of the blood vessel in the each image (e.g., using a machine learning model (also referred to as a boundary determination model, or a second machine learning model)).

As used herein, the boundary of the lumen of the blood vessel may refer to a boundary of the inner wall of the blood vessel; and the boundary of the wall of the blood vessel may refer to a boundary of the outer wall of the blood vessel. The boundary determination model (also referred to as a second machine learning model) may refer to a process or an algorithm for determining a boundary of the lumen of a blood vessel and a boundary of the wall of the blood vessel based on an image to be segmented of the blood vessel. The boundary determination model may include a convolutional neural network (CNN) model, a recurrent neural network (RNN) model, a long short term memory (LSTM) network model, a fully convolutional neural network (FCN) model, a generative adversarial network (GAN) model, a radial basis function (RBF) machine learning model, a DeepMask model, a SegNet model, a dilated convolution model, a conditional random fields as recurrent neural networks (CRFasRNN) model, a pyramid scene parsing network (pspnet) model, or the like, or any combination thereof.

Figure 16D:
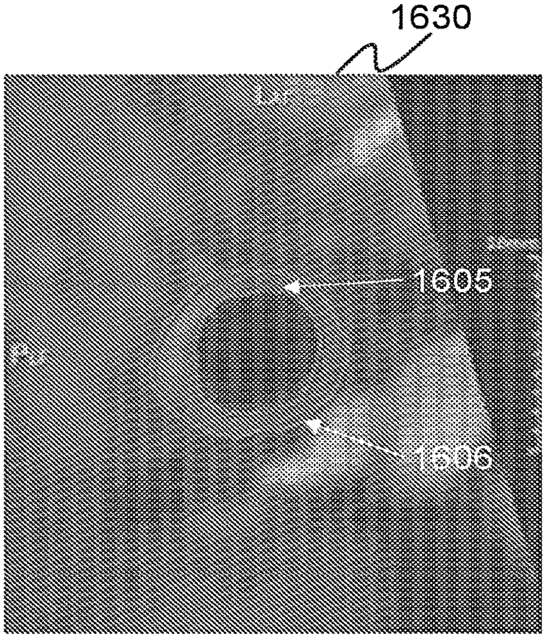
FIG. 16D is a schematic diagram illustrating an exemplary image that is determined based on a mask image according to some embodiments of the present disclosure.
Figure 16E:
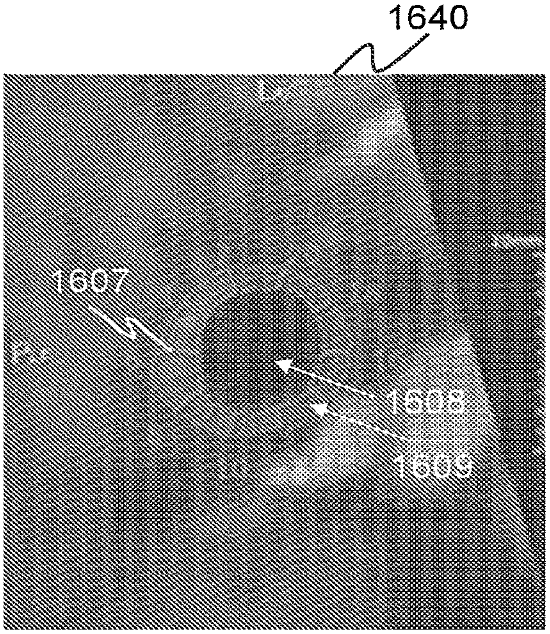
FIG. 16E is a schematic diagram illustrating an exemplary image that is determined by performing a radial sampling according to some embodiments of the present disclosure.
Figure 16F:
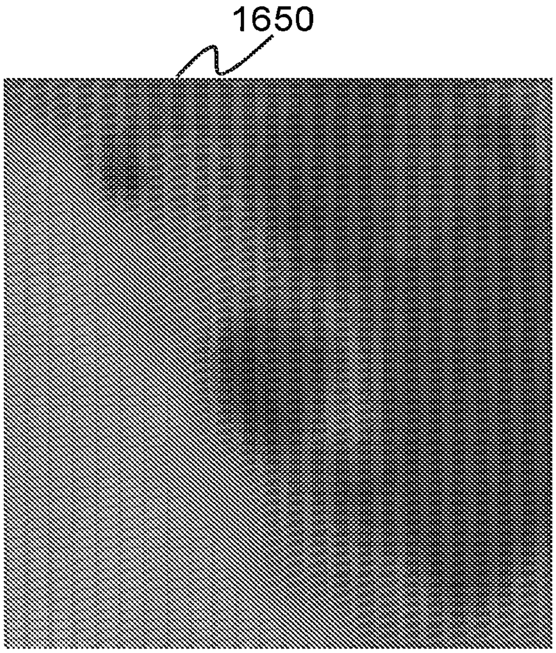
FIG. 16F is a schematic diagram illustrating an exemplary axial image of a blood vessel according to some embodiments of the present disclosure.
Figure 16G:
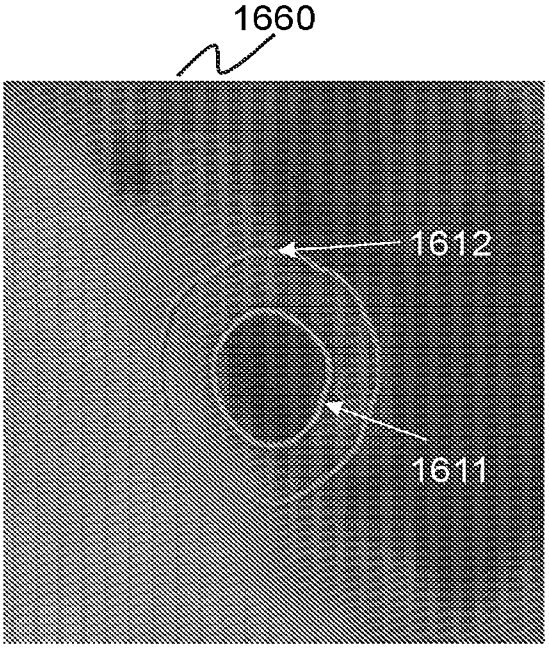
FIG. 16G is a schematic diagram illustrating an exemplary image that is determined based on a mask image according to some embodiments of the present disclosure.

In some embodiments, for each of the one or more images, the processing device 120A may input the image into the boundary determination model, and the processing device 120A may determine the boundary of the lumen of the blood vessel and the boundary of the wall of the blood vessel included in the each image based on an output of the boundary determination model. The output of the boundary determination model may include a mask image. That is, the boundary determination model may output the mask image based on the image. As used herein, a mask image may indicate information of the boundary of the lumen of the blood vessel and the boundary of the wall of the blood vessel. For example, the mask image may include a same size as the image and include a plurality of pixels each of which corresponds to one of a plurality of pixels of the image. The plurality of pixels of the mask image may be labeled by a plurality of labels (e.g., 0 or 1). Pixels of the mask image that correspond to the boundary of the lumen of the blood vessel and the boundary of the wall of the blood vessel in the image may correspond to the same first labels (e.g., 1), and the remaining pixels of the mask image may correspond to the same second labels (e.g., 0). Further, the processing device 120A may determine the boundary of the lumen of the blood vessel and the boundary of the wall of the blood vessel included in the image based on its corresponding mask image. For example, the processing device 120A may determine target pixels of the image based on the pixels corresponding to the same first labels. The processing device 120A may change pixel values of the target pixels of the image to be equal to a preset pixel value such that the boundary of the lumen and the boundary of the wall can be illustrated in the image. As shown in FIG. 16D, an image 1630 is determined based on the image 1620 and a mask image corresponding to the image 1620. The image 1630 may include a boundary 1605 of the lumen of the blood vessel and a boundary 1606 of the wall of the blood vessel shown in the image 1630. As shown in FIG. 16G, an image 1660 is determined based on an image 1650 of a blood vessel to be segmented shown in FIG. 16F. The image 1660 may include a boundary 1611 of the lumen and a boundary 1612 of the wall of the blood vessel shown in the image 1660. Alternatively, the processing device 120A may input the image into the boundary determination model, and the boundary determination model may directly output a segmented image including the boundary of the lumen and the boundary of the wall of the blood vessel. The segmented image may be the same as or similar to that is determined based on the mask image and the image.

In some embodiments, the processing device 120A may determine one or more outputs corresponding to the one or more images respectively by inputting the one or more images into the boundary determination model. That is, the processing device 120A may input the one or more images into the boundary determination model together, and the boundary determination model may output one or more mask images each of which corresponds to one of the one or more images. Further, for each of the one or more images, the processing device 120A may determine the boundary of the lumen of the blood vessel and the boundary of the wall of the blood vessel included in the each image based on one of the one or more outputs corresponding to the each image.

In some embodiments, after the processing device 120A determines the boundary of the lumen of the blood vessel and the boundary of the wall of the blood vessel using the boundary determination model, the processing device 120A may further determine whether the boundary of the lumen of the blood vessel and the boundary of the wall of the blood vessel in the each image satisfy an actual requirement. In response to the determination that the boundary of the lumen of the blood vessel and the boundary of the wall of the blood vessel in the each image satisfy the actual requirement, the processing device 120A may proceed to perform a next operation (e.g., operation 1710, a storage operation). In response to the determination that the boundary of the lumen of the blood vessel and/or the boundary of the wall of the blood vessel in the each image do not satisfy the actual requirement, the processing device 120A may obtain a user instruction including information (e.g., coordinates) of a modified boundary of the lumen of the blood vessel and/or a modified boundary of the wall of the blood vessel in the each image. The processing device 120A may update the boundary of the lumen of the blood vessel and the boundary of the wall of the blood vessel in the each image based on the user instruction.

In some embodiments, before inputting the one or more images into the boundary determination model, the processing device 120A may adjust a resolution of the each image until a preset resolution is satisfied. The preset resolution may be determined according to the training of the boundary determination model. For example, the preset resolution may be a minimum resolution of a sample image used for training the boundary determination model. In some embodiments, the processing device 120A may adjust the resolution of the each image through an interpolation algorithm. For example, the each image may be adjusted using a bicubic interpolation algorithm. It should be noted that the interpolation algorithm is merely provided for the purposes of illustration, and not intended to limit the scope of the present disclosure. In some embodiments, since the signal to noise ratio (SNR) of the each image is decreased with the increase of the resolution of the each image using the interpolation algorithm, the processing device 120A may need to take the SNR of the each image into consideration during adjusting the resolution of the each image. That is, the adjusted image may satisfy both the preset resolution and a preset SNR. For example, the resolution of the adjusted image may be greater than the preset resolution and the SNR of the adjusted image may be greater than the preset SNR, thereby ensuring both the resolution and SNR of the each image satisfying an actual requirement.

In some embodiments, the processing device 120A (e.g., the obtaining module 410) may obtain the boundary determination model from one or more components of the image processing system 100 (e.g., the storage device 130, the terminals(s) 140) or an external source via a network (e.g., the network 150). For example, the boundary determination model may be previously generated by a computing device (e.g., the processing device 120B), and stored in a storage device (e.g., the storage device 130, the storage 220, and/or the storage 390) of the image processing system 100. The processing device 120A may access the storage device and retrieve the boundary determination model. In some embodiments, the boundary determination model may be generated according to a machine learning algorithm. The machine learning algorithm may include but not be limited to an artificial neural network algorithm, a deep learning algorithm, a decision tree algorithm, an association rule algorithm, an inductive logic programming algorithm, a support vector machine algorithm, a clustering algorithm, a Bayesian network algorithm, a reinforcement learning algorithm, a representation learning algorithm, a similarity and metric learning algorithm, a sparse dictionary learning algorithm, a genetic algorithm, a rule-based machine learning algorithm, or the like, or any combination thereof. The machine learning algorithm used to generate the boundary determination model may be a supervised learning algorithm, a semi-supervised learning algorithm, an unsupervised learning algorithm, etc. In some embodiments, the boundary determination model may be generated by a computing device (e.g., the processing device 120B) that may perform a process (e.g., process 1500) for generating a boundary determination model disclosed herein. More descriptions regarding the generation of the boundary determination model may be found elsewhere in the present disclosure. See, e.g., FIG. 15 and relevant descriptions thereof.

In 1410, the processing device 120A (e.g., the determination module 420) may analyze the blood vessel based on the one or more boundaries of the lumen and the one or more boundaries of the wall.

In some embodiments, for the each image, the processing device 120A may determine one or more vascular parameters of the blood vessel included in the each image based on the boundary of the lumen and the boundary of the wall corresponding to the each image. The one or more vascular parameters may include a diameter stenosis, a normal wall index, an area stenosis, or the like, or any combination thereof.

In some embodiments, the processing device 120A may determine a diameter stenosis of the blood vessel based on a reference diameter and a diameter between the lumen and the wall of the blood vessel. As used herein, the reference diameter refers to a diameter between the lumen and the wall of a normal portion of the blood vessel. The normal portion of the blood vessel may include a normal portion of the blood vessel near the heart or a normal portion of the blood vessel far away from the heart. Alternatively, if the blood vessel included in the each image has a lesion, the reference diameter may include a diameter between the lumen and the wall of the blood vessel before the blood vessel has the lesion. As used herein, the diameter between the lumen and the wall refers to a radial distance between the boundary of the lumen and the boundary of the wall. For example, for the each image, the processing device 120A may perform a radial sampling on the boundary of the lumen and the boundary of the wall of the blood vessel include in the each image. Therefore, the processing device 120A may obtain a plurality of diameters between the lumen and the wall included in the each image according to the radial sample results. As shown in FIG. 16E, an image 1640 is determined by performing a radial sampling on the boundary 1605 and the boundary 1606 included in the image 1630. The image 1640 illustrates twenty diameters 1607 between the lumen and the wall included in the image 1630. The processing device 120A may determine a minimum value (and/or a maximum value) among the plurality of diameters between the lumen and the wall included in the each image. Further, the processing device 120A may determine the diameter stenosis of the blood vessel included in the each image according to Equation (2):

$$R_{ds}=(D_r-D_{min})/D_r\times 100\%, \quad (2)$$

where $R_{ds}$ represents the diameter stenosis of the blood vessel included in the each image, $D_r$ represents the reference diameter between the lumen and the wall of the blood vessel, and $D_{min}$ represents the minimum value among the plurality of diameters between the lumen and the wall of the blood vessel included in the each image.

In some embodiments, the processing device 120A may determine a normal wall index of the blood vessel based on an area of the lumen and an area of the wall of the blood vessel. As used herein, the area of the lumen of the blood vessel refers to an area of the lumen of the blood vessel included in the each image, e.g., area 1608 of the blood vessel included in the image 1640 as shown in FIG. 16E. The area of the wall of the blood vessel refers to an area between the lumen and the wall of the blood vessel included in the each image, e.g., area 1609 of the blood vessel included in the image 1640 as shown in FIG. 16E. For example, the processing device 120A may determine the area of the lumen and the area of the wall based on the boundary of the lumen and the boundary of the wall included in the each image. Further, the processing device 120A may determine the normal wall index of the blood vessel included in the each image according to Equation (3):

$$I_{nw}=S_w/(S_w+S_l)/\times 100\%, \quad (3)$$

where $I_{nw}$ represents the normal wall index of the blood vessel included in the each image, $S_w$ represents the area of the wall of the blood vessel included in the each image, and $S_l$ represents the area of the lumen of the blood vessel included in the each image.

In some embodiments, the processing device 120A may determine an area stenosis of the blood vessel based on a reference area and the area of the lumen of the blood vessel. As used herein, the reference area refers to an area of a normal lumen. The normal lumen refers to a lumen of a blood vessel having no lesion. Alternatively, if the blood vessel included in the each image has a lesion, the reference area may include an area of the lumen of the blood vessel before the blood vessel has the lesion, and the area of the lumen of the blood vessel included in the each image may include a residual area of the lumen of the blood vessel having the lesion included in the each image. For example, the processing device 120A may determine an area of a plaque included in the each image based on the area of the lumen included in the each image and the reference area. For example, the processing device 120A may determine the area of the plaque by subtracting the area of the lumen included in the each image from the reference area of the lumen according to Equation (4):

$$S_p=S_r-S_l, \quad (4)$$

where $S_p$ represents the area of the plaque included in the each image, $S_r$ represents the reference area, and $S_l$ represents the area of the lumen included in the each image. Further, the processing device 120A may determine the area stenosis of the blood vessel included in the each image based on the area of the plaque and the reference area according to Equation (5):

$$R_{as}=S_p/S_r\times 100\%=(S_r-S_l)/S_r\times 100\%, \quad (5)$$

where $R_{as}$ represents the area stenosis of the blood vessel included in the each image.

In some embodiments, the processing device 120A may determine a target diameter stenosis of the blood vessel from the one or more diameter stenoses of the blood vessel corresponding to the one or more images for subsequent vascular analysis. For example, the target diameter stenosis of the blood vessel may be minimum among the one or more diameter stenoses.

In some embodiments, the processing device 120A may determine whether the blood vessel has a target tissue based on the one or more vascular parameters of each of the one or more images. For example, if determining that one or more of the vascular parameters do not satisfy a preset condition, the processing device 120A may determine that the blood vessel has a target tissue. The target tissue may be a lesion, such as a plaque, an ulceration, a thrombosis, an inflammation, an obstruction, a tumor, etc. The preset condition may include normal values of the one or more vascular parameters. In some embodiments, the preset condition may be determined according to the experiences of the user, a default value based on a medical database, or be adjustable in different situations. In response to determining that the blood vessel has the target tissue, the processing device 120A may determine a position of the target tissue in the blood vessel. For example, the processing device 120A may determine the position of the target tissue manually. As another example, the processing device 120A may determine a labeled centerline based on the centerline of the blood vessel using a labeled centerline determination model (also referred to a third machine learning model). The labeled centerline may include a name of the centerline and one or more labeled segments of the centerline. The processing device 120A may determine the position of the target tissue based on the target tissue and the labeled centerline. More descriptions regarding the determination of the labeled centerline may be found elsewhere in the present disclosure. See, e.g., FIG. 17 and relevant descriptions thereof.

In some embodiments, the processing device 120A may transmit the boundary of the lumen of the blood vessel and the boundary of the wall of the blood vessel in the each image, the identified target tissue (if any), and/or the one or more vascular parameters to one or more components of the image processing system 100. For example, the processing device 120A may transmit the boundary of the lumen of the blood vessel and the boundary of the wall of the blood vessel in the each image, the identified target tissue (if any), and/or the one or more vascular parameters to a terminal (e.g., the terminal 140). An interface of the terminal 140 may display the boundary of the lumen of the blood vessel and the boundary of the wall of the blood vessel in the each image, the identified target tissue (if any), and/or the one or more vascular parameters. As another example, the processing device 120A may transmit the boundary of the lumen of the blood vessel and the boundary of the wall of the blood vessel in the each image, the identified target tissue (if any), and/or the one or more vascular parameters to a storage device (e.g., the storage device 130) for storage and/or retrieval.

It should be noted that the above description regarding the process 1400 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations of the process 1400 may be omitted, and/or one or more additional operations may be added. For example, a storing operation may be added elsewhere in the process 1400. In the storing operation, the processing device 120A may store information and/or data (e.g., the initial image related to the blood vessel, the boundary of the lumen of the blood vessel, the boundary of the wall of the blood vessel, the boundary determination model, the identified target tissue (if any), the one or more vascular parameters, etc.) associated with the image processing system 100 in a storage device (e.g., the storage device 130) disclosed elsewhere in the present disclosure. As another example, operation 1402 may be omitted. That is, the processing device 120A may directly obtain the initial image with the centerline of the blood vessel that has been labeled in the initial image.

Figure 15:
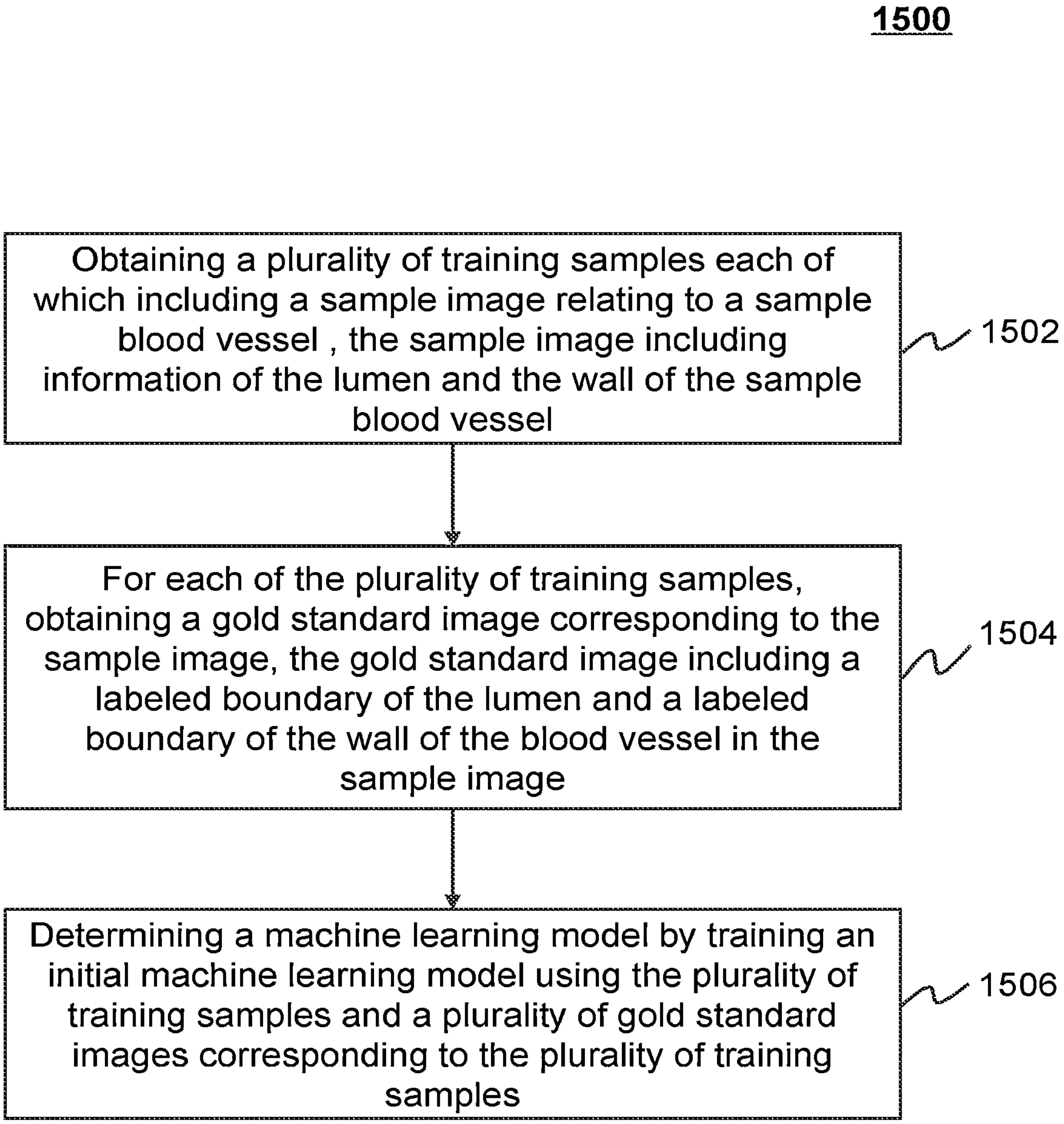
FIG. 15 is a flowchart illustrating an exemplary process for generating a boundary determination model according to some embodiments of the present disclosure.

FIG. 15 is a flowchart illustrating an exemplary process 1500 for generating a boundary determination model according to some embodiments of the present disclosure. In some embodiments, the process 1500 may be implemented as a set of instructions (e.g., an application) stored in a storage device (e.g., the storage device 130, storage 220, and/or storage 390). The processing device 120B (e.g., the processor 210, the CPU 340, and/or one or more modules illustrated in FIG. 4B) may execute the set of instructions, and when executing the instructions, the processing device 120B may be configured to perform the process 1500. The operations of the illustrated process presented below are intended to be illustrative. In some embodiments, the process 1500 may be accomplished with one or more additional operations not described and/or without one or more of the operations discussed. Additionally, the order of the operations of process 1500 illustrated in FIG. 15 and described below is not intended to be limiting. In some embodiments, the boundary determination model described in connection with operation 1408 in FIG. 14 may be obtained according to the process 1500. In some embodiments, the process 1500 may be performed by another device or system other than the image processing system 100, e.g., a device or system of a vendor of a manufacturer. For illustration purposes, the implementation of the process 1500 by the processing device 120B is described as an example.

In 1502, the processing device 120B (e.g., the obtaining module 460) may obtain a plurality of training samples. Each of the plurality of training samples may include a sample image relating to a sample blood vessel. The sample image may include information of the lumen and the wall of the sample blood vessel.

The sample blood vessel may be of the same type as or a different type from the blood vessel as described in connection with FIG. 14. For example, if the boundary determination model is used to determine a boundary of the lumen of the blood vessel and a boundary of the wall of the blood vessel of the head in an image, the sample blood vessel may be a sample blood vessel of a sample head or a sample neck. The sample image may include an axial image of the sample blood vessel. That is, the sample image may be a 2D image corresponding to a point of a centerline of the sample blood vessel. The sample image may be determined in the same way as or similar way to the determination of the image to be segmented as described in 1406. For example, the sample image may be determined based on a sample centerline of the sample blood vessel and a sample initial image relating to the sample blood vessel. The sample initial image may be acquired according to an imaging sequence, such as a dark blood imaging sequence. It should be noted that the sample blood vessel, the sample head, and/or the sample neck illustrated above may be derived from or belong to a same object as the blood vessel described in FIG. 14 or not.

In some embodiments, a training sample may be previously generated and stored in a storage device (e.g., the storage device 130, the storage 220, the storage 390, or an external database). The processing device 120B may retrieve the training sample directly from the storage device. In some embodiments, at least a portion of the training samples may be generated by the processing device 120B. Merely by way of example, an imaging scan may be performed on a sample blood vessel to acquire a sample initial image. The processing device 120B may determine the sample image based on the sample initial image from a storage device where the sample initial image is stored.

In 1504, for each of the plurality of training samples, the processing device 120B (e.g., the obtaining module 460) may obtain a gold standard image corresponding to the sample image. The gold standard image may include a labeled boundary of the lumen and a labeled boundary of the wall of the blood vessel in the sample image.

In some embodiments, pixels corresponding to the boundary of the lumen and the wall of the blood vessel in the sample image may be labeled with the same first labels, and the remaining pixels in the sample image may be labeled with the same second labels. Accordingly, the gold standard image may include pixels with the first labels and pixels with the second labels. The gold standard image may be also referred to as a sample mask.

In some embodiments, the gold standard image may be obtained by labeling the sample image. For example, a user (e.g., a doctor, a technician, an operator) may manually label a sample image to obtain a gold standard image. As another example, the processing device 120B may automatically label a sample image to obtain a gold standard image.

In 1506, the processing device 120B (e.g., the model training module 470) may determine the boundary determination model (also referred to as the second machine learning model) by training an initial machine learning model using the plurality of training samples and a plurality of gold standard images corresponding to the plurality of training samples.

In some embodiments, the initial machine learning model may be an initial model (e.g., an initial machine learning model) before being trained. Exemplary machine learning models may include a convolutional neural network (CNN) model (e.g., a V-NET model, a U-NET model, etc.), a recurrent neural network (RNN) model, a long short term memory (LSTM) network model, a fully convolutional neural network (FCN) model, a generative adversarial network (GAN) model, a radial basis function (RBF) machine learning model, a DeepMask model, a SegNet model, a dilated convolution model, a conditional random fields as recurrent neural networks (CRFasRNN) model, a pyramid scene parsing network (pspnet) model, or the like, or any combination thereof.

The initial machine learning model may include one or more model parameters, such as architecture parameters, learning parameters, etc. In some embodiments, the initial machine learning model may only include a single model.

For example, the initial machine learning model may be a CNN model and exemplary model parameters of the preliminary model may include the number (or count) of layers, the number (or count) of kernels, a kernel size, a stride, a padding of each convolutional layer, a loss function, or the like, or any combination thereof. Before training, the processing device 120B may perform one or more operations on the initial machine learning model and/or the plurality of training samples. For example, the processing device 120B may initialize parameter value(s) of the model parameter(s) of the initial machine learning model. As another example, the processing device 120B may preprocess the training samples (or a portion thereof) that may need to be preprocessed before being used in training the boundary determination model, e.g., by performing image resizing, image resampling, and/or image normalization on the training samples or a portion thereof.

In some embodiments, the initial machine learning model may be trained according to a machine learning algorithm as described elsewhere in this disclosure (e.g., FIG. 14 and the relevant descriptions). For example, the processing device 120B may generate the boundary determination model according to a supervised machine learning algorithm by performing one or more iterations to iteratively update the model parameter(s) of the initial machine learning model.

In some embodiments, for each of the plurality of sample images, the processing device 120B (e.g., the model training module 470) may generate an estimated gold standard image by applying an updated machine learning model determined in a previous iteration. During the application of the updated machine learning model on a sample image, the updated machine learning model may receive the sample image. The updated machine learning model may process the sample image by one or more operations including, e.g., an up-sampling operation, a down-sampling operation, a convolutional operation, etc. The estimated gold standard image may be an output of the updated machine learning model.

In some embodiments, the processing device 120B (e.g., the model training module 470) may determine, based on the estimated gold standard image and a gold standard image corresponding to the each sample image, an assessment result of the updated machine learning model.

The assessment result may indicate an accuracy and/or efficiency of the updated boundary determination model. In some embodiments, the processing device 120B may determine the assessment result by assessing a loss function that relates to the updated boundary determination model. For example, a value of a loss function may be determined to measure a difference between the estimated gold standard image and the gold standard image of the each sample image. The processing device 120B may determine the assessment result based on the value of the loss function. The processing device 120B may determine an overall value of the loss function according to a function (e.g., a sum, a weighted sum, etc.) of the values of the loss functions of the sample images. The processing device 120B may determine the assessment result based on the overall value. Additionally or alternatively, the assessment result may be associated with the amount of time it takes for the updated boundary determination model to generate the estimated gold standard image of each sample image. For example, the shorter the amount of time is, the more efficient the updated boundary determination model may be. In some embodiments, the processing device 120B may determine the assessment result based on the value relating to the loss function(s) aforementioned and/or the efficiency.

In some embodiments, the assessment result may include a determination as to whether a termination condition is satisfied in the current iteration. In some embodiments, the termination condition may relate to the value of the overall loss function. For example, the termination condition may be deemed satisfied if the value of the overall loss function is minimal or smaller than a threshold (e.g., a constant). As another example, the termination condition may be deemed satisfied if the value of the overall loss function converges. In some embodiments, convergence may be deemed to have occurred if, for example, the variation of the values of the overall loss function in two or more consecutive iterations is equal to or smaller than a threshold (e.g., a constant), a certain count of iterations have been performed, or the like. Additionally or alternatively, the termination condition may include that the amount of time it takes for the updated boundary determination model to generate the estimated gold standard image of each sample image is smaller than a threshold.

In some embodiments, in response to a determination that the termination condition is satisfied, the processing device 120B may designate the updated machine learning model as the boundary determination model. That is, the boundary determination model may be determined. Alternatively, the processing device 120B may determine the boundary determination model by combining a plurality of the updated machine learning models in parallel, such that the boundary determination model may receive a plurality of inputs and generate multiple outputs each of which corresponds to one of the plurality of inputs, thereby a plurality of images to be segmented may be processed synchronously by the boundary determination model, which improves the efficiency of the boundary determination model. In response to a determination that the termination condition is not satisfied, the processing device 120B may continue to perform operation 1506, in which the processing device 120B (e.g., the model training module 470) or an optimizer may update the parameter values of the updated machine learning model to be used in a next iteration based on the assessment result.

For example, the processing device 120B or the optimizer may update the parameter value(s) of the updated machine learning model based on the value of the overall loss function according to, for example, a backpropagation algorithm. As another example, for the updated machine learning model, the processing device 120B may update the parameter value(s) of the model based on the value of the corresponding loss function. In some embodiments, a model may include a plurality of parameter values, and updating parameter value(s) of the model refers to updating at least a portion of the parameter values of the model.

It should be noted that the above description regarding process 1500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be added or omitted. For example, the boundary determination model may be stored in a storage device (e.g., the storage device 130) disclosed elsewhere in the present disclosure for further use. As another example, after the boundary determination model is generated, the processing device 120B may further test the boundary determination model using a set of testing images. Additionally or alternatively, the processing device 120B may update the boundary determination model periodically or irregularly based on one or more newly-generated training images (e.g., new sample images and new gold standard images). In some embodiments, each of the plurality of training samples may further include other information of the sample image, such as a position of the sample image, subject information (e.g., an age, a gender, medical history, etc.) of the sample image, etc. The information may be input into the initial machine learning model and/or the updated machine learning model for training. For example, the information may be combined with the sample image. The processing device 120B may input the sample image including the information into a same channel of the initial machine learning model and/or the updated machine learning model. As another example, the processing device 120B may input the sample image and the information into different channels of the initial machine learning model and/or the updated machine learning model.

Figure 17:
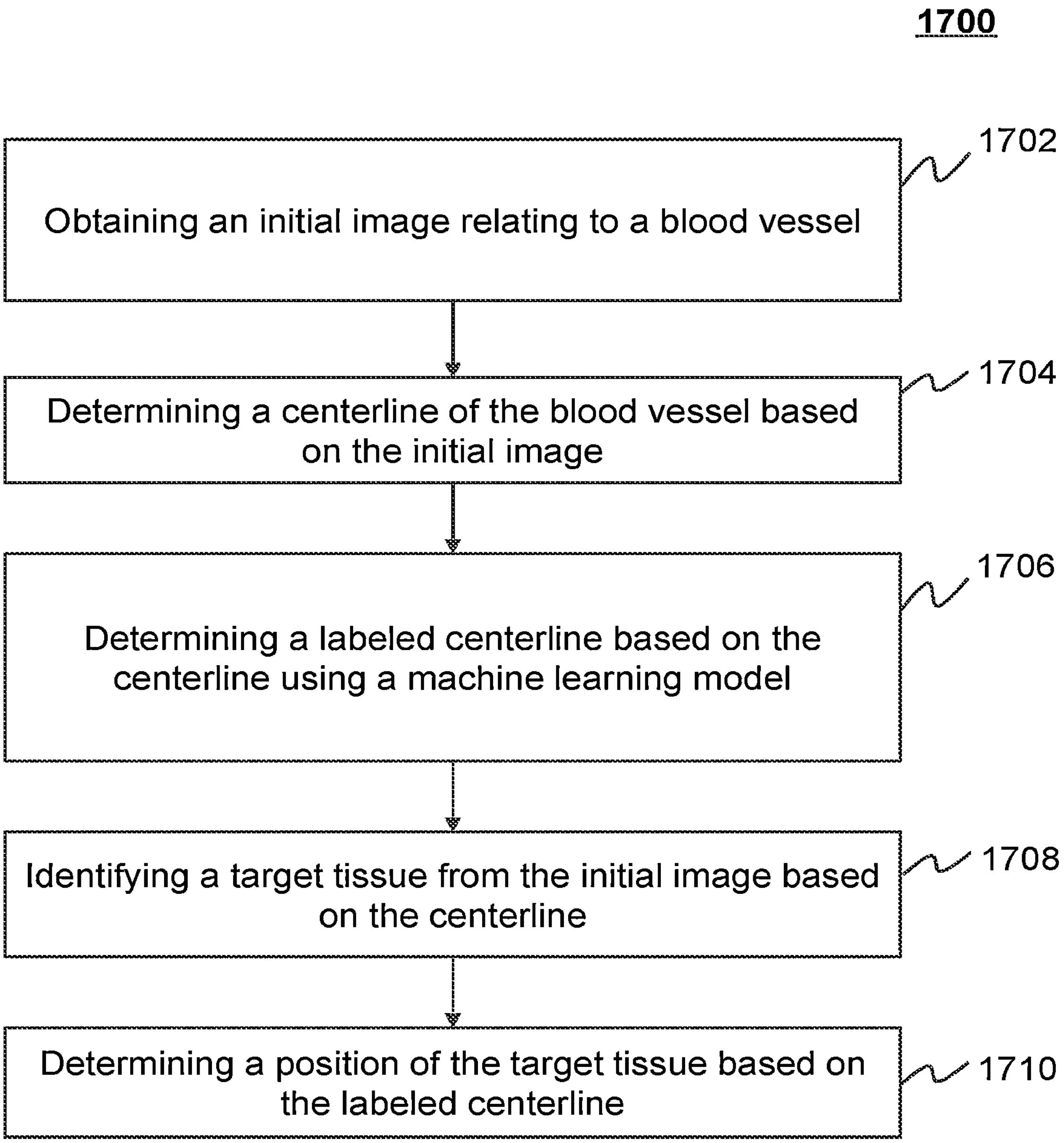
FIG. 17 is a flowchart illustrating an exemplary process for determining a position of a target tissue of a blood vessel according to some embodiments of the present disclosure.

FIG. 17 is a flowchart illustrating an exemplary process 1700 for determining a position of a target tissue of a blood vessel according to some embodiments of the present disclosure. In some embodiments, process 1700 may be implemented as a set of instructions (e.g., an application) stored in a storage device (e.g., the storage device 130, the storage 220, and/or the storage 390). The processing device 120A (e.g., the processor 210, the CPU 340, and/or one or more modules illustrated in FIG. 4A) may execute the set of instructions, and when executing the instructions, the processing device 120A may be configured to perform the process 1700. The operations of the illustrated process presented below are intended to be illustrative. In some embodiments, the process 1700 may be accomplished with one or more additional operations not described and/or without one or more of the operations discussed. Additionally, the order of the operations of process 1700 illustrated in FIG. 17 and described below is not intended to be limiting.

In 1702, the processing device 120A (e.g., the obtaining module 410) may obtain an initial image relating to a blood vessel.

The initial image may include information of at least the lumen and the wall of the blood vessel. More descriptions regarding the initial image may be found elsewhere in the present disclosure (e.g., operation 502, operation 1402 and the descriptions thereof).

In 1704, the processing device 120A (e.g., the determination module 420) may determine a centerline of the blood vessel based on the initial image.

The processing device 120A may determine the centerline of the blood vessel based on an image registration operation, an interactive detection operation, an automatic detection operation, an image recognition model, etc. More descriptions regarding the determination of the centerline of the blood vessel may be found elsewhere in the present disclosure (e.g., operation 1404 and the description thereof).

In 1706, the processing device 120A (e.g., the determination module 420) may determine a labeled centerline based on the centerline using a machine learning model (also referred to as a labeled centerline determination model).

In some embodiments, the labeled centerline may include a name of the centerline and one or more labeled segments of the centerline. The one or more labeled segments may be equal-spaced or not. For example, a distance between any two adjacent labeled segments of the one or more labeled segments may be the same. As another example, a distance between a first pair of adjacent labeled segments may be different from a distance between a second pair of adjacent labeled segments. A distance between two adjacent labeled segments may be a default setting of the image processing system 100 or be preset according to the blood vessel (e.g., a position, a type, a size, etc., of the blood vessel).

The labeled centerline determination model (also referred to as a third machine learning model) may refer to a process or an algorithm for determining a labeled centerline based on a centerline. The labeled centerline determination model may include a convolutional neural network (CNN) model, a recurrent neural network (RNN) model, a deep belief network (DBN) model, a recursive neural tensor network (RNTN) model, a long short term memory (LSTM) network model, a fully convolutional neural network (FCN) model, a generative adversarial network (GAN) model, a radial basis function (RBF) machine learning model, a DeepMask model, a SegNet model, a dilated convolution model, a conditional random fields as recurrent neural networks (CRFasRNN) model, a pyramid scene parsing network (pspnet) model, or the like, or any combination thereof. In some embodiments, the processing device 120A may determine the labeled centerline by inputting the centerline into the labeled centerline determination model.

In some embodiments, the processing device 120A (e.g., the obtaining module 410) may obtain the labeled centerline determination model from one or more components of the image processing system 100 (e.g., the storage device 130, the terminals(s) 140) or an external source via a network (e.g., the network 150). For example, the labeled centerline determination model may be previously generated by a computing device (e.g., the processing device 120B), and stored in a storage device (e.g., the storage device 130, the storage 220, and/or the storage 390) of the image processing system 100. The processing device 120A may access the storage device and retrieve the labeled centerline determination model. In some embodiments, the labeled centerline determination model may be generated according to a machine learning algorithm. The machine learning algorithm may include but not be limited to an artificial neural network algorithm, a deep learning algorithm, a decision tree algorithm, an association rule algorithm, an inductive logic programming algorithm, a support vector machine algorithm, a clustering algorithm, a Bayesian network algorithm, a reinforcement learning algorithm, a representation learning algorithm, a similarity and metric learning algorithm, a sparse dictionary learning algorithm, a genetic algorithm, a rule-based machine learning algorithm, or the like, or any combination thereof. The machine learning algorithm used to generate the labeled centerline determination model may be a supervised learning algorithm, a semi-supervised learning algorithm, an unsupervised learning algorithm, etc. In some embodiments, the labeled centerline determination model may be generated by a computing device (e.g., the processing device 120B) by performing a process (e.g., process 1800) for generating a labeled centerline determination model disclosed herein. More descriptions regarding the generation of the labeled centerline determination model may be found elsewhere in the present disclosure. See, e.g., FIG. 18 and relevant descriptions thereof.

In 1708, the processing device 120A (e.g., the determination module 420) may identify the target tissue from the initial image based on the centerline. The target tissue may include a lesion, such as a plaque, an ulceration, a thrombosis, an inflammation, an obstruction, a tumor, etc.

In some embodiments, the processing device 120A may determine one or more images of the blood vessel to be segmented based on the centerline and the initial image. Each of the one or more images may be an axial image of the blood vessel. For each of the one or more images, the processing device 120A may determine a boundary of the lumen of the blood vessel and a boundary of the wall of the blood vessel in the each image, for example, using the boundary determination model. For the each image, the processing device 120A may determine one or more vascular parameters of the blood vessel included in the each image based on the boundary of the lumen and the boundary of the wall corresponding to the each image. The one or more vascular parameters may include a diameter stenosis, a normal wall index, an area stenosis, or the like, or any combination thereof. More descriptions regarding determining the one or more vascular parameters may be found elsewhere in the present disclosure (e.g., operation 1410 and the descriptions thereof).

Further, the processing device 120A may identify the target tissue based on the vascular parameters of the one or more images. In some embodiments, the processing device 120A may compare the one or more vascular parameters of the blood vessel with one or more reference vascular parameters of the blood vessel to determine a target portion of the blood vessel. The target portion may include a stenosis portion, a swelling portion, or the like, or any combination thereof. For example, if a reference area of the wall is 72 square millimeters and a determined area of the wall included in an image is 13 square millimeters, a position corresponding to the image may be determined as a stenosis portion of the blood vessel. As another example, if a reference area of the wall is 50 square millimeters and a determined area of the wall included in an image is 60 square millimeters, a position corresponding to the image may be determined as a swelling portion of the blood vessel. In some embodiments, the processing device 120A may determine whether an area stenosis of a portion corresponding to the image is within a preset range. For example, if the area stenosis of the portion is larger than 70%, the processing device 120A may determine that the stenosis of the portion is not serious. As another example, if the area stenosis of the portion is less than 30%, the processing device 120A may determine that the stenosis of the portion is serious.

In some embodiments, after determining the target portion of the blood vessel, the processing device 120A may identify one or more components between the lumen and the wall of the blood vessel in each of image(s) corresponding to the target portion of the blood vessel. The one or more components may include a calcification, a lipid core, a loose substrate, a fibrous cap, a plaque hemorrhage, an ulceration, etc. For example, the processing device 120A may identify one or more components according to one or more detection technologies (e.g., an image identification algorithm). As another example, the processing device 120A may identify one or more components according to the experiences of a user. In some embodiments, the processing device 120A may identify the target tissue based on the vascular parameters of the one or more images and the identified components in the one or more images. For example, the processing device 120A may determine areas and proportions of the identified components in the one or more images. A proportion of an identified component may refer to a ratio of an area of the identified component to an area of the wall of the blood vessel. The processing device 120A may further identify the target tissue based on the vascular parameters of the one or more images and/or the areas and proportions of the identified components. For example, in response to determining that an area and/or a ratio of an identified component reaches a preset condition (e.g., a preset area and/or a preset ratio), the processing device 120A may determine that the target portion includes the target tissue.

In 1710, the processing device 120A (e.g., the determination module 420) may determine the position of the target tissue based on the labeled centerline.

Since the each image is determined based on the centerline of the blood vessel, a corresponding relationship between the each image and a position of the blood vessel included in the each image may be known. The processing device 120A may determine the position of the target tissue based on the corresponding relationship and the labeled centerline. For example, the processing device 120A may determine a position of the blood vessel included in the image on which the target tissue is identified based on the corresponding relationship. The processing device 120A may further determine a target labeled segment of the labeled centerline corresponding to the image based on the position of the blood vessel included in the image. That is, the position of the target tissue may be indicated or represented by the target labeled segment of the labeled centerline (or the position of the target labeled segment). In some embodiments, the processing device 120A may determine the target labeled segment as the position of the target tissue.

In some embodiments, the processing device 120A may generate a report relating to the target tissue. The report may include a name of the target tissue, a label of a segment of the centerline corresponding to the target tissue. The processing device 120A may further transmit the report to a terminal (e.g., the terminal 140) for display. Alternatively, the processing device 120A may cause the report to be printed to display the report on paper. According to the report, the user can determine the position of the target tissue quickly and accurately, thereby facilitating subsequent analysis (e.g., a pathologic analysis of the target tissue).

It should be noted that the above description regarding the process 1700 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations of the process 1700 may be omitted, and/or one or more additional operations may be added. For example, a storing operation may be added elsewhere in the process 1700. In the storing operation, the processing device 120A may store information and/or data (e.g., the initial image related to the blood vessel, the labeled centerline determination model, the labeled centerline, the position of the target tissue, etc.) associated with the image processing system 100 in a storage device (e.g., the storage device 130) disclosed elsewhere in the present disclosure. In some embodiments, in operation 1708, the target tissue may be identified using an image processing technique. In some embodiments, in operation 1708, the processing device 120A may obtain one or more second initial images relating to the blood vessel. The processing device 120A may identify the target tissue based on the initial image and/or the second initial images. For example, the processing device 120A may register the second initial images to the initial image. The processing device 120A may obtain, for each of the second initial image, one or more second images of the blood vessel to be segmented based on the centerline of the blood vessel. The processing device 120A may determine the target tissue based on at least one of the one or more images and/or at least one of the second images. In some embodiments, each of the second initial image(s) may be acquired by a second imaging device. The second imaging device may be same as or different from a first imaging device that is used to acquire the first initial image. For example, the first initial image may be acquired by an MRI device, and the one or more second initial images may also be acquired by the MRI device or another MRI device. As another example, the first initial image may be acquired by an MRI device, and the one or more second initial images may be acquired by a CT device. In some embodiments, each of the second initial image(s) may be acquired using a second imaging sequence. The second imaging sequence may be different from a first imaging sequence corresponding to the initial image. For example, if the first imaging sequence is a dark blood imaging sequence, the second imaging sequence may be a bright blood imaging sequence or another dark blood imaging sequence. In some embodiments, the second initial image(s) may be acquired using different second imaging sequences.

Figure 18:
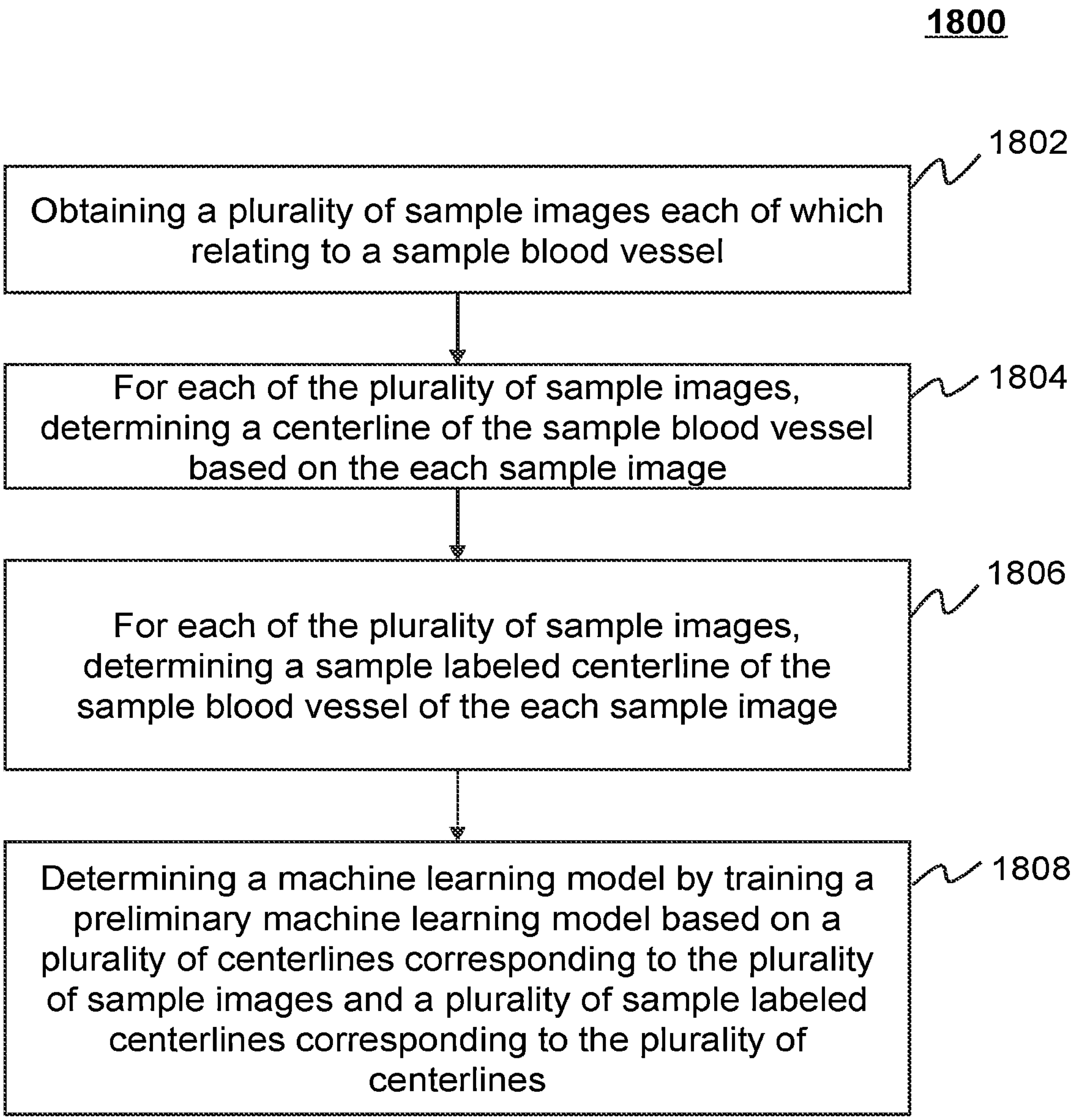
FIG. 18 is a flowchart illustrating an exemplary process for generating a labeled centerline determination model according to some embodiments of the present disclosure.

FIG. 18 is a flowchart illustrating an exemplary process 1800 for generating a labeled centerline determination model according to some embodiments of the present disclosure. In some embodiments, the process 1800 may be implemented as a set of instructions (e.g., an application) stored in a storage device (e.g., the storage device 130, storage 220, and/or storage 390). The processing device 120B (e.g., the processor 210, the CPU 340, and/or one or more modules illustrated in FIG. 4B) may execute the set of instructions, and when executing the instructions, the processing device 120B may be configured to perform the process 1800. The operations of the illustrated process presented below are intended to be illustrative. In some embodiments, the process 1800 may be accomplished with one or more additional operations not described and/or without one or more of the operations discussed. Additionally, the order of the operations of process 1800 illustrated in FIG. 18 and described below is not intended to be limiting. In some embodiments, the labeled centerline determination model described in connection with operation 1706 in FIG. 17 may be obtained according to the process 1800. In some embodiments, the process 1800 may be performed by another device or system other than the image processing system 100, e.g., a device or system of a vendor of a manufacturer. For illustration purposes, the implementation of the process 1800 by the processing device 120B is described as an example.

In 1802, the processing device 120B (e.g., the obtaining module 460) may obtain a plurality of sample images. Each of the plurality of sample images may relate to a sample blood vessel.

The sample blood vessel may be of the same type as or a different type from the blood vessel as described in connection with FIG. 17. For example, if the labeled centerline determination model is used to determine a labeled centerline of the blood vessel of the head in an image, the sample blood vessel may be a sample blood vessel of a sample head or a different blood vessel of a sample neck. The sample images may include images relating to a sample blood vessel. The acquisition of the sample image may be the same as or similar to the acquisition of the initial image as described in 1702. For example, the sample image may be a 3D image acquired according to an imaging sequence, such as a dark blood imaging sequence, a bright blood imaging sequence, etc. More descriptions regarding the obtaining of the sample image may be found elsewhere in the present disclosure (e.g., operation 1702 and the descriptions thereof).

In some embodiments, a sample image may be previously generated and stored in a storage device (e.g., the storage device 130, the storage 220, the storage 390), or an external database. The processing device 120B may retrieve the sample image directly from the storage device. In some embodiments, at least a portion of the sample images may be generated by the processing device 120B. Merely by way of example, an imaging scan may be performed on a sample blood vessel to acquire a sample image relating to the sample blood vessel. The processing device 120B may acquire the sample image(s) relating to the sample blood vessel from a storage device where the sample image(s) relating to the sample blood vessel is stored.

In some embodiments, the sample images (or a portion thereof) may need to be preprocessed before being used in training the labeled centerline determination model. For example, for a sample image, the processing device 120B may perform image resizing, image resampling, and image normalization on the sample image relating to the sample blood vessel.

In 1804, for each of the plurality of sample images, the processing device 120B (e.g., the obtaining module 460) may determine a centerline of the sample blood vessel based on the each sample image.

The centerline of the sample blood vessel may refer to a line located in and along the sample blood vessel. In some embodiments, the centerline of the sample blood vessel may refer to a collection of pixels located in or close to a central area of the sample blood vessel. In some embodiments, the centerline of the blood vessel may refer to a line connecting pixels with an equal distance or substantially equal distance to the boundary of the lumen of the sample blood vessel. The determination of the centerline of the sample blood vessel may be the same as or similar to the determination of the centerline of the blood vessel as described in 1704, which is not repeated herein.

In 1806, for each of the plurality of sample images, the processing device 120B (e.g., the obtaining module 460) may determine a sample labeled centerline of the sample blood vessel of the each sample image.

In some embodiments, the sample labeled centerline of the sample blood vessel may include a sample name of the centerline of the sample blood vessel and sample labeled segments of the centerline of the sample blood vessel. In some embodiments, the sample labeled segments of the centerline of the sample blood vessel may be equal-spaced or not. For example, a distance between any two adjacent sample labeled segments may be the same. As another example, a distance between a first pair of adjacent sample labeled segments may be different from a distance between a second pair of adjacent sample labeled segments. A distance between two adjacent labeled segments may be a default setting of the image processing system 100 or be preset according to the blood vessel (e.g., a position, a type, a size, etc., of the blood vessel). In some embodiments, a sample labeled centerline may include a plurality of labels corresponding to the sample name and the sample labeled segments of the centerline of the sample blood vessel. A label corresponding to one of the sample labeled segments may be labeled on an end of the sample labeled segment. A position of the label (e.g., a coordinate of the end of the sample labeled segment) may be determined, e.g., from a view of the sample blood vessel that is different from a view of the sample blood vessel in the sample image. Each of the labels of the sample labeled segments and the position of the each label may be stored as a file (e.g., a text file). The file may include information of the each label of the each sample labeled segment and the position of the each label. Taking the sample blood vessel of a sample head (or brain) as an example, the sample blood vessel of the sample head may include a sample vertebral artery and a sample internal carotid artery. The sample vertebral artery may include a sample pre-foraminal segment with a label of V1 segment, a sample foraminal segment with a label of V2 segment, a sample extradural or extraspinal segment with a label of V3 segment, a sample intradural segment with a label of V4 segment. The sample internal carotid artery may include a sample cervical segment with a label of C1 segment, a sample petrous segment with a label of C2 segment, a sample lacerum segment with a label of C3 segment, a cavernous segment with a label of C4 segment, a sample clinoid segment with a label of C5 segment, a sample ophthalmic segment with a label of C6 segment, and a sample communicating segment with a label of C7 segment.

In some embodiments, the sample labeled centerline of the sample blood vessel may be obtained by labeling the centerline of the sample blood vessel. For example, a user (e.g., a doctor, a technician, an operator) may manually label a centerline of the sample blood vessel to obtain a sample name of the centerline of the sample blood vessel and sample labeled segments of the centerline of the sample blood vessel. As another example, the processing device 120B may automatically label a centerline of the sample blood vessel to obtain a sample name of the centerline of the sample blood vessel and sample labeled segments of the centerline of the sample blood vessel.

In 1808, the processing device 120B (e.g., the model training module 470) may determine the labeled centerline determination model (also referred to as the third machine learning model) by training a preliminary machine learning model using a plurality of centerlines corresponding to the plurality of sample images and a plurality of sample labeled centerlines corresponding to the plurality of centerlines. Each of the plurality of sample labeled centerlines may include a sample name and sample labeled segments.

In some embodiments, the preliminary machine learning model may be an initial model (e.g., an initial machine learning model) before being trained. Exemplary machine learning models may include a convolutional neural network (CNN) model, a recurrent neural network (RNN) model, a deep belief network (DBN) model, a recursive neural tensor network (RNTN) model, a long short term memory (LSTM) network model, a fully convolutional neural network (FCN) model, a generative adversarial network (GAN) model, a radial basis function (RBF) machine learning model, a DeepMask model, a SegNet model, a dilated convolution model, a conditional random fields as recurrent neural networks (CRFasRNN) model, a pyramid scene parsing network (pspnet) model, or the like, or any combination thereof.

The preliminary machine learning model may include one or more model parameters, such as architecture parameters, learning parameters, etc. In some embodiments, the preliminary machine learning model may only include a single model. For example, the preliminary machine learning model may be a CNN model and exemplary model parameters of the preliminary model may include the number (or count) of layers, the number (or count) of kernels, a kernel size, a stride, a padding of each convolutional layer, a loss function, or the like, or any combination thereof. Before training, the model parameter(s) of the preliminary machine learning model may have their respective initial values. For example, the processing device 120B may initialize parameter value(s) of the model parameter(s) of the preliminary machine learning model.

In some embodiments, the preliminary machine learning model may be trained according to a machine learning algorithm as described elsewhere in this disclosure (e.g., FIG. 17 and the relevant descriptions). For example, the processing device 120B may generate the labeled centerline determination model according to a supervised machine learning algorithm by performing one or more iterations to iteratively update the model parameter(s) of the preliminary machine learning model.

In some embodiments, for each of the plurality of sample images, the processing device 120B (e.g., the model training module 470) may generate an estimated labeled centerline by applying an updated machine learning model determined in a previous iteration. During the application of the updated machine learning model on a sample image, the updated machine learning model may receive the sample image. The estimated labeled centerline may be an output of the updated machine learning model.

In some embodiments, the processing device 120B (e.g., the model training module 470) may determine, based on the estimated labeled centerline and a sample labeled centerline of each sample image, an assessment result of the updated machine learning model.

The assessment result may indicate an accuracy and/or efficiency of the updated labeled centerline determination model. In some embodiments, the processing device 120B may determine the assessment result by assessing a loss function that relates to the updated labeled centerline determination model. For example, a value of a loss function may be determined to measure a difference between the estimated labeled centerline and the sample labeled centerline of the each sample image. The processing device 120B may determine the assessment result based on the value of the loss function. The processing device 120B may determine an overall value of the loss function according to a function (e.g., a sum, a weighted sum, etc.) of the values of the loss functions of the sample images. The processing device 120B may determine the assessment result based on the overall value.

Additionally or alternatively, the assessment result may be associated with the amount of time it takes for the updated labeled centerline determination model to generate the estimated labeled centerline of each sample image. For example, the shorter the amount of time is, the more efficient the updated labeled centerline determination model may be. In some embodiments, the processing device 120B may determine the assessment result based on the value relating to the loss function(s) aforementioned and/or the efficiency.

In some embodiments, the assessment result may include a determination as to whether a termination condition is satisfied in the current iteration. In some embodiments, the termination condition may relate to the value of the overall loss function. For example, the termination condition may be deemed satisfied if the value of the overall loss function is minimal or smaller than a threshold (e.g., a constant). As another example, the termination condition may be deemed satisfied if the value of the overall loss function converges. In some embodiments, convergence may be deemed to have occurred if, for example, the variation of the values of the overall loss function in two or more consecutive iterations is equal to or smaller than a threshold (e.g., a constant), a certain count of iterations have been performed, or the like. Additionally or alternatively, the termination condition may include that the amount of time it takes for the updated labeled centerline determination model to generate the estimated labeled centerline of each sample image is smaller than a threshold.

In some embodiments, in response to a determination that the termination condition is satisfied, the processing device 120B may designate the updated machine learning model as the labeled centerline determination model. That is, the labeled centerline determination model may be determined. In response to a determination that the termination condition is not satisfied, the processing device 120B may continue to perform operation 1808, in which the processing device 120B (e.g., the model training module 470) or an optimizer may update the parameter values of the updated machine learning model to be used in a next iteration based on the assessment result.

For example, the processing device 120B or the optimizer may update the parameter value(s) of the updated machine learning model based on the value of the overall loss function according to, for example, a backpropagation algorithm. As another example, for the updated machine learning model, the processing device 120B may update the parameter value(s) of the model based on the value of the corresponding loss function. In some embodiments, a model may include a plurality of parameter values, and updating parameter value(s) of the model refers to updating at least a portion of the parameter values of the model.

It should be noted that the above description regarding process 1800 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be added or omitted. For example, the labeled centerline determination model may be stored in a storage device (e.g., the storage device 130) disclosed elsewhere in the present disclosure for further use. As another example, after the labeled centerline determination model is generated, the processing device 120B may further test the labeled centerline determination model using a set of testing images. Additionally or alternatively, the processing device 120B may update the labeled centerline determination model periodically or irregularly based on one or more newly-generated training images (e.g., new sample images and new sample labeled centerline). As still another example, operation 1802 may be omitted. That is, the processing device 120B may directly obtain a plurality of sample images whose centerlines have been labeled.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms “one embodiment,” “an embodiment,” and/or “some embodiments” mean that a particular feature, structure or characteristic described in connection with the embodiment is included in at least one embodiment of the present disclosure. Therefore, it is emphasized and should be appreciated that two or more references to “an embodiment” or “one embodiment” or “an alternative embodiment” in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a “unit,” “module,” or “system.” Furthermore, aspects of the present disclosure may take the form of a computer program product embodied in one or more computer-readable media having computer-readable program code embodied thereon.

A non-transitory computer-readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer-readable signal medium may be any computer-readable medium that is not a computer-readable storage medium and that may communicate, propagate, or transport a program for use by or in connection with an instruction execution system, apparatus, or device. Program code embodied on a computer-readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python or the like, conventional procedural programming languages, such as the “C” programming language, Visual Basic, Fortran, Perl, COBOL, PHP, ABAP, dynamic programming languages such as Python, Ruby, and Groovy, or other programming languages. The program code may execute entirely on the user’s computer, partly on the user’s computer, as a stand-alone software package, partly on the user’s computer and partly on a remote computer or entirely on the remote computer or server. In the latter scenario, the remote computer may be connected to the user’s computer through any type of network, including a local cell network (LAN) or a wide cell network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed object matter requires more features than are expressly recited in each claim Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate" or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system, comprising:

a storage device storing a set of instructions;

at least one processor in communication with the storage device, wherein when executing the set of instructions, the at least one processor is configured to direct the system to perform operations including:

obtaining an initial image relating to a blood vessel, the initial image including information of at least a lumen and a wall of the blood vessel;

determining a centerline of the blood vessel based on the initial image;

determining one or more images to be segmented of the blood vessel based on the centerline and the initial image, each of the one or more images being an axial image of the blood vessel;

for each of the one or more images, determining a boundary of the lumen of the blood vessel and a boundary of the wall of the blood vessel in the each image; and analyzing the blood vessel based on one or more boundaries of the lumen and one or more boundaries of the wall by:

for the each image, determining one or more vascular parameters of the blood vessel included in the each image based on the boundary of the lumen and the boundary of the wall corresponding to the each image.

2. The system of claim 1, wherein the initial image is a three-dimensional image acquired using a first imaging sequence.

3. The system of claim 2, wherein the first imaging sequence includes a dark blood imaging sequence or a bright blood imaging sequence.

4. The system of claim 2, wherein the determining the centerline of the blood vessel based on the initial image includes:

determining an enhanced image based on the initial image using a first machine learning model, the enhanced image indicating path information of the centerline of the blood vessel; and determining the centerline of the blood vessel based on the enhanced image.

5. The system of any one of claim 4, wherein the determining an enhanced image based on the initial image using a first machine learning model includes:

obtaining one or more second initial images relating to the blood vessel, each of the one or more second initial images being acquired using a second imaging sequence different from the first imaging sequence;

registering the one or more second initial images and the initial image;

determining the enhanced image based on the initial image and the one or more registered second initial images using the first machine learning model.

6. The system of claim 5, wherein the at least one processor is further configured to direct the system to perform operations including:

determining a set of first curved planar reformation (CPR) images and a set of first multi planar reformation (MPR) images based on the centerline of the blood vessel and a first image;

for each of one or more second images, determining a set of second CPR images and a set of second MPR images based on the centerline of the blood vessel and the each second image; and causing the set of first CPR images, the set of first MPR images, the one or more sets of second CPR images, and the one or more sets of second MPR images to be synchronously displayed on an interface.

7. The system of claim 4, wherein the determining the centerline of the blood vessel based on the enhanced image includes:

determining at least two key points of the centerline based on the enhanced image; and determining the centerline of the blood vessel based on the at least two key points and the enhanced image.

8. The system of claim 7, wherein the determining the centerline of the blood vessel based on the at least two key points and the enhanced image includes:

determining at least two first initial key points; and determining the at least two key points based on the at least two first initial key points and the enhanced image.

9. The system of claim 4, wherein the first machine learning model is obtained according to operations including:

obtaining a plurality of training samples each of which includes at least one sample image relating to a sample blood vessel;

for each of the plurality of training samples, obtaining a first gold standard image corresponding to the at least one sample image, the first gold standard image indicating path information of a sample centerline of the sample blood vessel; and determining the first machine learning model by training an initial machine learning model using the plurality of training samples and a plurality of first gold standard images.

10. The system of claim 9, wherein the obtaining the first gold standard image corresponding to the at least one sample image includes:

determining the sample centerline of the sample blood vessel based on the at least one sample image;

for each point on the sample centerline, determining a Gaussian kernel centered at the point; and determining the first gold standard image by superimposing a plurality of Gaussian kernels corresponding to a plurality of points on the sample centerline.

11. The system of claim 9, wherein the determining the first machine learning model by training the initial machine learning model using the plurality of training samples and the plurality of first gold standard images includes:

for each of the plurality of training samples, obtaining a second gold standard image corresponding to the at least one sample image, the second gold standard image indicating information of at least two sample key points of the sample centerline of the sample blood vessel;

determining the first machine learning model by training the initial machine learning model using the plurality of training samples, the plurality of first gold standard images, and a plurality of second gold standard images.

12. The system of claim 1, wherein the determining a boundary of the lumen of the blood vessel and a boundary of the wall of the blood vessel in the each image includes:

determining one or more outputs corresponding to the one or more images respectively by inputting the one or more images into a second machine learning model; and determining the boundary of the lumen of the blood vessel and the boundary of the wall of the blood vessel in the each image based on one of the one or more outputs corresponding to the each image.

13. The system of claim 12, wherein the determining one or more outputs corresponding to the one or more images respectively by inputting the one or more images into a second machine learning model includes:

adjusting a resolution of the each image until a preset resolution is satisfied; and determining the one or more outputs by inputting the one or more adjusted images into the second machine learning model.

14. The system of claim 1, wherein the determining one or more images to be segmented of the blood vessel based on the centerline and the initial image includes:

determining one or more intermediate images by segmenting the initial image along a direction perpendicular to the centerline; and for each of the one or more intermediate images, determining a portion of the intermediate image as one of the one or more images, each of the one or more images having a smaller size than its corresponding intermediate image as long as including the blood vessel included in the corresponding intermediate image.

15. The system of claim 1, wherein the one or more vascular parameters include at least one of a diameter stenosis, a normal wall index, or an area stenosis.

16. The system of claim 1, wherein the analyzing the blood vessel based on the one or more boundaries of the lumen and the one or more boundaries of the wall includes:

determining whether the blood vessel has a target tissue based on the one or more vascular parameters of each of the one or more images; and in response to determining that the blood vessel has the target tissue, determining a position of the target tissue.

17. The system of claim 16, wherein the determining a position of the target tissue includes:

determining a labeled centerline based on the centerline using a third machine learning model, wherein the labeled centerline includes a name of the centerline and one or more labeled segments of the centerline; and determining the position of the target tissue based on the target tissue and the labeled centerline.

18. A method implemented on a computing device including at least one processor and at least one storage medium, the method comprising:

obtaining an initial image relating to a blood vessel, the initial image including information of at least a lumen and a wall of the blood vessel;

determining a centerline of the blood vessel based on the initial image;

determining one or more images to be segmented of the blood vessel based on the centerline and the initial image, each of the one or more images being an axial image of the blood vessel;

for each of the one or more images, determining a boundary of the lumen of the blood vessel and a boundary of the wall of the blood vessel in the each image; and analyzing the blood vessel based on one or more boundaries of the lumen and one or more boundaries of the wall by:

for the each image, determining one or more vascular parameters of the blood vessel included in the each image based on the boundary of the lumen and the boundary of the wall corresponding to the each image.

19. A non-transitory computer readable medium, comprising executable instructions that, when executed by at least one processor, direct the at least one processor to perform a method, the method comprising:

obtaining an initial image relating to a blood vessel, the initial image including information of at least a lumen and a wall of the blood vessel;

determining a centerline of the blood vessel based on the initial image;

determining one or more images to be segmented of the blood vessel based on the centerline and the initial image, each of the one or more images being an axial image of the blood vessel;

for each of the one or more images, determining a boundary of the lumen of the blood vessel and a boundary of the wall of the blood vessel in the each image; and analyzing the blood vessel based on one or more boundaries of the lumen and one or more boundaries of the wall by:

for the each image, determining one or more vascular parameters of the blood vessel included in the each image based on the boundary of the lumen and the boundary of the wall corresponding to the each image.

* * * * *